(12) United States Patent
Hensley

(10) Patent No.: US 7,683,055 B2
(45) Date of Patent: Mar. 23, 2010

(54) LANTHIONINE-RELATED COMPOUNDS FOR THE TREATMENT OF INFLAMMATORY DISEASES

(75) Inventor: Kenneth Hensley, Oklahoma City, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 455 days.

(21) Appl. No.: 11/621,469

(22) Filed: Jan. 9, 2007

(65) Prior Publication Data

US 2007/0197515 A1 Aug. 23, 2007

Related U.S. Application Data

(60) Provisional application No. 60/757,252, filed on Jan. 9, 2006, provisional application No. 60/781,794, filed on Mar. 13, 2006, provisional application No. 60/804,149, filed on Jun. 7, 2006.

(51) Int. Cl.
C07D 279/12 (2006.01)
A61K 31/54 (2006.01)

(52) U.S. Cl. ............................... 514/227.5; 544/58.4

(58) Field of Classification Search ............... 544/58.4; 514/227.5
See application file for complete search history.

(56) References Cited

U.S. PATENT DOCUMENTS

| | | | | |
|---|---|---|---|---|
| 6,025,395 | A | 2/2000 | Breitner et al. | ............... 514/570 |
| 2003/0166554 | A1 | 9/2003 | Cohen et al. | .................. 514/12 |
| 2003/0185754 | A1 | 10/2003 | Cohen et al. | ................. 424/9.2 |

OTHER PUBLICATIONS

Peter Hermann, Chemische Berichte, 94:442-445, 1961.*
Eremeev et al. Khimiya Geterotsiklicheskikh Soedinenii (1983), 10, 1357-8.*
Eremeev et al. Zhurnal Organicheskoi Khimii (1985), 21(10), 2239-41.*
Paglialunga et al. Journal of Heterocyclic Chemistry (1990), 27(6), 1661-1664.*
Vippagunta et al. "Crystalline Solids," Advanced Drug Delivery Reviews, 2001, 48, pp. 18).*
Bagasra et al., "Activation of the inducible form of nitric oxide synthase in the brains of patients with multiple sclerosis," *Proc. Natl. Acad. Sci. USA*, 92:12041-12045, 1995.
Bauer et al., "Characterization of p40/GPR69A as a peripheral membrane protein related to the lantibiotic synthetase component c," *Biochem. Biophys. Res. Commun.*, 275:69-74, 2000.
Beal et al., "Replication of the neurochemical characteristics of Huntington's disease by quinolinic acid," *Nature*, 321:168-171, 1986.
Beal, "Mitochondria, free radicals, and neurodegeneration," *Curr. Opin. Neurobiol.*, 6:661-666, 1996.
Berg et al., In: *Biochemistry*, 6th Ed.; W.H. Freeman, pp. 689-696, 2006.
Blight et al., "Quinolinic acid accumulation in injured spinal cord: time course, distribution, and species differencs between rat and guinea pig," *J. Neurotraum.*, 14:89-98; 1997.
Blisnick et al., "LANCL1, an erythrocyte protein recruited to the Maurer's clefts during *Plasmodium falciparum* development," *Mol. Biochem. Parasitol.*, 141:39-47, 2005.
Brown et al., "The stereoisomeric forms of lanthionine," *Journal of Biological Chemistry* 140:767-771, 1941.
Cavallini et al., "1,4-Thiomorpholine-3,5-dicarboxylic acid, a novel cyclic imino acid detected in bovine brain," *FEBS Lett. 3122*, 192:247-250; 1985.
Cavallini et al., "Sulfur-containing cyclic ketimines and imino acids," *Eur. J. Biochem.*, 202:217-223; 1991.
Cavallini et al., "The ketimine derivatives of thialysine, lanthionine, cystathionine, cystine: preparation and properties," In: *Sulfur Amino Acids: Biochemical and Clinical Aspects*, Alan R. Liss Inc., 355-364, 1983.
Chatterjee et al., "Biosynthesis and mode of action of lantibiotics," *Chem Rev.*, 105:633-684, 2005.
Chiarugi et al., "Kynurenine 3-mono-oxygenase activity and neurotoxic kynurenine metabolites increase in the spinal cord of rats with experimental allergic encephalomyelitis," *Neurosci.*, 102:687-695; 2001.
Cooper, "The role of glutamine transaminase K (GTK) in sulfur and α-keto acid metabolism in the brain, and in the possible bioactivation of neurotoxicants," *Neurochem. Int.*, 44:557-577; 2004.
Coyle and Puttfarcken, "Oxidative stress, glutamate, and neurodegenerative disorders," *Science*, 262:689-695, 1993.
Culver et al., "In vivo gene transfer with retroviral vector-producer cells for treatment of experimental brain tumors," *Science*, 256(5063):1550-1552, 1992.
Desagher et al., "Pyruvate protects neurons against hydrogen peroxide-induced toxicity," *J. Neurosci.*, 17:9060-9067, 1997.
Fontana et al., "[$^{35}$S]Lanthionine ketimine binding to bovine brain membranes," *Biochem. Biophys. Res. Commun.*, 171:480-486; 1990.
Fontana et al., "Detection of cystathionine ketimine and lanthionine ketimine in human brain," *Neurochem. Res.*, 22:821-844; 1997.
Foster et al., "Kynurenic acid analogues with improved affinity and selectivity for the glycine site on the N-Methyl-D-apartate receptor from rat brain," *Mol. Pharmacol.*, 41:914-922, 1992.
Giulidori et al., "Transmethylation, transsulfuration, and aminopropylation reactions of S-Adenosyl-L-Methionine in Vivo," *J. Biol. Chem.*, 259:4205-4211, 1984.
Guidetti et al., "Neostiatal and cortical quinolinate levels are increased in early grade Huntington's disease," *Neurobiol. Dis.*, 17:455-461; 2004.

(Continued)

*Primary Examiner*—Kahsay T Habte
(74) *Attorney, Agent, or Firm*—Fulbright & Jaworski LLP

(57) ABSTRACT

The present invention provides compositions comprising lanthionine ketimine derivatives and thiomorpholine dicarboxylic acid derivatives, as well as processes for the preparation of such compounds. The invention also concerns the use of lanthionine, lanthionine ketimine (LK), LK derivatives, thiomorpholine dicarboxylic acid (TMDCA), and TMDCA derivatives. It concerns the use of these compounds for the treatment and/or prevention diseases, including diseases affecting the central nervous system. The invention provides for compounds and methods having anti-oxidant, anti-neuroinflammatory and neuroprotective activities. It also provides for compounds having the ability to pass through and/or be transported through cellular membranes, such the blood-brain barrier.

38 Claims, 17 Drawing Sheets

OTHER PUBLICATIONS

Guillemin et al., "Implications for the kynurenine pathway and quinolinic acid in amyotrophic lateral sclerosis," *Neurodegener. Dis.*, 2:166-176, 2005.

Guillemin et al., "Indoleamine 2,3 dioxygenase and quinolinic acid immunoreactivity in alzheimer's disease hippocampus," *Neuropathol. Appl. Neurobiol.*, 31:395-404; 2005.

Guillemin et al., "Quinolinic acid in the pathogenesis of Alzheimer's disease," *Adv. Exp. Med. Biol.*, 527:167-176; 2003.

Harpp et al., "Preparation and mass spectral properties of cystine and lanthionine derivatives. a novel sythesis of $_L$-Lanthionine by selective desulfurization," *Journal of Organic Chemistry* 36:73-80, 1971.

Hensley et al., "Message and protein-level elevation of tumor necrosis factor α (TNFα) and TNF α-modulating cytokines in spinal cords of the G93A-SOD1 mouse model for amyotrophic lateral sclerosis," *Neurobio. Dis.* 14: 74-80; 2003.

Hensley et al., "Primary glia expressing the G93A-SOD1 mutation present a neuroinflammatory phenotype and provide a cellular system for studies of glial inflammation," *J. Neuroinflammation*, 3:2; 2006.

Hensley et al., "Temporal patterns of cytokine and apoptosis-related gene expression in spinal cords of the G93A-SOD1 mouse model of amyotrophic lateral sclerosis," *J. Neurochem.*, 82:365-374, 2002.

Heyes, "The kynurenine pathway and neurologic disease," *Adv. Exp. Med. Biol.*, 398:125-129, 1996.

Horn et al., "Isolation of a new sulfur-containing amino acid (lanthionine) from sodium carbonate-treated wool," *Journal of Biological Chemistry* 138: 141-149, 1941.

Huang et al., "Dehydroascorbic acid, a blood-brain barrier transportable form of vitamin C, mediates potent cerebroprotection in experimental stroke," *Proc Natl Acad Sci U S A.* 98:11720-4, 2001.

Hyer et al., "Synthetic triterpenoids cooperate with tumor necrosis factor-related apoptosis-inducing ligand to induce apoptosis of breast cancer cells," *Cancer Res.*, 65:4799-4808, 2005.

Jauch et al., "Dysfunction of brain kynurenic acid metabolism in Huntington's disesase: focus on kynurenine aminotransferases," *J. Neurol. Sci.*, 130:39-47, 1995.

Kaltschmidt et al. "Transcription factor NF-κB is activated in primary neurons by amyloid β peptides and in neurons surrounding early plaques from patients with Alzheimer disease," *Proc. Natl. Acad. Sci. USA*, 94:2642-2647, 1997.

Magnuson et al., "The action of quinolinate in the rat spinal cord in vitro," *Can. J. Physiol. Pharm.*, 65:2483-2487, 1987.

Manfredini et al., "Design, synthesis and activity of ascorbic acid prodrugs of nipecotic, kynurenic and diclophenamic acids, liable to increase neurotropic activity," *J. Med. Chem.*, 45:559-562, 2002.

Manfredini et al., "Novel antioxidant agents deriving from molecular combinations of vitamins C and E analogues: 3,4-dihydroxy-5®-[2(R,S)-(6-hydroxy-2,5,7,8-tetramethyl-chroman-2(R,S)-yl-methyl)-[1,3]dioxolan-4(S)-yl]5H-furan-2-one and 3-O-octadecyl derivatives," *Bioorg Med Chem.* 8(12):2791-801, 2000.

Mayer et al., "Characterization of rat LANCL1, a novel member of the lanthionine synthetase C-like protein family, highly expressed in testis and brain," *Gene*, 16:269:73-80, 2001.

Mayer et al., "Molecular characterization and tissue-specific expression of a murine putative G-protein-coupled receptor," *Biochima et Biophys Acta.*, 1399:51-56, 1998.

Mayer et al., "Molecular cloning, characterization, and tissue-specific expression of human LANCL2, a novel member of the LacC-like protein family," *DNA Seq.*, 12:161-166, 2001.

Mayer et al., "Organization and chromosomal localization of the human and mouse genes coding for LanC-like protein 1 (LANCL1)," *Cytogenet. Cell Genet.*, 93:100-104, 2001.

McGeer and McGeer, "The inflammatory response system of brain: implications for therapy of Alzheimer and other neurodegenerative diseases," *Brain Res. Brain Res. Rev.*, 21:195-218, 1995.

Merrill and Benvenist, "Cytokines in inflammatory brain lesions: helpful and harmful," *Trends Neurosci.*, 19:331-338, 1996.

Moroni, "Tryptophan metabolism and brain function: focus on kynurenine and other indole metabolites," *Eur. J. Pharmacol.*, 375:87-100, 1999.

Nakamichi et al., "Protection by exogenous pyruvate through a mechanism related to monocarboxylate transporters against cell death induced by hydrogen peroxide in cultured rat cortical neurons," *J. Neurochem.*, 93:84-93, 2005.

Nardini et al., "Purification and characterization of a ketimine-reducing enzyme," *Eur. J. Biochem.*, 173:689-694, 1988.

Nielson et al., "Germ cell differentiation-dependent and stage-specific expression of LANCL1 in rodent testis," *Eur. J. Histochem.*, 47:215-222, 2003.

Paul et al., "Chemical and enzymatic synthesis of lanthionines," *Mini-Reviews in Organic Chemistry* 2:23-37, 2005.

Probert et al., "Lanthionines for solid phase synthesis," *Tetrahedron Letters* 37:1101-1104, 1996.

Ryu et al., "Blockade of quinolinic acid-induced neurotoxicity by pyruvate is associated with inhibition of glial activation in a model of Huntington's disease," *Exp. Neurol.*, 187:150-159, 2004.

Ryu et al., "Neuroprotective effects of pyruvate in the quinolinic acid rat model of Huntington's disease," *Exp. Neurol.*, 183:700-704, 2003.

Sen et al., "The natural vitamin E to defend the nervous system?" *Ann. NY Acad. Sci.*, 1031:127-142, 2004.

Shao et al., "A facile synthesis of orthogonally protected steroisomeric lanthionines by regioselective ring opening of serine β-Lactone derivatives," *Journal of Organic Chemistry* 60:2956-2957, 1995.

Simonian and Coyle, "Oxidative stress in neurodegenerative diseases," *Annu. Rev. Pharmacol. Toxicol.*, 36:83-106, 1996.

Stone and Darlington, "Endogenous kynurenines as targets for drug discovery and development," *Nat.Reviews Drug Disc.*, 1:609-620, 2002.

Stoy et al., "Tryptophan metabolism and oxidative stress in patients with Huntington's disease," *J. Neurochem.*, 93:611-623; 2005.

Tirosh et al., "Cellular and mitochondrial changes in glutamate-induced HT4 neuronal cell death," *Neurosci.*, 97:531-541, 2000.

Urenjak and Obrenovitch, "Neuroprotective potency of kynurenic acid against excitotoxicity," *NeuroReport*, 11:1341-1344, 2000.

Walker et al., *J. Neuroimmunol.*, 63:163-174, 1995.

West et al., "The arachidonic acid 5-lipoxygenase inhibitor nordihydroguaiaretic acid inhibits tumor necrosis factor α activation of microglia and extends survival of G93A-SOD1 transgenic mice," *J. Neurochem.*, 91:133-143, 2004.

Widner et al., "Tryptophan degradation and immune activation in Alzheimer's disease," *J, Neural, Transm.*, 107:343-353; 2000.

Shankar and Srivastava, "Enhancement of therapeutic potential of TRAIL by cancer chemotherapy and irradiation: mechanisms and clinical implications," *Drug Resistance Updates*, 7:139-156, 2004.

Hermann, "Reaction of halopyruvic acid with thiolamines," *Chemische Berichte*, 94:442-445, 1961.

PCT International Search Report, issued in International Application No. PCT/US2007/060277, dated Jul. 26, 2007.

* cited by examiner

LANTHIONINE-RELATED COMPOUNDS FOR THE TREATMENT OF INFLAMMATORY DISEASES The present application claims benefit of priority to U.S. Provisional Application Ser. Nos. 60/757,252, 60/781,794 and 60/804,149, filed Jan. 9, 2006, Mar. 13, 2006, and Jun. 7, 2006, the entire contents of each of these applications being incorporated by reference herein.

This invention was made with government support under grant numbers AG20783 and NS044154 awarded by the National Institutes of Health and grant number HR02-149RS awarded by the Oklahoma Center for the Advancement of Science and Technology. The government has certain rights in the invention.

BACKGROUND OF THE INVENTION

I. Field of the Invention

The present invention concerns novel lanthionine ketimine compounds, the process of preparing such compounds, and their use. The invention also concerns methods of using lanthionine, pyruvate, lanthionine ketimine, lanthionine ketimine derivatives and combinations of these compounds in the treatment and/or prevention diseases, including diseases affecting the central nervous system.

II. Description of Related Art

The mammalian brain is parsimonious with respect to utilization and salvaging of reduced sulfur (Stryer, 1995). Accordingly, efficient metabolic pathways exist to recycle sulfurous side products of biochemical alkylation reactions (Stryer, 1995; Cooper, 2004). Principal amongst these are the transulfuration pathway (Scheme 1) and the methionine salvage pathway (Stryer 1995; Cooper, 2004; Giulidori et al., 1984). Scheme 1 shows the classical folic acid cycle and transulfuration pathway. The transulfuration pathway is comprised of homocysteine, cystathionine, and downstream products. MS=methionine synthetase; SHM=serine hydroxymethyltransferase; MTR=methylene-THF reductase; CβS=cystathionine β-synthase; CγL=cystathionine γ-lyase; GSH=reduced glutathione; DHF=dihydrofolate; THF=tetrahydrofolate; PC=phosphatidylcholine.

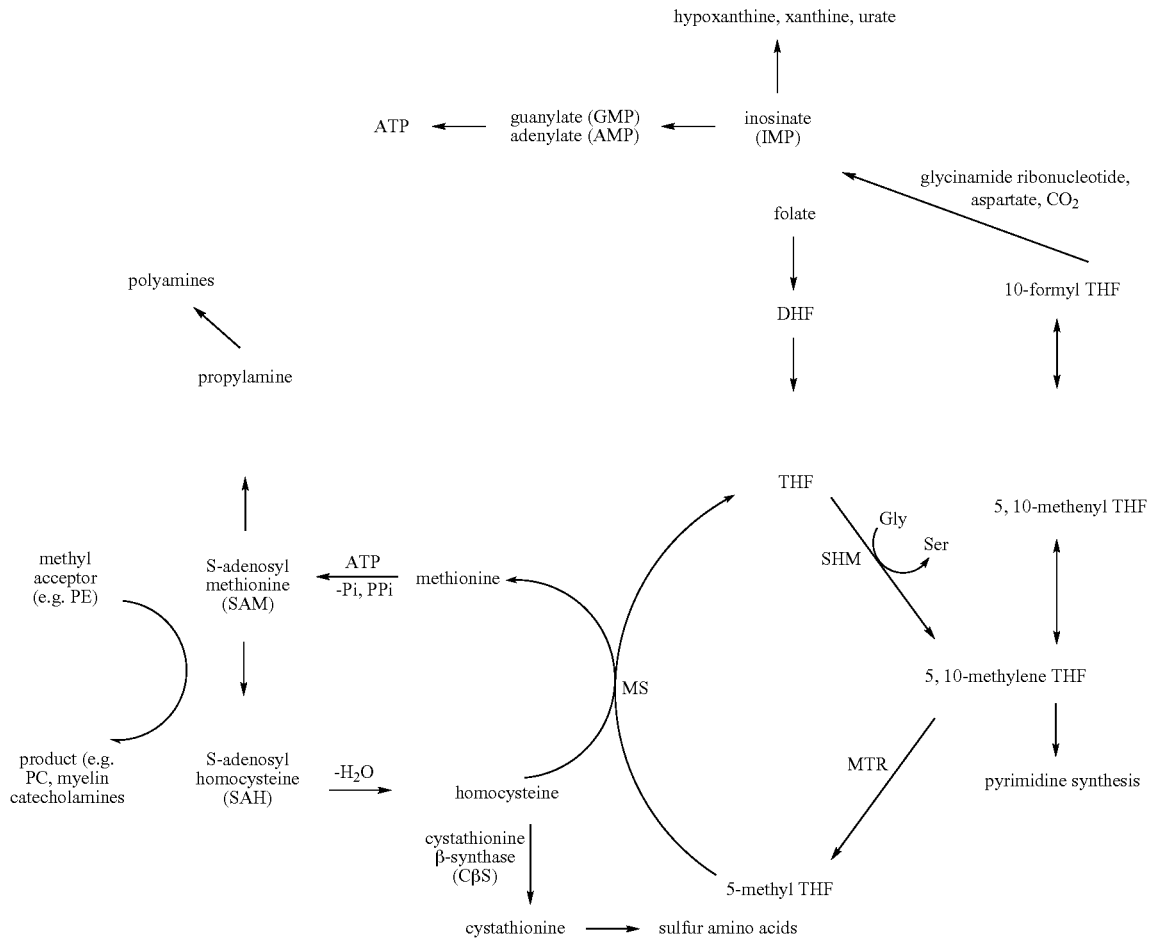

Scheme 1

The transulfuration pathway converts homocysteine (hCys) waste from the folate cycle into the intermediate cystathionine, ultimately regenerating cysteine via the tandem actions of cystathionine β-synthase (CβS) and cystathionine γ-lyase (CγL) (Scheme 1). The methionine salvage pathway (not illustrated in Scheme 1) breaks down S-adenosylthiopropylamine derived from S-adenosyl methionine (SAM) flux into the polyamine pathway (Cooper, 2004; Giulidori et al., 1984).

Despite the metabolic effort expended to prevent sulfur leakage, mammalian brain contains relatively high concentrations of non-canonical sulfurous amino acids such as lanthionine and its derivative lanthionine ketimine (LK) (Cavallini et al., 1983; Cavallini et al., 1985; Fontana et al., 1997; Cavallini et al., 1991; Fontana et al., 1990). Lanthionine, LK, TMDC and analogous compounds derived from cystathionine were discovered and measured in mammalian brain during the 1980s and 1990s by Italian researchers lead by Doriano Cavallini and colleagues (Fontana et al., 1997; Cavallini et al., 1985; Cavallini et al., 1983; Cavallini et al., 1991; Fontana et al., 1990; Cooper, 2004). Cavallini demonstrated that LK in particular could bind synaptosomal membranes with 50 nM affinity (Fontana et al., 1997); however he was unable to demonstrate discrete bioactivities inherent to this unusual sulfurous metabolite.

LK is a cyclic sulfurous thioether; the structure of (R)-LK is shown here:

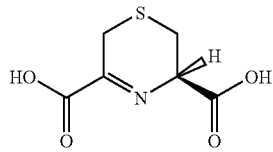

This compound serves no known physiological purpose and are generally considered a waste products of the transsulfuration or methionine salvage pathways. For instance, its precursor, lanthionine, is thought to form during the "misreaction" of CβS (Cooper, 2004). CβS normally condenses serine with hCys (Schemes 1 and 2) but can conjugate serine with cysteine instead. In this case, the product is lanthionine rather than cystathionine (Giulidori et al., 1984; Cavallini et al., 1983). Scheme 2A shows the classical first step of the transulfuration pathway, catalyzed by cystathionine β-synthase (CβS). Scheme 2B shows the alternative reaction which CβS also catalyzes, namely the conjugation of serine (Ser) with cysteine (Cys) yielding lanthionine (αKG refers to alpha ketoglutarate; CγL refers to cystathionine γ-lyase).

Scheme 2

A

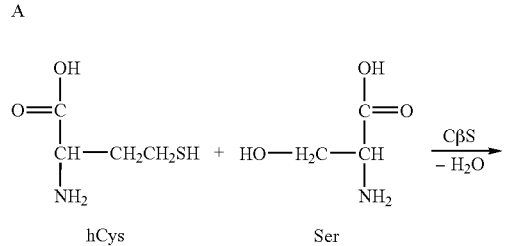

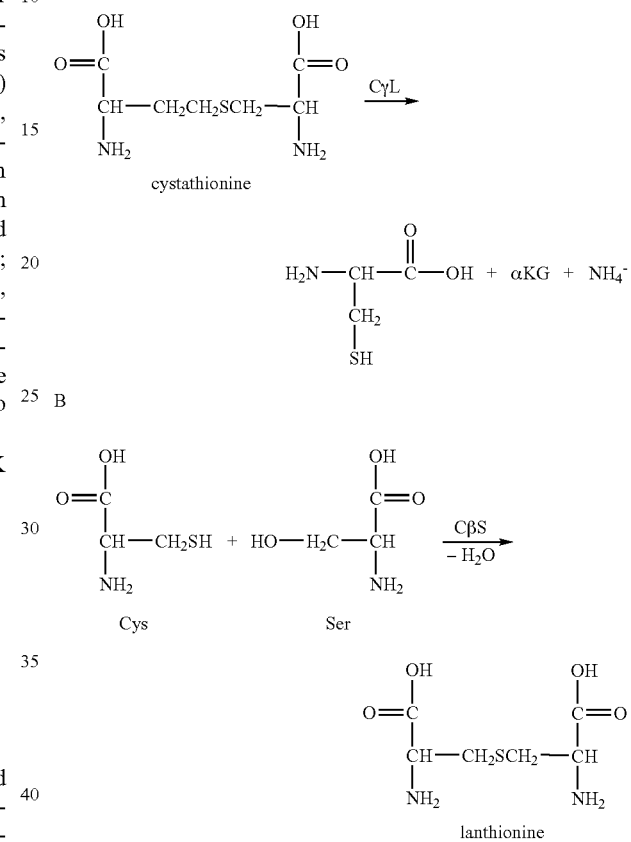

In contrast, lanthionine does not act as a substrate for CγL but instead undergoes enzyme-catalyzed reaction with pyruvate to form LK, a process mediated by kynurenine amino transferase (KAT; also known as glutamine transaminase K (GTK) or cysteine conjugate β-lyase (CCβL)), as shown in Scheme 3 (Giulidori et al., 1984; Cavallini et al., 1983).

Scheme 3

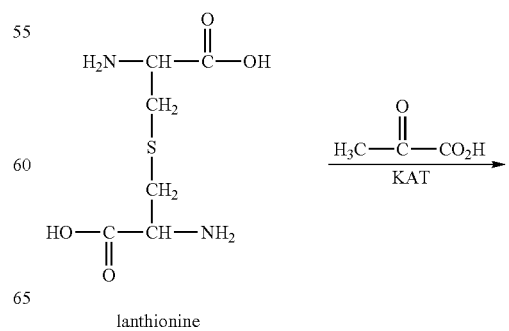

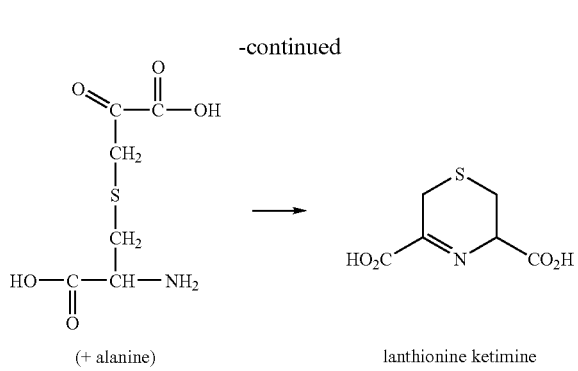

(+ alanine) → lanthionine ketimine

The resulting intermediate rapidly cyclizes to form lanthionine ketimine (Scheme 3). which can be reduced to the corresponding secondary amine, thiomorpholine dicarboxylic acid (TMDC) (Giulidori et al., 1984; Cavallini et al., 1983).

Prior to this invention, Lanthionine ketimine (LK) is a compound for which little or no therapeutic activity had been defined. Determination of biological efficacy of different lanthionine ketimines was not known in the art because no biological function for endogenous LK had been identified. Hence, prior investigators were unable to design a practical quantitative bioassay against which to test the relative efficacy of various LK-based drugs and pro-drugs.

SUMMARY OF THE INVENTION

The present invention overcomes limitations in the prior art by providing novel lanthionine ketimine derivatives and thiomorpholine dicarboxylic acid (TMDCA) derivates, the process of preparing such compounds, and their use. More particularly, it concerns methods of using lanthionine, lanthionine ketimine, lanthionine ketimine derivatives, TMDCA, TMDCA derivatives and combinations of these compounds with other compounds, such as pyruvate, for the treatment and/or prevention diseases, including diseases affecting the central nervous system, such as amyotrophic lateral sclerosis. The invention provides for compounds and methods having anti-oxidant, anti-neuroinflammatory and neuroprotective activities. Furthermore, the invention provides compounds that show anti-proliferative effects and may therefore be useful for the treatments of cancer. In specific embodiments, the invention overcomes the limitations of the prior art by providing lanthionine ketimine derivatives and TMDCA derivatives providing superior delivery of LK and/or TMDCA into a patient by means of esterification and/or amidation. An aspect of the invention is to provide LK derivatives or TMDCA derivatives having the ability to pass through the blood-brain barrier.

An aspect of the present invention relates to a compound having the structure:

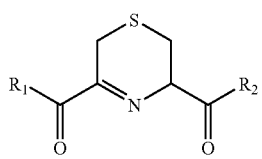

wherein $R_1$ and $R_2$ are each independently —OH, —NH$_2$, or heteroatom substituted or unsubstituted versions of $C_1$-$C_{10}$-alkoxy, $C_2$-$C_{10}$-alkenyloxy, $C_2$-$C_{10}$-alkynyloxy, $C_1$-$C_{10}$-aryloxy, $C_2$-$C_{10}$-aralkoxy, $C_1$-$C_{10}$-acyloxy, $C_1$-$C_{10}$-alkylamino, $C_2$-$C_{10}$-alkenylamino, $C_2$-$C_{10}$-alkynylamino, $C_1$-$C_{10}$-arylamino, $C_2$-$C_{10}$-aralkylamino, or $C_1$-$C_{10}$-amido; provided that $R_1$ and $R_2$ are not both —OH; further provided that if $R_2$ is —OCH$_3$ and $R_1$ is —OH, then the compound is predominantly one enantiomer, and pharmaceutically acceptable salts, hydrates, and optical isomers thereof. For example $R_1$ and/or $R_2$ can be selected from the group consisting of ascorbyl, dehydroascorbate, glycinyl, and serinyl.

The compounds of this invention may have the following chiral structures:

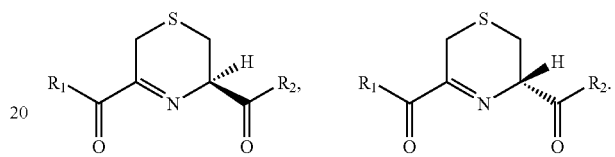

In some of these embodiments, the compound is substantially free from other optical isomers, and pharmaceutically acceptable salts and hydrates thereof. In other embodiments, the compound is a mixture both of the above structures. In certain embodiments, the compound is a racemic mixture.

The following structural formulas provide additional examples of compounds provided by this invention:

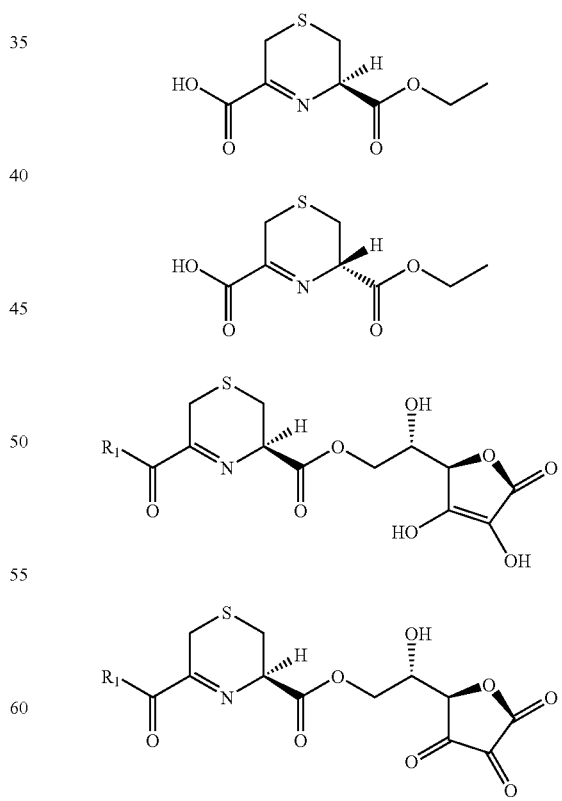

In other embodiments, the present invention provides compounds having the following structure:

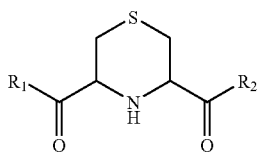

wherein $R_1$ and $R_2$ are each independently —OH, —$NH_2$, or heteroatom substituted or unsubstituted versions of $C_1$-$C_{10}$-alkoxy, $C_2$-$C_{10}$-alkenyloxy, $C_2$-$C_{10}$-alkynyloxy, $C_1$-$C_{10}$-aryloxy, $C_2$-$C_{10}$-aralkoxy, $C_1$-$C_{10}$-acyloxy, $C_1$-$C_{10}$-alkylamino, $C_2$-$C_{10}$-alkenylamino, $C_2$-$C_{10}$-alkynylamino, $C_1$-$C_{10}$-arylamino, $C_2$-$C_{10}$-aralkylamino, or $C_1$-$C_{10}$-amido; provided that $R_1$ and $R_2$ are not both —OH; further provided that if $R_2$ is —$OCH_3$ and $R_1$ is —OH, then the compound is predominantly one enantiomer, and pharmaceutically acceptable salts, hydrates, and optical isomers thereof. In certain embodiments, the $R_1$ and/or $R_2$ is selected from the group consisting of ascorbyl, dehydroascorbate, glycinyl, and serinyl.

The following structures provide additional examples of the compounds provided by this invention:

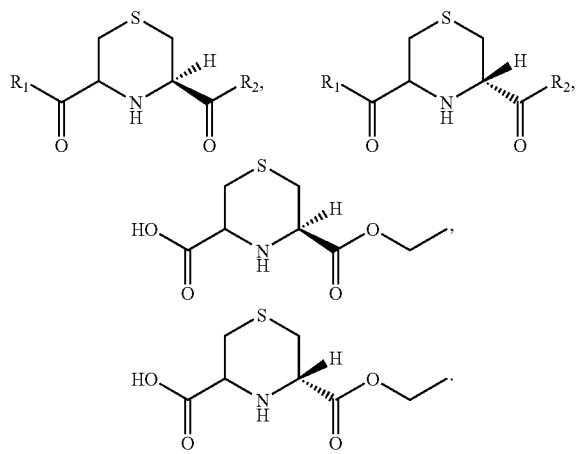

Another aspect of the present invention relates to a method of treating a disease, comprising administering to a subject a pharmacologically effective of lanthionine, lanthionine ketimine (LK), a LK derivative, thiomorpholine dicarboxylic acid (TMDCA), or a TMDCA derivative. The subject may be a mammal (e.g., a human). The method may further comprises administering a second anti-inflammatory compound to the subject, such as a Krebs cycle α-keto acid. The Krebs cycle α-keto acid may be pyruvate or α-ketoglutarate. In certain embodiments where lanthionine is administered to the subject, the method may further comprise administering pyruvate (e.g., from about 25 to about 75 mg/day) and/or α-ketoglutarate to the subject.

The disease may be sepsis and/or an inflammatory disease. The inflammatory disease may be amyotrophic lateral sclerosis (ALS), a degenerative motor neuron disease, Alzheimer's disease, Parkinson's disease, Huntington's disease, multiple sclerosis, macular degeneration, a cardiovascular disease, atherosclerosis, rheumatoid arthritis or inflammatory bowel disease (IBD). The disease may be characterized by deficient KAT/GTK/CCβL activity in the subject. The disease may be hypertension, Huntington's disease, attention deficit disorder, depression (e.g., major depression) or generalized anxiety disorder. In certain embodiments, the disease is characterized by excessive nitric oxide production, excessive glutamate excitotoxicity or excessive prostaglandin E2 (PGE2) in the subject. The disease may be characterized by activated macrophage cells and/or activated microglia cells in the subject.

Another aspect of the present invention relates to a method for evaluating the effectiveness of an LK derivative for the treatment of an inflammatory diseases, wherein the method comprises contacting the LK derivative with a macrophage cell, and measuring the response of the macrophage cell to an inflammatory stimulus. The macrophage cell may be a microglial cell. The inflammatory stimulus may be a pro-inflammatory cytokine, such as TNFα or IFNγ. Nitric oxide production from the macrophage cell may be evaluated. The evaluation may comprise measuring nitrite production from the macrophage cell.

Another aspect of the present invention relates to a method of reducing damage to a cell resulting from excitotoxicity or free radical toxicity, wherein a compound of the present invention is contacted with the cell, wherein the cell is a neuron, a macrophage or a glial cell, and wherein the glial cell is not a glioma cell. The glial cell may be an astroglia cell or a microglial cell. The neuron may be a motoneuron.

In certain embodiments, the invention provides a method of reducing damage to a cell resulting from oxidative stress, wherein the compound of claim the present invention is contacted with the cell, wherein the cell is a neuron, a macrophage or a glial cell, and wherein the glial cell is not a glioma cell. In further embodiments, the invention provides a method of reducing damage to a cell resulting from excitatory amino acid toxicity, wherein the compound of the present invention is contacted with the cell, wherein the cell is a neuron, a macrophage or a glial cell, and wherein the glial cell is not a glioma cell. In some of these embodiments, the oxidative stress is without excitatory amino acid toxicity. In other embodiments, the excitatory amino acid toxicity is without oxidative stress. In some embodiments, the oxidative stress don't involve free radicals. For example, both hypochlorite and hydrogen peroxide can oxidize substrates through non-radical mechanisms. In certain embodiments, the excitatory amino acid toxicity is glutamate-induced excitotoxicity.

In certain embodiments, the method further comprises contacting the cell with a second anti-inflammatory compound. The second anti-inflammatory compound may be a Krebs cycle α-keto acid, such as pyruvate or α-ketoglutarate. The free radical toxicity may result from nitric oxide. The cell may be present in a subject (e.g., a human patient).

The invention also discloses a method of treating a patient having an inflammatory disease, comprising administering a therapeutically effective amount of a compound of this invention, such as those described above or throughout this specification. In some embodiments, the inflammatory disease is rheumatoid arthritis, or inflammatory bowel disease. In some embodiments, the compound is optically pure. For example, in some embodiments, the compound is predominantly the (+) enantiomer. In other embodiments, the compound is predominantly the (−) enantiomer. In other embodiments, the compound is a racemic mixture. In certain embodiments, the compound is administered with an aqueous solution. In some embodiments, the therapeutically effective amount is 0.1-1000 mg/kg. In further embodiments, an additional agent is administered to said patient.

The invention also discloses a method of treating a patient having a neurodegenerative disease, comprising administering a therapeutically effective amount of a compound of this invention, such as those described above or throughout this specification. In some embodiments, the neurodegenerative disease is Alzheimer's disease, Parkinson's disease, multiple sclerosis or amyotrophic lateral sclerosis. In some embodiments, the compound is optically pure. For example, in some embodiments, the compound is predominantly the (+) enantiomer. In other embodiments, the compound is predominantly the (−) enantiomer. In other embodiments, the compound is a racemic mixture. In certain embodiments, the compound is administered with an aqueous solution. In some embodiments, the therapeutically effective amount is 0.1-1000 mg/kg. In further embodiments, an additional agent is administered to said patient.

The invention also discloses a method of treating a patient having a pathogenesis involving the excessive production of nitric oxide or prostaglandins, comprising administering a therapeutically effective amount of a compound of this invention, such as those described above or throughout this specification. In some embodiments, the compound is optically pure. For example, in some embodiments, the compound is predominantly the (+) enantiomer. In other embodiments, the compound is predominantly the (−) enantiomer. In other embodiments, the compound is a racemic mixture. In certain embodiments, the compound is administered with an aqueous solution. In some embodiments, the therapeutically effective amount is 0.1-1000 mg/kg. In further embodiments, an additional agent is administered to said patient. In certain embodiments, the prostaglandins are inflammatory prostaglandins.

The invention also discloses a method of treating a patient having a disorder characterized by the overexpression of iNOS or COX-2 gene, comprising administering a therapeutically effective amount of a compound of this invention, such as those described above or throughout this specification. In some embodiments, the compound is optically pure. For example, in some embodiments, the compound is predominantly the (+) enantiomer. In other embodiments, the compound is predominantly the (−) enantiomer. In other embodiments, the compound is a racemic mixture. In certain embodiments, the compound is administered with an aqueous solution. In some embodiments, the therapeutically effective amount is 0.1-1000 mg/kg. In further embodiments, an additional agent is administered to said patient.

The invention also discloses a method of modulating transcription or translation of iNOS or COX-2 genes in a patient, comprising administering a therapeutically effective amount of a compound of this invention, such as those described above or throughout this specification. In some embodiments, the compound is optically pure. For example, in some embodiments, the compound is predominantly the (+) enantiomer. In other embodiments, the compound is predominantly the (−) enantiomer. In other embodiments, the compound is a racemic mixture. In certain embodiments, the compound is administered with an aqueous solution. In some embodiments, the therapeutically effective amount is 0.1-1000 mg/kg. In further embodiments, an additional agent is administered to said patient.

The invention also discloses a method of modulating excessive nitric oxide or prostaglandin formation in a patient, comprising administering a therapeutically effective amount of a compound of this invention, such as those described above or throughout this specification. In some embodiments, the compound is optically pure. For example, in some embodiments, the compound is predominantly the (+) enantiomer. In other embodiments, the compound is predominantly the (−) enantiomer. In other embodiments, the compound is a racemic mixture. In certain embodiments, the compound is administered with an aqueous solution. In some embodiments, the therapeutically effective amount is 0.1-1000 mg/kg. In further embodiments, an additional agent is administered to said patient. In certain embodiments, the formation of inflammatory prostaglandins may be modulated.

The invention also provides a method of treating a subject at risk for having a stroke, comprising administering to the subject a pharmacologically effective amount of lanthionine, lanthionine ketimine (LK), a LK derivative, thiomorpholine dicarboxylic acid (TMDCA), or a TMDCA derivative. In certain embodiments, the subject is a human patient.

The invention also provides a method of treating a subject for a stroke, comprising administering to the subject a pharmacologically effective amount of lanthionine, lanthionine ketimine (LK), a LK derivative, thiomorpholine dicarboxylic acid (TMDCA), or a TMDCA derivative. In certain embodiments, the subject is a human patient. In certain embodiments, the invention provides a treatments for stroke and stroke-related complications after the event of stroke or other stoppage of blood flow to the brain (e.g. in case of heart failure).

The invention also provides a method of treating a patient having cancer, comprising administering a therapeutically effective amount of lanthionine, lanthionine ketimine (LK), a LK derivative, thiomorpholine dicarboxylic acid (TMDCA), or a TMDCA derivative. In certain embodiments, the cancer is brain, lung, liver, spleen, kidney, lymph node, small intestine, pancreas, blood cell, bone, colon, stomach, bread, endometrium, prostate, testicle, ovary, central nervous system, skin, head and neck, esophagus, or bone marrow cancer.

The terms "inhibiting," "reducing," or "prevention," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions of the invention can be used to achieve methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A: EOC-20 cells were pretreated with either LK or (R)-LKE1 thirty minutes before challenge with TNFα. $NO_2^-$ and viability were measured 24 h later as described in the text. Bars indicate mean±SD, N=4, 2 $cm^2$ cell culture wells in a representative experiment. *P<0.05 relative to positive control; † P<0.05 relative to LK-treated group. FIG. 1B: Dose-response inhibition of microglial activation by (R)-LKE1. Error bars indicate mean±SD, N=4 wells from a typical experiment. *p<0.05; **p<0.01 by two-tailed t-test. "LKE" refers to (R)-LKE1.

FIG. 9A. LKE inhibits LPS-stimulated activation of EOC-20 microglia. EOC-20 cells were pretreated with either LK or (R)-LKE1 30 minutes before challenge with TNFα. $NO_2^-$ and viability were measured after 24 hours of later. FIG. 9B: Dose response for (R)-LKE1 on LPS-stimulated $NO_2^-$ production in RAW 264.7 macrophages. Nitrite concentration was measured 24 hours and 48 hours after stimulation with LPS.

LDH activity of detached cells+LDH activity in the cell culture media. "LKE" refers to (R)-LKE1; "con" refers to control, and "G" refers to glutamate control.

Figure 15:
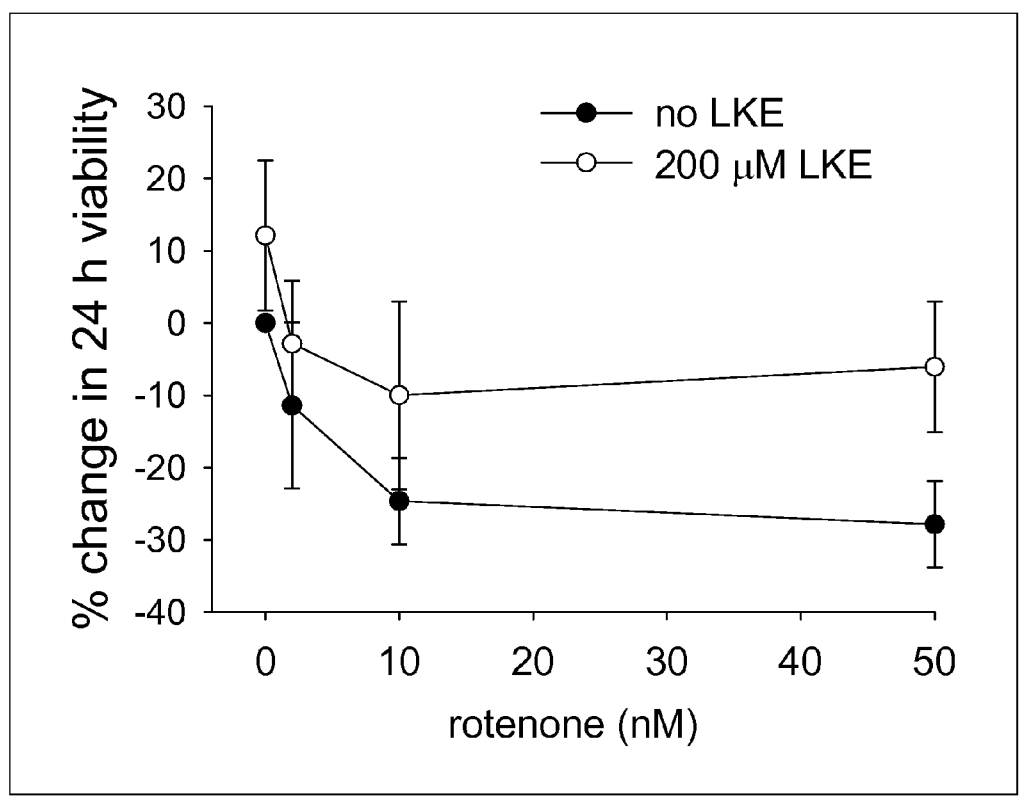

FIG. 15. (R)-LKE1 protects SHSY5Y dopaminergic neuroblastoma cells against rotenone toxicity. In this experiment SHSY5Y cultures were treated with (R)-LKE1 for 30 min. prior to addition of rotenone, then assayed for viability at various later time points. The percent change in 24 hour cell viability was measured in the presence and absence of (R)-LKE1 at difference rotenone concentrations. "LKE" refers to (R)-LKE1.

Figure 16:
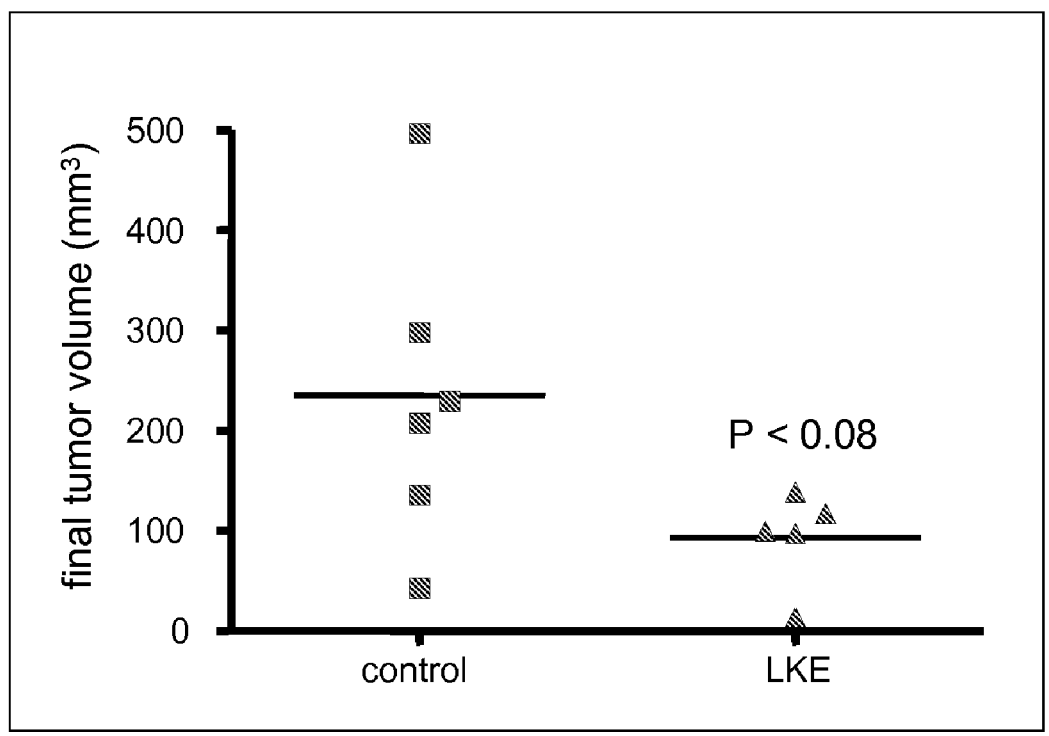

FIG. 16. (R)-LKE1 inhibits tumor cell proliferation. 100,000 C6 glioma cells were implanted in the neocortex of adult male Sprague-Dawley rats. The test group was administered (R)-LKE1 in saline 100 mg/day at each of 7 days/week starting the day of implantation. The control group did not receive the (R)-LKE1 treatment.

Figure 17:
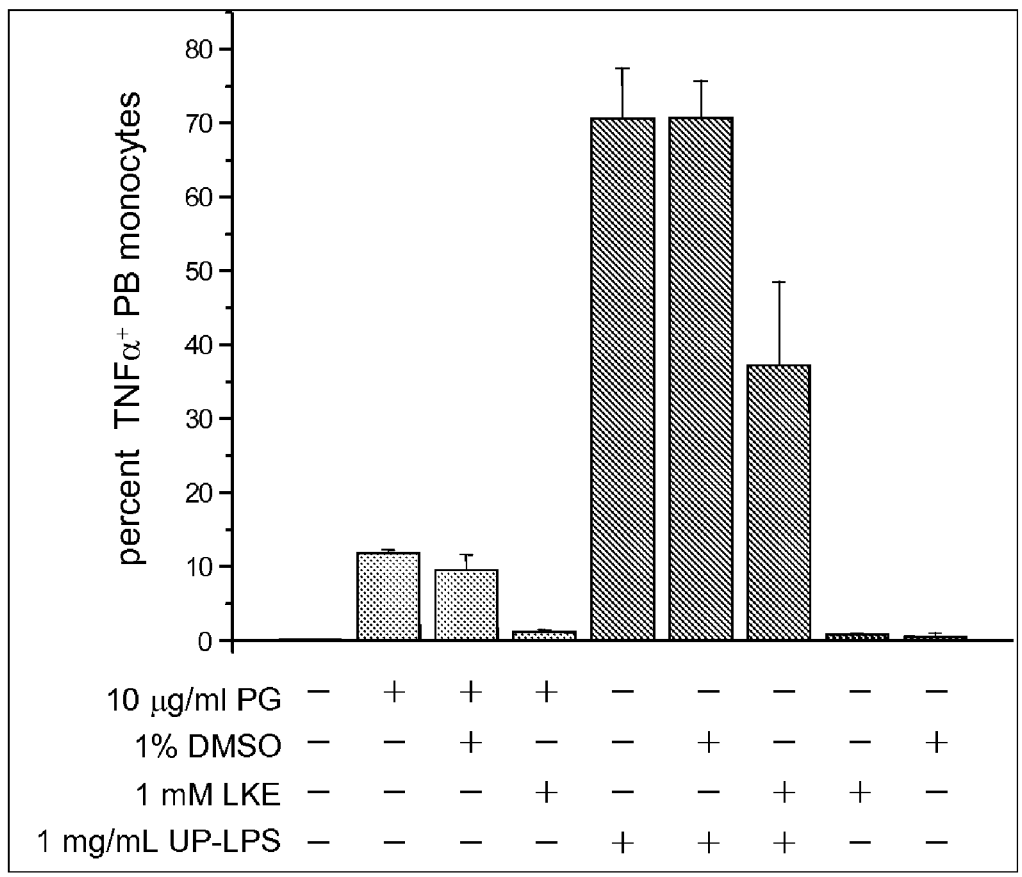

FIG. 17. LKE inhibits TNFα produced in human PB monocytes stimulated with PGN and UPLPS. PB was preincubated with 1 mM (R)-LKE1 or diluent 1% DMSO and subsequently stimulated with PGN or UPLPS. The number of CD14+ monocytes that were positive for intracellular TNFα was measured by intracellular staining and flow cytometry. Data=mean+/−standard error, N=2 biological replicates. "LKE" refers to (R)-LKE1.

DESCRIPTION OF ILLUSTRATIVE EMBODIMENTS

I. The Present Invention

The present invention overcomes limitations in the prior art by providing novel lanthionine ketimine derivatives, as well as processes for the preparation of such compounds. The invention also concerns the use of lanthionine, lanthionine ketimine (LK), a LK derivative, thiomorpholine dicarboxylic acid (TMDCA), a TMDCA derivative, and/or combinations of these compounds with other compounds, such as pyruvate, for the treatment and/or prevention diseases, including diseases affecting the central nervous system such as amyotrophic lateral sclerosis. For example, the invention provides for compounds and methods having anti-oxidant, anti-neuroinflammatory and neuroprotective activities. It also provides for compounds having the ability to pass through and/or be transported through cellular membranes, such the blood-brain barrier (BBB). Furthermore, the invention provides compounds that show anti-proliferative effects and may therefore be useful for the treatments of cancer.

The practice of the present invention will employ, unless otherwise indicated, conventional techniques of cell biology, cell culture, molecular biology, microbiology, recombinant DNA, medicine, pharmacology and immunology, which are within the skill of the art. Such techniques are explained fully in the literature. See, for example, Sambrook et al., 1989; Ausubel et al., 1994; Glover, 1985; Gait, 1984; U.S. Pat. No. 4,683,195; Hames and Higgins, 1985; Mayer and Walker, 1988; Weir and Blackwell, 1986.

II. Definitions

The terms "inhibiting," "reducing," or "prevention," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an," when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions of the invention can be used to achieve methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the term "amino" means $-NH_2$; the term "nitro" means $-NO_2$; the term "halo" designates $-F$, $-Cl$, $-Br$ or $-I$; the term "mercapto" means $-SH$; the term "cyano" means $-CN$; the term "silyl" means $-SiH_3$, and the term "hydroxy" means $-OH$.

The term "heteroatom-substituted," when used to modify a class of organic radicals (e.g. alkyl, aryl, acyl, etc.), means that one, or more than one, hydrogen atom of that radical has been replaced by a heteroatom, or a heteroatom containing group. Examples of heteroatoms and heteroatom containing groups include: hydroxy, cyano, alkoxy, $=O$, $=S$, $-NO_2$, $-N(CH_3)_2$, amino, or $-SH$. Specific heteroatom-substituted organic radicals are defined more fully below.

The term "heteroatom-unsubstituted," when used to modify a class of organic radicals (e.g. alkyl, aryl, acyl, etc.) means that none of the hydrogen atoms of that radical have been replaced with a heteroatom or a heteroatom containing group. Substitution of a hydrogen atom with a carbon atom, or a group consisting of only carbon and hydrogen atoms, is not sufficient to make a group heteroatom-substituted. For example, the group $-C_6H_4C\equiv CH$ is an example of a heteroatom-unsubstituted aryl group, while $-C_6H_4F$ is an example of a heteroatom-substituted aryl group. Specific heteroatom-unsubstituted organic radicals are defined more fully below.

The term "heteroatom-unsubstituted $C_n$-alkyl" refers to a radical, having a linear or branched, cyclic or acyclic structure, further having no carbon-carbon double or triple bonds, further having a total of n carbon atoms, all of which are nonaromatic, 3 or more hydrogen atoms, and no heteroatoms. For example, a heteroatom-unsubstituted $C_1$-$C_{10}$-alkyl has 1 to 10 carbon atoms. The term "alkyl" includes straight-chain alkyl groups, branched-chain alkyl groups, cycloalkyl (alicyclic) groups, alkyl heteroatom-substituted cycloalkyl groups, and cycloalkyl heteroatom-substituted alkyl groups. The groups, $-CH_3$, $-CH_2CH_3$, $-CH_2CH_2CH_3$, $-CH(CH_3)_2$, $-CH(CH_2)_2$, $-CH_2CH_2CH_2CH_3$, $-CH(CH_3)CH_2CH_3$, $-CH_2CH(CH_3)_2$, $-C(CH_3)_3$, $-CH_2C(CH_3)_3$, cyclopentyl, and cyclohexyl, are all examples of heteroatom-unsubstituted alkyl groups.

The term "heteroatom-substituted $C_n$-alkyl" refers to a radical, having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted $C_1$-$C_{10}$-alkyl has 1 to 10 carbon atoms. The following groups are all examples of heteroatom-substituted alkyl groups: trifluoromethyl, —$CH_2F$, —$CH_2Cl$, —$CH_2Br$, —$CH_2OH$, —$CH_2OCH_3$, —$CH_2OCH_2CH_3$, —$CH_2OCH_2CH_2CH_3$, —$CH_2OCH(CH_3)_2$, —$CH_2OCH(CH_2)_2$, —$CH_2OCH_2CF_3$, —$CH_2OCOCH_3$, —$CH_2NH_2$, —$CH_2NHCH_3$, —$CH_2N(CH_3)_2$, —$CH_2NHCH_2CH_3$, —$CH_2N(CH_3)CH_2CH_3$, —$CH_2NHCH_2CH_2CH_3$, —$CH_2NHCH(CH_3)_2$, —$CH_2NHCH(CH_2)_2$, —$CH_2N(CH_2CH_3)_2$, —$CH_2CH_2F$, —$CH_2CH_2Cl$, —$CH_2CH_2Br$, —$CH_2CH_2I$, —$CH_2CH_2OH$, $CH_2CH_2OCOCH_3$, —$CH_2CH_2NH_2$, —$CH_2CH_2N(CH_3)_2$, —$CH_2CH_2NHCH_2CH_3$, —$CH_2CH_2N(CH_3)CH_2CH_3$, —$CH_2CH_2NHCH_2CH_2CH_3$, —$CH_2CH_2NHCH(CH_3)_2$, —$CH_2CH_2NHCH(CH_2)_2$, —$CH_2CH_2N(CH_2CH_3)_2$, —$CH_2CH_2NHCO_2C(CH_3)_3$, and —$CH_2Si(CH_3)_3$.

The term "heteroatom-unsubstituted $C_n$-alkenyl" refers to a radical, having a linear or branched, cyclic or acyclic structure, further having at least one nonaromatic carbon-carbon double bond, but no carbon-carbon triple bonds, a total of n carbon atoms, three or more hydrogen atoms, and no heteroatoms. For example, a heteroatom-unsubstituted $C_2$-$C_{10}$-alkenyl has 2 to 10 carbon atoms. Heteroatom-unsubstituted alkenyl groups include: —$CH=CH_2$, —$CH=CHCH_3$, —$CH=CHCH_2CH_3$, —$CH=CHCH_2CH_2CH_3$, —$CH=CHCH(CH_3)_2$, —$CH=CHCH(CH_2)_2$, —$CH_2CH=CH_2$, —$CH_2CH=CHCH_3$, —$CH_2CH=CHCH_2CH_3$, —$CH_2CH=CHCH_2CH_2CH_3$, —$CH_2CH=CHCH(CH_3)_2$, —$CH_2CH=CHCH(CH_2)_2$, and —$CH=CH—C_6H_5$.

The term "heteroatom-substituted $C_n$-alkenyl" refers to a radical, having a single nonaromatic carbon atom as the point of attachment and at least one nonaromatic carbon-carbon double bond, but no carbon-carbon triple bonds, further having a linear or branched, cyclic or acyclic structure, further having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted $C_2$-$C_{10}$-alkenyl has 2 to 10 carbon atoms. The groups, —$CH=CHF$, —$CH=CHCl$ and —$CH=CHBr$, are examples of heteroatom-substituted alkenyl groups.

The term "heteroatom-unsubstituted $C_n$-alkynyl" refers to a radical, having a linear or branched, cyclic or acyclic structure, further having at least one carbon-carbon triple bond, a total of n carbon atoms, at least one hydrogen atom, and no heteroatoms. For example, a heteroatom-unsubstituted $C_2$-$C_{10}$-alkynyl has 2 to 10 carbon atoms. The groups, —$C≡CH$, —$C≡CCH_3$, and —$C≡CC_6H_5$ are examples of heteroatom-unsubstituted alkynyl groups.

The term "heteroatom-substituted $C_n$-alkynyl" refers to a radical, having a single nonaromatic carbon atom as the point of attachment and at least one carbon-carbon triple bond, further having a linear or branched, cyclic or acyclic structure, and having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted $C_2$-$C_{10}$-alkynyl has 2 to 10 carbon atoms. The group, —$C≡CSi(CH_3)_3$, is an example of a heteroatom-substituted alkynyl group.

The term "heteroatom-unsubstituted $C_n$-aryl" refers to a radical, having a single carbon atom as a point of attachment, wherein the carbon atom is part of an aromatic ring structure containing only carbon atoms, further having a total of n carbon atoms, 5 or more hydrogen atoms, and no heteroatoms. For example, a heteroatom-unsubstituted $C_6$-$C_{10}$-aryl has 6 to 10 carbon atoms. Examples of heteroatom-unsubstituted aryl groups include phenyl, methylphenyl, (dimethyl)phenyl, —$C_6H_4CH_2CH_3$, —$C_6H_4CH_2CH_2CH_3$, —$C_6H_4CH(CH_3)_2$, —$C_6H_4CH(CH_2)_2$, —$C_6H_3(CH_3)CH_2CH_3$, —$C_6H_4CH=CH_2$, —$C_6H_4CH=CHCH_3$, —$C_6H_4C≡CH$, —$C_6H_4C≡CCH_3$, naphthyl, quinolyl, indolyl, and the radical derived from biphenyl. The term "heteroatom-unsubstituted aryl" includes carbocyclic aryl groups, biaryl groups, and radicals derived from polycyclic fused hydrocarbons (PAHs).

The term "heteroatom-substituted $C_n$-aryl" refers to a radical, refers to a radical, having either a single aromatic carbon atom or a single aromatic heteroatom as the point of attachment, further having a total of n carbon atoms, at least one hydrogen atom, and at least one heteroatom, further wherein each heteroatom is independently selected from the group consisting of N, O, F, Cl, Br, I, Si, P, and S. For example, a heteroatom-unsubstituted $C_1$-$C_{10}$-heteroaryl has 1 to 10 carbon atoms. The term "heteroatom-substituted aryl" includes heteroaryl and heterocyclic aryl groups. It also includes those groups derived from the compounds: pyrrole, furan, thiophene, imidazole, oxazole, isoxazole, thiazole, isothiazole, triazole, pyrazole, pyridine, pyrazine, pyridazine, pyrimidine, and the like. Further examples of heteroatom-substituted aryl groups include the groups: —$C_6H_4F$, —$C_6H_4Cl$, —$C_6H_4Br$, —$C_6H_4I$, —$C_6H_4OH$, —$C_6H_4OCH_3$, —$C_6H_4OCH_2CH_3$, —$C_6H_4OCOCH_3$, —$C_6H_4OC_6H_5$, —$C_6H_4NH_2$, —$C_6H_4NHCH_3$, —$C_6H_4NHCH_2CH_3$, —$C_6H_4CH_2Cl$, —$C_6H_4CH_2Br$, —$C_6H_4CH_2OH$, —$C_6H_4CH_2OCOCH_3$, —$C_6H_4CH_2NH_2$, —$C_6H_4N(CH_3)_2$, —$C_6H_4CH_2CH_2Cl$, —$C_6H_4CH_2CH_2OH$, —$C_6H_4CH_2CH_2OCOCH_3$, —$C_6H_4CH_2CH_2NH_2$, —$C_6H_4CH_2CH=CH_2$, —$C_6H_4CF_3$, —$C_6H_4CN$, —$C_6H_4C≡CSi(CH_3)_3$, —$C_6H_4COH$, —$C_6H_4COCH_3$, —$C_6H_4COCH_2CH_3$, —$C_6H_4COCH_2CF_3$, —$C_6H_4COC_6H_5$, —$C_6H_4CO_2H$, —$C_6H_4CO_2CH_3$, —$C_6H_4CONH_2$, —$C_6H_4CONHCH_3$, —$C_6H_4CON(CH_3)_2$, furanyl, thienyl, pyridyl, pyrrolyl, pyrimidyl, pyrazinyl, and imidazoyl.

The term "heteroatom-unsubstituted $C_n$-aralkyl" refers to a radical, having a single saturated carbon atom as the point of attachment, further having a total of n carbon atoms, wherein at least 6 of the carbon atoms form an aromatic ring structure containing only carbon atoms, 7 or more hydrogen atoms, and no heteroatoms. For example, a heteroatom-unsubstituted $C_7$-$C_{10}$-aralkyl has 7 to 10 carbon atoms. An "aralkyl" includes an alkyl heteroatom-substituted with an aryl group. Examples of heteroatom-unsubstituted aralkyls include phenylmethyl (benzyl) and phenylethyl.

The term "heteroatom-substituted $C_n$-aralkyl" refers to a radical, having a single saturated carbon atom as the point of attachment, further having a total of n carbon atoms, 0, 1, or more than one hydrogen atom, and at least one heteroatom, wherein at least one of the carbon atoms is incorporated an aromatic ring structures, further wherein each heteroatom is independently selected from the group consisting of N, O, F, Cl, Br, I, Si, P, and S. For example, a heteroatom-substituted $C_2$-$C_{10}$-heteroaralkyl has 2 to 10 carbon atoms.

The term "heteroatom-unsubstituted $C_n$-acyl" refers to a radical, having a single carbon atom of a carbonyl group as the point of attachment, further having a linear or branched, cyclic or acyclic structure, further having a total of n carbon atoms, 1 or more hydrogen atoms, a total of one oxygen atom, and no additional heteroatoms. For example, a heteroatom-unsubstituted $C_1$-$C_{10}$-acyl has 1 to 10 carbon atoms. The groups, —COH, —COCH$_3$, —COCH$_2$CH$_3$, —COCH$_2$CH$_2$CH$_3$, —COCH(CH$_3$)$_2$, —COCH(CH$_2$)$_2$, —COC$_6$H$_5$, —COC$_6$H$_4$CH$_3$, —COC$_6$H$_4$CH$_2$CH$_3$, —COC$_6$H$_4$CH$_2$CH$_2$CH$_3$, —COC$_6$H$_4$CH(CH$_3$)$_2$, —COC$_6$H$_4$CH(CH$_2$)$_2$, and —COC$_6$H$_3$(CH$_3$)$_2$, are examples of heteroatom-unsubstituted acyl groups.

The term "heteroatom-substituted $C_n$-acyl" refers to a radical, having a single carbon atom as the point of attachment, the carbon atom being part of a carbonyl group, further having a linear or branched, cyclic or acyclic structure, further having a total of n carbon atoms, 0, 1, or more than one hydrogen atom, at least one additional heteroatom in addition to the oxygen of the carbonyl group, wherein each additional heteroatom is independently selected from the group consisting of N, O F, Cl, Br, I, Si, P, and S. For example, a heteroatom-substituted $C_1$-$C_{10}$-acyl has 1 to 10 carbon atoms. The term heteroatom-substituted acyl includes carbamoyl, thiocarboxylate, and thiocarboxylic acid groups. The groups, —COCH$_2$CF$_3$, —CO$_2$H, —CO$_2$CH$_3$, —CO$_2$CH$_2$CH$_3$, —CO$_2$CH$_2$CH$_2$CH$_3$, —CO$_2$CH(CH$_3$)$_2$, —CO$_2$CH(CH$_2$)$_2$, —CONH$_2$, —CONHCH$_3$, —CONHCH$_2$CH$_3$, —CONHCH$_2$CH$_2$CH$_3$, —CONHCH(CH$_3$)$_2$, —CONHCH(CH$_2$)$_2$, —CON(CH$_3$)$_2$, —CON(CH$_2$CH$_3$)CH$_3$, —CON(CH$_2$CH$_3$)$_2$ and —CONHCH$_2$CF$_3$, are examples heteroatom-substituted acyl groups.

The term "heteroatom-unsubstituted $C_n$-alkoxy" refers to a group, having the structure —OR, in which R is a heteroatom-unsubstituted $C_n$-alkyl, as that term is defined above. Heteroatom-unsubstituted alkoxy groups include: —OCH$_3$, —OCH$_2$CH$_3$, —OCH$_2$CH$_2$CH$_3$, —OCH(CH$_3$)$_2$, and —OCH(CH$_2$)$_2$.

The term "heteroatom-substituted $C_n$-alkoxy" refers to a group, having the structure —OR, in which R is a heteroatom-substituted $C_n$-alkyl, as that term is defined above. For example, —OCH$_2$CF$_3$ is a heteroatom-substituted alkoxy group.

The term "heteroatom-unsubstituted $C_n$-alkenyloxy" refers to a group, having the structure —OR, in which R is a heteroatom-unsubstituted $C_n$-alkenyl, as that term is defined above.

The term "heteroatom-substituted $C_n$-alkenyloxy" refers to a group, having the structure —OR, in which R is a heteroatom-substituted $C_n$-alkenyl, as that term is defined above.

The term "heteroatom-unsubstituted $C_n$-alkynyloxy" refers to a group, having the structure —OR, in which R is a heteroatom-unsubstituted $C_n$-alkynyl, as that term is defined above.

The term "heteroatom-substituted $C_n$-alkynyloxy" refers to a group, having the structure —OR, in which R is a heteroatom-substituted $C_n$-alkynyl, as that term is defined above.

The term "heteroatom-unsubstituted $C_n$-aryloxy" refers to a group, having the structure —OAr, in which Ar is a heteroatom-unsubstituted $C_n$-aryl, as that term is defined above. An example of a heteroatom-unsubstituted aryloxy group is —OC$_6$H$_5$.

The term "heteroatom-substituted $C_n$-aryloxy" refers to a group, having the structure —OAr, in which Ar is a heteroatom-substituted $C_n$-aryl, as that term is defined above.

The term "heteroatom-unsubstituted $C_n$-aralkyloxy" refers to a group, having the structure —OAr, in which Ar is a heteroatom-unsubstituted $C_n$-aralkyl, as that term is defined above.

The term "heteroatom-substituted $C_n$-aralkyloxy" refers to a group, having the structure —OAr, in which Ar is a heteroatom-substituted $C_n$-aralkyl, as that term is defined above.

The term "heteroatom-unsubstituted $C_n$-acyloxy" refers to a group, having the structure —OAc, in which Ac is a heteroatom-unsubstituted $C_n$-acyl, as that term is defined above. A heteroatom-unsubstituted acyloxy group includes alkylcarbonyloxy and arylcarbonyloxy groups. For example, —OCOCH$_3$ is an example of a heteroatom-unsubstituted acyloxy group.

The term "heteroatom-substituted $C_n$-acyloxy" refers to a group, having the structure —OAc, in which Ac is a heteroatom-substituted $C_n$-acyl, as that term is defined above. A heteroatom-substituted acyloxy group includes alkoxycarbonyloxy, aryloxycarbonyloxy, carboxylate, alkylcarbonyl, alkoxycarbonyl, aminocarbonyl, and alkylthiocarbonyl groups.

The term "heteroatom-unsubstituted $C_n$-alkylamino" refers to a radical, having a single nitrogen atom as the point of attachment, further having one or two saturated carbon atoms attached to the nitrogen atom, further having a linear or branched, cyclic or acyclic structure, containing a total of n carbon atoms, all of which are nonaromatic, 4 or more hydrogen atoms, a total of 1 nitrogen atom, and no additional heteroatoms. For example, a heteroatom-unsubstituted $C_1$-$C_{10}$-alkylamino has 1 to 10 carbon atoms. The term "heteroatom-unsubstituted $C_n$-alkylamino" includes groups, having the structure —NHR, in which R is a heteroatom-unsubstituted $C_n$-alkyl, as that term is defined above. A heteroatom-unsubstituted alkylamino group would include —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_3$, —NHCH(CH$_3$)CH$_2$CH$_3$, —NHCH$_2$CH(CH$_3$)$_2$, —NHC(CH$_3$)$_3$, —N(CH$_3$)$_2$, —N(CH$_3$)CH$_2$CH$_3$, —N(CH$_2$CH$_3$)$_2$, N-pyrrolidinyl, and N-piperidinyl.

The term "heteroatom-substituted $C_n$-alkylamino" refers to a radical, having a single nitrogen atom as the point of attachment, further having one or two saturated carbon atoms attached to the nitrogen atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_1$-$C_{10}$-alkylamino has 1 to 10 carbon atoms. The term "heteroatom-substituted $C_n$-alkylamino" includes groups, having the structure —NHR, in which R is a heteroatom-substituted $C_n$-alkyl, as that term is defined above.

The term "heteroatom-unsubstituted $C_n$-alkenylamino" refers to a radical, having a single nitrogen atom as the point of attachment, further having one or two carbon atoms attached to the nitrogen atom, further having a linear or branched, cyclic or acyclic structure, containing at least one nonaromatic carbon-carbon double bond, a total of n carbon atoms, 4 or more hydrogen atoms, a total of one nitrogen atom, and no additional heteroatoms. For example, a heteroatom-unsubstituted $C_2$-$C_{10}$-alkenylamino has 2 to 10 carbon atoms. The term "heteroatom-unsubstituted $C_n$-alkenylamino" includes groups, having the structure —NHR, in which R is a heteroatom-unsubstituted $C_n$-alkenyl, as that term is defined above. Examples of heteroatom-unsubstituted $C_n$-alkenylamino groups also include dialkenylamino and alkyl(alkenyl)amino groups.

The term "heteroatom-substituted $C_n$-alkenylamino" refers to a radical, having a single nitrogen atom as the point of attachment and at least one nonaromatic carbon-carbon double bond, but no carbon-carbon triple bonds, further having one or two carbon atoms attached to the nitrogen atom, further having a linear or branched, cyclic or acyclic structure, further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkenylamino has 2 to 10 carbon atoms. The term "heteroatom-substituted $C_n$-alkenylamino" includes groups, having the structure —NHR, in which R is a heteroatom-substituted $C_n$-alkenyl, as that term is defined above.

The term "heteroatom-unsubstituted $C_n$-alkynylamino" refers to a radical, having a single nitrogen atom as the point of attachment, further having one or two carbon atoms attached to the nitrogen atom, further having a linear or branched, cyclic or acyclic structure, containing at least one carbon-carbon triple bond, a total of n carbon atoms, at least one hydrogen atoms, a total of one nitrogen atom, and no additional heteroatoms. For example, a heteroatom-unsubstituted $C_2$-$C_{10}$-alkynylamino has 2 to 10 carbon atoms. The term "heteroatom-unsubstituted $C_n$-alkynylamino" includes groups, having the structure —NHR, in which R is a heteroatom-unsubstituted $C_n$-alkynyl, as that term is defined above. An alkynylamino group includes dialkynylamino and alkyl (alkynyl)amino groups.

The term "heteroatom-substituted $C_n$-alkynylamino" refers to a radical, having a single nitrogen atom as the point of attachment, further having one or two carbon atoms attached to the nitrogen atom, further having at least one nonaromatic carbon-carbon triple bond, further having a linear or branched, cyclic or acyclic structure, and further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkynylamino has 2 to 10 carbon atoms. The term "heteroatom-substituted $C_n$-alkynylamino" includes groups, having the structure —NHR, in which R is a heteroatom-substituted $C_n$-alkynyl, as that term is defined above.

The term "heteroatom-unsubstituted $C_n$-arylamino" refers to a radical, having a single nitrogen atom as the point of attachment, further having at least one aromatic ring structure attached to the nitrogen atom, wherein the aromatic ring structure contains only carbon atoms, further having a total of n carbon atoms, 6 or more hydrogen atoms, a total of one nitrogen atom, and no additional heteroatoms. For example, a heteroatom-unsubstituted $C_6$-$C_{10}$-arylamino has 6 to 10 carbon atoms. The term "heteroatom-unsubstituted $C_n$-arylamino" includes groups, having the structure —NHR, in which R is a heteroatom-unsubstituted $C_n$-aryl, as that term is defined above. A heteroatom-unsubstituted arylamino group includes diarylamino and alkyl(aryl)amino groups.

The term "heteroatom-substituted $C_n$-arylamino" refers to a radical, having a single nitrogen atom as the point of attachment, further having a total of n carbon atoms, at least one hydrogen atom, at least one additional heteroatoms, that is, in addition to the nitrogen atom at the point of attachment, wherein at least one of the carbon atoms is incorporated into one or more aromatic ring structures, further wherein each additional heteroatom is independently selected from the group consisting of N, O, F, Cl, Br, I, Si, P, and S. For example, a heteroatom-substituted $C_6$-$C_{10}$-arylamino has 6 to 10 carbon atoms. The term "heteroatom-substituted $C_n$-arylamino" includes groups, having the structure —NHR, in which R is a heteroatom-substituted $C_n$-aryl, as that term is defined above. A heteroatom-substituted arylamino group includes heteroarylamino groups.

The term "heteroatom-unsubstituted $C_n$-aralkylamino" refers to a radical, having a single nitrogen atom as the point of attachment, further having one or two saturated carbon atoms attached to the nitrogen atom, further having a total of n carbon atoms, wherein at least 6 of the carbon atoms form an aromatic ring structure containing only carbon atoms, 8 or more hydrogen atoms, a total of one nitrogen atom, and no additional heteroatoms. For example, a heteroatom-unsubstituted $C_7$-$C_{10}$-aralkylamino has 7 to 10 carbon atoms. The term "heteroatom-unsubstituted $C_n$-aralkylamino" includes groups, having the structure —NHR, in which R is a heteroatom-unsubstituted $C_n$-aralkyl, as that term is defined above. An aralkylamino group includes diaralkylamino groups.

The term "heteroatom-substituted $C_n$-aralkylamino" refers to a radical, having a single nitrogen atom as the point of attachment, further having at least one or two saturated carbon atoms attached to the nitrogen atom, further having a total of n carbon atoms, 0, 1, or more than one hydrogen atom, at least one additional heteroatom, that is, in addition to the nitrogen atom at the point of attachment, wherein at least one of the carbon atom incorporated into an aromatic ring, further wherein each heteroatom is independently selected from the group consisting of N, O, F, Cl, Br, I, Si, P, and S. For example, a heteroatom-substituted $C_7$-$C_{10}$-aralkylamino has 7 to 10 carbon atoms. The term "heteroatom-substituted $C_n$-aralkylamino" includes groups, having the structure —NHR, in which R is a heteroatom-substituted $C_n$-aralkyl, as that term is defined above. The term "heteroatom-substituted aralkylamino" includes the term "heteroaralkylamino."

The term "heteroatom-unsubstituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n carbon atoms, 1 or more hydrogen atoms, a total of one oxygen atom, a total of one nitrogen atom, and no additional heteroatoms. For example, a heteroatom-unsubstituted $C_1$-$C_{10}$-amido has 1 to 10 carbon atoms. The term "heteroatom-unsubstituted $C_n$-amido" includes groups, having the structure —NHR, in which R is a heteroatom-unsubstituted $C_n$-acyl, as that term is defined above. The term amido includes N-alkyl-amido, N-aryl-amido, N-aralkyl-amido, acylamino, alkylcarbonylamino, arylcarbonylamino, and ureido groups. The group, —NHCOCH$_3$, is an example of a heteroatom-unsubstituted amido group.

The term "heteroatom-substituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n aromatic or nonaromatic carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a heteroatom-substituted $C_1$-$C_{10}$-amido has 1 to 10 carbon atoms. The term "heteroatom-substituted $C_n$-amido" includes groups, having the structure —NHR, in which R is a heteroatom-unsubstituted $C_n$-acyl, as that term is defined above. The group, —NHCO$_2$CH$_3$, is an example of a heteroatom-substituted amido group.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like. Other suitable salts are known to one of ordinary skill in the art.

Suitable pharmaceutically acceptable salts may also be formed by reacting the agents of the invention with an organic base such as methylamine, ethylamine, ethanolamine, lysine, ornithine and the like. Other suitable salts are known to one of ordinary skill in the art.

Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable and as long as the anion or cation does not contribute undesired qualities or effects. Further, additional pharmaceutically acceptable salts are known to those skilled in the art, and may be used within the scope of the invention. Additional examples of pharmaceutically acceptable salts and their methods of preparation and use are presented in Pharmaceutical Salts: Properties, Selection and Use—A Handbook, by C. G. Wermuth and P. H. Stahl, Verlag Helvetica Chimica Acta, 2002, which is incorporated herein by reference.

As used herein, the term "patient" is intended to include living organisms in which certain conditions as described herein can occur. Examples include humans, monkeys, cows, sheep, goats, dogs, cats, mice, rats, and transgenic species thereof. In a preferred embodiment, the patient is a primate. In an even more preferred embodiment, the primate is a human. Other examples of subjects include experimental animals such as mice, rats, dogs, cats, goats, sheep, pigs, and cows. The experimental animal can be an animal model for a disorder, e.g., a transgenic mouse with an Alzheimer's-type neuropathology. A patient can be a human suffering from a neurodegenerative disease, such as Alzheimer's disease, or Parkinson's disease.

As used herein, the term "IC$_{50}$" refers to an inhibitory dose which is 50% of the maximum response obtained.

As used herein, the term "water soluble" means that the compound dissolves in water at least to the extent of 0.010 mole/liter or is classified as soluble according to literature precedence.

As used herein, "predominantly one enantiomer" means that the compound contains at least 95% of one enantiomer, or more preferably at least 98% of one enantiomer, or most preferably at least 99% of one enantiomer. Similarly, the phrase "substantially free from other optical isomers" means that the composition contains at most 5% of another enantiomer or diastereomer, more preferably 2% of another enantiomer or diastereomer, and most preferably 1% of another enantiomer or diastereomer.

As used herein the specification, "a" or "an" may mean one or more. As used herein in the claim(s), when used in conjunction with the word "comprising" or "having," the words "a" or "an" may mean one or more than one. As used herein "another" may mean at least a second or more.

Other abbreviations used herein are as follows: DMSO, dimethyl sulfoxide; iNOS, inducible nitric oxide synthase; COX-2, cyclooxygenase-2; NGF, nerve growth factor; IBMX, isobutylmethylxanthine; FBS, fetal bovine serum; GPDH, glycerol 3-phosphate dehydrogenase; RXR, retinoid X receptor; TGF-β, transforming growth factor-β; IFN-γ, interferon-γ; LPS, bacterial endotoxic lipopolysaccharide; TNF-α, tumor necrosis factor-α; IL-1β, interleukin-1β; GAPDH, glyceraldehyde-3-phosphate dehydrogenase; MTT, 3-[4,5-dimethylthiazol-2-yl]-2,5-diphenyltetrazolium bromide; TCA, trichloroacetic acid; HO-1, inducible heme oxygenase.

III. Synthetic Methodology

A. Lanthionine

Lanthionine was first isolated from the treatment of wool with sodium carbonate (Horn et al., 1941) and was first synthesized from cysteine and β-chloroalanine (Brown et al., 1941). Lanthionine has been identified in nature, and lanthionine has been isolated from human hair, lactalbumin, and feathers. Lanthionine has also been found in bacterial cell walls and is a component of a group of gene encoded peptide antibiotics called lantibiotics, which includes nisin (a food preservative), subtilin, epidermin (an anti *staphylococcus* and *streptococcus* agent), and ancovenin (an enzyme inhibitor) (Paul et al., 2005; Shao et al., 1995).

"Lanthionine," as used herein, refers to a compound having the structure HOOC—CH(NH$_2$)—CH$_2$—S—CH$_2$—CH(NH$_2$)—COOH and salts and hydrates thereof, regardless of the stereochemistry of the molecule or salt.

Lanthionine may be synthesized via several different methods. For example, lanthionine may be synthesized via sulfur extrusion from cystine (Harpp et al., 1971), ring opening of serine β-lactone (Shao et al., 1995) and Michael addition of cysteine to dehydroalanine (Probert et al., 1996). Specific optical isomers of lanthionine, such as d,d-lanthionine (d-lanthionine), d,l-lanthionine (meso-lanthionine), or l,l-lanthione (l-lanthionine), may be prepared by either chemical of biochemical synthetic means, which are well-known in the art.

B. Lanthionine Ketimine and Lanthionine Ketimine Derivatives

A biochemical synthetic pathway to lanthionine ketimine (LK) from the precursor lanthionine and the alpha-keto acid pyruvate is shown in Scheme 3, above. L-amino acid oxidase can facilitate a similar conversion of the linear lanthionine into the cyclic product; however, in the brain KAT (GTK, CCOL) is thought to provide the primary route (Fontana et al., 1997; Cavallini et al., 1985; Cavallini et al., 1983; Cavallini et al., 1991; Fontana et al., 1990). Lanthionine ketimine can also be synthesized by the spontaneous reaction of 3-bromopyruvate with cysteine in water as reported by Cavallini and colleagues (Cavallini et al., 1983)

As used herein, "LK derivative" is defined as a compound having the structure:

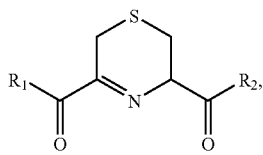

wherein $R_1$ and $R_2$ are each independently —OH, —NH$_2$, or heteroatom substituted or unsubstituted versions of $C_1$-$C_{15}$-alkoxy, $C_2$-$C_{15}$-alkenylamino, $C_2$-$C_{15}$-alkynylamino, $C_1$-$C_{15}$-aryloxy, $C_2$-$C_{15}$-aralkoxy, $C_1$-$C_{15}$-acyloxy, $C_1$-$C_{15}$-alkylamino, $C_2$-$C_{15}$-alkenylamino, $C_2$-$C_{15}$-alkynylamino, $C_1$-$C_{15}$-arylamino, $C_2$-$C_{15}$-aralkylamino, or $C_1$-$C_{15}$-amido, and pharmaceutically acceptable salts, hydrates, and optical isomers thereof.

The following general synthesis may be used to produce LK and LK derivatives. A concentrated aqueous solution (typically >100 mM) of enantiomerically pure L-cysteine, L-cysteine-ester, or L-cysteine-amide (or the respective hydrochloride salts) is mixed with an equimolar solution (preferably aqueous) of 3-bromo-pyruvate or similar α-keto acid, ester, or amide. A lanthionine intermediate forms, and spontaneously cyclizes to yield LK or an LK derivative with retention of stereochemistry. LK or the LK derivative can be recovered by crystallization, extraction, distillation and related techniques that would be well-known to a practitioner of ordinary skill in the art of synthetic organic chemistry. In the case of the ethyl ester (R)-LKE1, shown below, an opalescent crystalline precipitate is formed within 10 minutes. This precipitate is recovered by filtration and recrystallized from methanol.

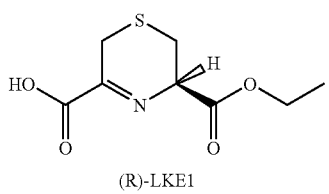

(R)-LKE1

Similarly, (S)-LKE1 was made by starting with D-cysteine (rather than the biologically normal L-cysteine). In general, the enantioselective synthesis is similar to that used for making the racemate: Instead of starting with a racemic mixture of cysteine-esters, one starts with chiral cysteine (either D or L), substantially free from the other enantiomer.

A general method for synthesis of certain LK derivatives in vitro is shown in Scheme 4 below.

Scheme 4.

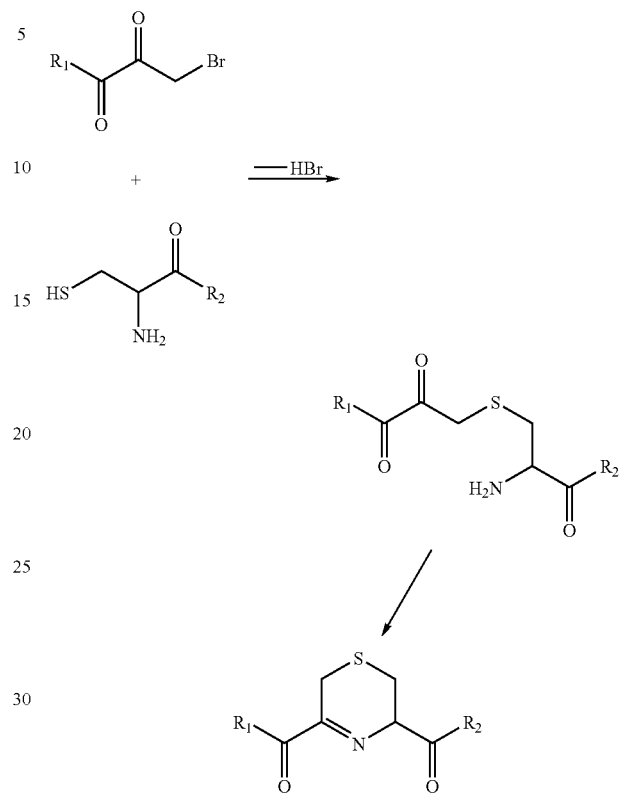

A person of skill in the art will appreciate that other LK derivatives of this invention can be synthesized by changing the identity of $R_1$ and $R_2$. For example, $R_1$ and $R_2$ may each independently be selected from the groups including alkoxy, alkenylamino, alkynylamino, aryloxy, aralkoxy, acyloxy, alkylamino, alkenylamino, alkynylamino, arylamino, aralkylamino, or amido groups.

C. TMDCA and TMDCA Derivatives

LK can undergo further reduction of the N═C bond to yield thiomorpholine dicarboxylic acid (TMDCA), shown below. (Giulidori et al., 1984; Cavallini et al., 1983); both references are incorporated herein by reference. Similarly, one can chemically reduce the C═N bond of LK or of an LK derivative, by using cyanoborohydride, to form TMDCA and TMDCA derivatives, respectively.

As used herein, "TMDCA derivative" is defined as a compound having the structure:

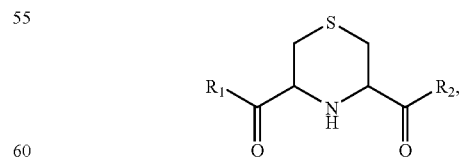

wherein $R_1$ and $R_2$ are each independently —OH, —NH$_2$, or heteroatom substituted or unsubstituted versions of $C_1$-$C_{15}$-alkoxy, $C_2$-$C_{15}$-alkenylamino, $C_2$-$C_{15}$-alkynylamino, $C_1$-$C_{15}$-aryloxy, $C_2$-$C_{15}$-aralkoxy, $C_1$-$C_{15}$-acyloxy, $C_1$-$C_{15}$-alkylamino, $C_2$-$C_{15}$-alkenylamino, $C_2$-$C_{15}$-alkynylamino, $C_1$-$C_{15}$-arylamino, $C_2$-$C_{15}$-aralkylamino, or $C_1$-$C_{15}$-amido, and pharmaceutically acceptable salts, hydrates, and optical isomers thereof.

TMDCA derivatives would be synthesized as the LK/LK-derivatives then reduced using cyanoborohydride salts, borohydride salts, or other chemical reducing agents to convert the imine bond to an amine.

LK amide derivatives (LKAs) can be synthesized in several possible ways. For example, one could make an amide from bromopyruvate and a primary amine. In certain embodiments, a carbodiimide catalyst would be used to assist in this coupling reaction. One would then purify the amide (some amount of side products would be expected); then one would react the amide product with L-cysteine or a cysteine-ester derivative, such as cysteine-ethyl-ester, as described for the general (R)-LKE1 synthesis. Alternatively, one could make LK or an LKE first, then react the free carboxylate(s) with a primary amine using a carbodiimide or a similar coupling catalyst.

The only restrictions with bromopyruvate Schemes is that cysteine or cysteine derivatives must have a free —SH group to displace the —Br group, and they must retain an unsubstituted free —$NH_2$ on the cysteine. This is necessary so that the intermediate can cyclize through the reaction of the —$NH_2$ group of the cysteine with the ketone group from the pyruvate. Therefore, a person of skill in the art would recognize that it would be very difficult to derivatize the cysteine's amide group prior to the coupling reaction; however, it would be easier to derivatize the carboxyl group of the cysteine prior to coupling. For example, in certain embodiments, the carboxylic acid group of the cysteine is converted to an amide. A person of skill in the art would understand that one might first need to protect the N-terminal —$NH_2$ group of the cysteine or cysteine derivative prior to the carbodiimide coupling, then do the carbodiimide coupling, then deprotect the N-terminal group, then work up and/or purify the resulting amide derivative of cysteine.

One aspect of the present invention is the improved delivery of LK and/or LK derivatives to target cells. The improved delivery comprises improved delivery through cell membranes and/or improved permeability through the blood brain barrier (BBB). The invention accomplishes the improved delivery through derivatization of the LK to form LK esters (LKEs) and LK amides (LKAs). The invention contemplates that the $R_1$ and $R_2$ groups of the structure:

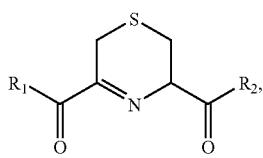

can be substituted with one or more functional groups that will facilitate the transport of the resulting molecule through the BBB. In some of these embodiments, the functional group interacts with BBB-specific transport mechanisms. For example, an ascorbyl derivative of LK are be expected to take advantage of BBB ascorbyl transporters. Also, certain amino acid esters or amide derivatives of LK are expected to be readily transported across the BBB by means of BBB transport enzymes. In certain embodiments, $R_1$ and/or $R_2$ is a serinyl group. Methods of making ascorbyl, dehydroascorbyl, and amino acid esters of drugs containing carboxylic acids are well-known in the art.

Conjugation of ascorbyl, dehydroascorbyl, serinyl, or glycinyl to the LK derivative may be performed using techniques known in the art. See e.g., Manfredini et al., 2001 and Huang et al., 2001; both references are incorporated herein by reference.

In certain embodiments, the invention contemplates that $R_1$ and/or $R_2$ is an ascorbyl group, shown below, connected through the hydroxyl group at carbon atom labeled 5:

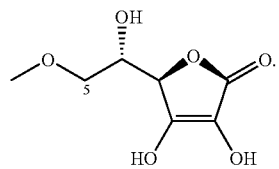

The invention also contemplates that $R_1$ and/or $R_2$ is an ascorbyl group, shown below, connected through the hydroxyl group at carbon atom labeled 4:

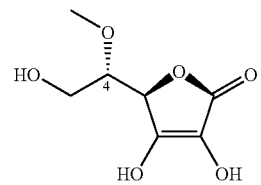

In certain embodiments, the invention contemplates that $R_1$ and/or $R_2$ is a dehydroascorbyl group, shown below, connected through the hydroxyl group at carbon atom labeled 5:

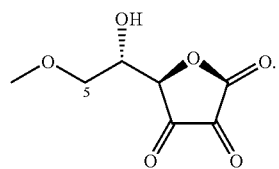

The invention also contemplates that $R_1$ and/or $R_2$ is a dehydroascorbyl group, shown below, connected through the hydroxyl group at carbon atom labeled 4:

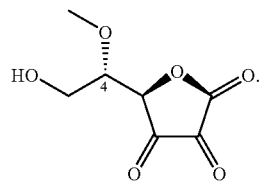

IV. Pharmaceutical Preparations

Pharmaceutical compositions of the present invention comprise an effective amount of lanthionine, lanthionine ketimine (LK), LK derivative, thiomorpholine dicarboxylic acid (TMDCA), TMDCA derivative, and/or additional agents, dissolved or dispersed in a pharmaceutically acceptable carrier. The phrases "pharmaceutical" or "pharmacologically acceptable" refers to molecular entities and compositions that produce no adverse, allergic or other untoward reaction when administered to an animal, such as, for example, a human. The preparation of an pharmaceutical composition that contains at least one lanthionine, LK or LK derivative or additional active ingredient will be known to those of skill in the art in light of the present disclosure, as exemplified by Remington's Pharmaceutical Sciences, 2003, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 995, pp. 1289-1329, incorporated herein by reference). Except insofar as any conventional carrier is incompatible with the active ingredient, its use in the pharmaceutical compositions is contemplated.

The lanthionine, LK, LK derivative, TMDCA, TMDCA derivative, and/or additional agents, may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 2003, incorporated herein by reference).

The lanthionine, LK, LK derivative, TMDCA, TMDCA derivative, and/or additional agents, may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semisolid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the pharmaceutical composition may include small quantities of pharmacologically acceptable chelators or co-antioxidants. Examples of chelators include ethylenediaminetetraacetic acid (EDTA) and ethylene glycol-bis(beta-aminoethyl ether)-N,N,N',N'-tetraacetic acid (EGTA). Examples of antioxidants including gallate esters, ascorbate, vitamin E (or other tocopherols), butylated hydroxytoluene, and/or benzoic acid. These chelators and/or co-antioxidants may be used to stabilize lanthionine, LK, LK derivative, TMDCA, TMDCA derivative, and/or additional agents. In certain embodiments, these chelators and/or antioxidants may be stabilize lanthionine, LK, LK derivative, TMDCA, TMDCA derivative, and/or additional agents, from decomposition by autooxidation.

In further embodiments, the present invention may concern the use of a pharmaceutical lipid vehicle compositions that include lanthionine, LK, LK derivative, TMDCA, TMDCA derivative, and/or additional agents, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the lanthionine, LK, LK derivative, TMDCA, TMDCA derivative, and/or additional agents, may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Alimentary Compositions and Formulations

In certain embodiments of the present invention, lanthionine, lanthionine ketimine (LK), a LK derivative, thiomorpholine dicarboxylic acid (TMDCA), a TMDCA derivative, and/or additional agents is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, lanthionine, LK, LK derivative, TMDCA, TMDCA derivative, and/or additional agents, may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,753,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other preferred embodiments of the invention, the active compound lanthionine, LK, LK derivative, TMDCA, TMDCA derivative, and/or additional agents, may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch." For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

V. Single-Agent Treatments

The methods and compounds of the present invention may be used for prevention and treatment of cancer, diseases involving inflammation and/or oxidative stress, and/or disorders of the central nervous system (CNS), including stroke. In certain embodiments, the invention provides methods of treating and/or preventing a disease or disorder of the central nervous system, such as those mentioned above, or throughout this application, in an individual comprising, administering at least one compound of this invention to the individual in an amount effective to treat and/or prevent the disease.

LK and a synthetic cell-permeable ethyl ester, (R)-LKE1, were found to have anti-oxidant, anti-neuroinflammatory, neuroprotective activities, and antiproliferative properties. These findings establish that cyclic sulfurous thioethers such as LK are biochemically important and purposeful molecules in the mammalian central nervous system (CNS).

For example, the methods and compounds of present invention are expected to by useful for treating Parkinson's disease in an individual. For example, FIG. 15 shows (R)-LKE1 protecting SHSY5Y cells from rotenone toxicity, a form of mitochondrial impairment implicated Parkinson's disease. In this experiment SHSY5Y cultures were treated with (R)-LKE1 for 30 min. prior to addition of rotenone, then assayed for viability at various later time points.

Kynurenine amino transferase (KAT) is recognized as a central enzyme in the degradation of tryptophan metabolites (Moroni, 1999; Foster et al., 1992; Urenjak and Obrenovitch, 2000; Heyes, 1996; Stone and Darlington, 2002) (see Scheme 4, below). In this role, KAT converts kynurenine (the oxidative metabolite of tryptophan) plus pyruvate into kynurenic acid (KYNA), the only known endogenous broad-spectrum antagonist of all subtypes of ionotropic glutamate receptors (Moroni, 1999; Foster et al., 1992; Urenjak and Obrenovitch, 2000; Heyes, 1996; Stone and Darlington, 2002). On a more subtle level, KAT deflects the flow of tryptophan oxidation products away from kynurenine hydroxylase (KH), a pathway leading to excitotoxic quinolinic acid (QUIN) and redox-cycling, prooxidant 3-hydroxy anthranilic acid (Stone and Darlington, 2002; Beal et al., 1986; Magnuson et al., 1987; Chiarugi et al., 2001; Blight et al., 1997) (HAA). A less well-appreciated reaction mediated by KAT is the analogous conversion of lanthionine plus pyruvate into lanthionine ketimine (Cooper, 2004). This latter function of KAT has been relatively neglected in neurochemical investigations owing to the lack of documented functions for the cyclic thioether. It is contemplated by this invention that suggests that lanthionine ketimine and/or the other compounds of this invention possess anti-oxidant, anti-neuroinflammatory and neuroprotective activities similar to those previously documented for KYNA. Thus, KAT may represent a heretofore unappreciated metabolic junction through which flow both indole catabolites and transulfuration by-products. In both cases the resulting end products, KYNA and LK respectively, possess biological activities that would be appropriate to the maintenance of neurochemical integrity.

Scheme 4

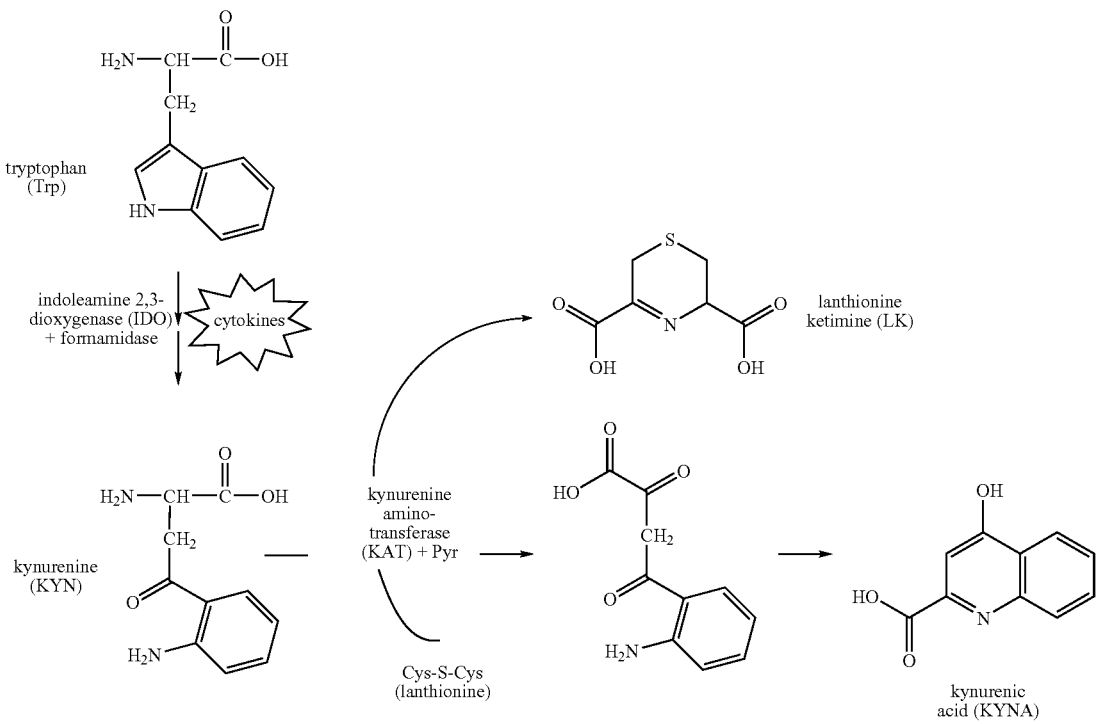

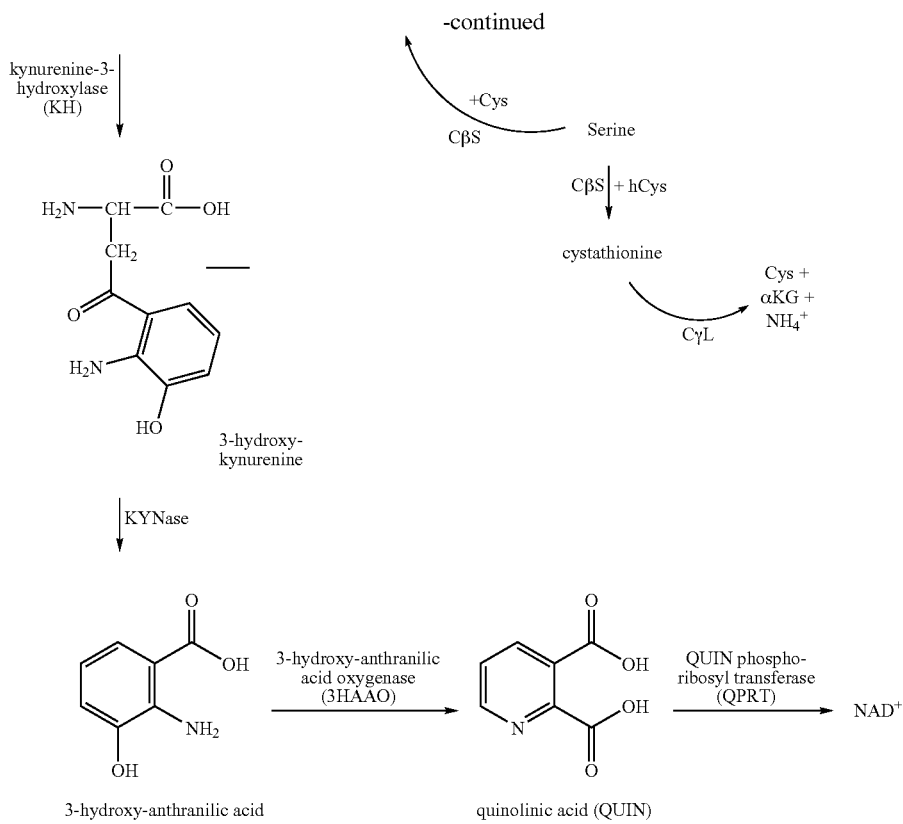

A protective function for LK and/or the other compounds of this invention, would be logical when one considers the relationship of KAT to other elements of tryptophan catabolism. It has been estimated that >95% of tryptophan that is not utilized by protein synthesis is degraded through the kynurenine pathway (Moroni, 1999). This pathway is constitutively active but may be regulated, primarily at the level of indole 2,3-dioxygenase (IDO) (Moroni, 1999). IDO is potently up-regulated at sites of inflammation in response to pro-inflammatory cytokines, especially interferon gamma (IFNγ) (Moroni, 1999; Heyes, 1996; Stone and Darlington, 2002). IDO catalyzes superoxide-dependent fragmentation of the tryptophan ring, yielding kynurenine (KYN). Downstream products of KYN include HAA and quinolinic acid, both of which are necessary to $NAD^+$ synthesis but which can be neurotoxic in elevated concentrations (Moroni, 1999; Beal et al., 1986; Magnuson et al., 1987; Chiarugi et al., 2001; Blight et al., 1997). QUIN in particular is a potent NMDA receptor agonist and can produce neurodegeneration resembling Huntington's disease (HD) when injected locally into rodent striatum (Beal et al., 1986). Moreover, several studies suggest elevated QUIN in experimentally-damaged rodent spinal cord (Chiarugi et al., 2001; Blight et al., 1997) and in human brain samples taken from patients with neurodegenerative diseases including Alzheimer's disease (AD) (Wildner et al., 2000; Guillemin et al., 2003; Guillemin et al., 2005), HD (Guidetti et al., 2004; Stoy et al., 1995; Jauch et al., 1995) and ALS (Guillemin et al., 2005). This invention contemplates that KAT products such as LK, as well as LK derivative, and/or other compounds of this invention, might be synthesized in proportion to elevated KYN, in order to partially balance the neurotoxic stress of elevated QUIN and HAA. Moreover the microglia-suppressive actions observed for LK and its cell-permeable ester may promote a negative feedback loop to inhibit a localized neuroinflammatory reaction.

A. Methods Involving Lanthionine

The present invention provides methods for treating a disease (e.g., an inflammatory disease) in an individual comprising administering lanthionine to the individual in amount of lanthionine effective to treat the disease. In certain embodiments a specific optical isomer of lanthionine is used. For example, d,d-lanthionine (d-lanthionine), d,l-lanthionine (meso-lanthionine), or l,l-lanthione (l-lanthionine) may be used. Optionally, lanthionine may be administered in combination with other compounds, such a glucose, pyruvate, or an ester or amide derivative of pyruvate to stimulate endogenous production of LK.

Lanthionine ketimine (LK) may also be generated in a patient by administering lanthionine and/or pyruvate to the patient. In certain embodiments, LK may be generated in a patient by administering lanthionine and an ester or amide derivatives of pyruvate to the patient. In certain aspects, the invention contemplates that lanthionine and pyruvate, or an ester or amide derivatives of pyruvate, will react together in a patient to form lanthionine ketimine. In other embodiments, pyruvate, or an ester or amide derivatives of pyruvate, would not be administered in combination with lanthionine, instead lanthionine would react with endogenous pyruvate to generate lanthionine ketimine. For example, the pyruvate source may be dietary. Pyruvate is found in certain foods and beverages, including fruits, vegetables, beer, and red wine. Alternatively, the pyruvate source may be generated from the catabolic processes of the patient receiving treatment. For example, pyruvate is the product of the glycolysis of glucose.

Glucose transporters are found in most mammalian cells. Glucose is known to readily cross the blood-brain barrier by means of the glucose transporter GLUT1. The invention therefore contemplates that the lanthionine ketimine may be generated in the brain of an individual by administering an amount of lanthionine to the individual effective to generate lanthionine ketimine in the brain of the individual.

In another embodiment, lanthionine may be generated in a patient by the treatment of lanthionine and pyruvate, or an ester or amide derivative of pyruvate. Pyruvate supplementation may nevertheless be advantageous. For example, it has been shown that administering pyruvate to rodent models of neurodiseases does sometimes slow progression, supporting the hypothesis that in vivo supplementation strategies indeed may be useful. See, for example (Ryu et al., 2003) which reference is incorporated herein. Furthermore, studies have demonstrated the neuroprotective effects of pyruvate in the quinolinic acid rat model of Huntington's disease. For example, in Ryu et al. (2003) teaches that giving 1000 mg/kg pyruvate intraperitoneally partially mitigates neurodisease in the quinolinic acid rat model. In certain embodiments, the invention contemplates that administering a pyruvate ester might allow pyruvate to survive passage across the gut "unmetabolized" by the Krebs cycle.

Also, such a combination treatment may be necessary in order to achieve sufficient levels of pyruvate in the brains of the patients not generating enough pyruvate through standard biochemical catabolism. For example, a patient suffering from De Vivo disease, also known as GLUT-1 deficiency syndrome) would be expected to have lower levels of glucose in their brains. Given that pyruvate is the product of the glycolysis of glucose (one molecule of glucose breaks down into two molecules of pyruvic acid), one would expect that a person suffering from De Vivo disease would have depressed level of pyruvate in their brains. Treating these patients with a combination of lanthionine and pyruvate would be expected to generate higher levels of LK, than would treatment of with lanthionine alone. This invention may therefore provide a method of treating patients suffering from De Vivo disease, comprising administering at least one compound of this invention to the patient in an amount effective to treat and/or prevent the disease.

One may cause and/or promote the formation of lanthionine ketimine in a patient by administering lanthionine (and, optionally, pyruvate or an ester of amide derivative of pyruvate) to the patient. In vivo, lanthionine ketimine is formed by the action of kynurenine aminotransferase (KAT) on lanthionine+pyruvate; this reaction forms LK. Therefore, rather than giving LK or an ester (or other derivative) directly one may increase physiological concentrations of LK by increasing the concentration of the precursor lanthionine. Administering pyruvate, or ester or amide derivatives of pyruvate, as supplements to the patient in addition to lanthionine would likely synergize the formation of LK in the subject.

B. Methods Involving LK

Lanthionine ketimine (LK) was described in the late 1980s and early 1990s by Doriano Cavallini and colleagues (Fontana et al., 1997; Cavallini et al., 1985; Cavallini et al., 1983; Cavallini et al., 1991; Fontana et al., 1990; Cooper, 2004) who first detected the compound in bovine brain. LK appears to be synthesized from the "unnatural" amino acid lanthionine (a thioether condensate of two cysteine molecules or a cysteine and a serine). Lanthionine may form through the action of the transulfuration enzyme cystathionine β-synthase (CβS). Discoveries by the inventor suggest a natural route of synthesis by an endogenous mammalian enzyme, lanthionine C-like protein 1 (LanCL1). Lanthionine is a facile substrate for the pyridoxal phosphate-dependent kynurinine aminotransferase (KAT)/glutamine transaminase K (GTK)/cysteine conjugate beta-lyase (CβL) (Cavallini et al., 1983; Cooper, 2004). KAT activity exchanges the alpha keto-carboxylate of a donor (typically pyruvate) with the amino acyl group of a target amino acid. The product of this catalysis is a new alpha-keto intermediate that spontaneously and rapidly cyclizes to form LK (see synthesis below). This imine can experience enzymatic reduction to form the cyclic amino acid analog 1,4-thiomorpholine-3,5-dicarboxylic acid (TMDA). Brain levels of LK reach micromolar concentrations (Fontana et al., 1997; Cavallini et al., 1995).

Prior to the present invention, no discrete neurochemical activity had been documented for LK or TMDA, however LK reportedly binds selectively to synaptosomal membranes with 50 nM affinity (Cavallini et al., 1991). The synthesis of LK from 3-bromopyrivate and cysteine, is known in the prior art (Cavallini et al., 1983). LK is also mentioned U.S. 2003/0185754, which describes various treatments for bipolar disorders and mood disorders.

C. Methods Involving LK Derivatives.

One aspect of the present invention is the improved delivery of LK to target cells. The improved delivery comprises improved delivery through cell membranes and/or improved permeability through the blood brain barrier (BBB). The invention accomplishes the improved delivery through derivatization of the LK to form LK esters (LKEs) and LK amides (LKAs). This derivatization was not taught by the prior art.

LK derivatives, for example (R)-LKE1, should provide an optimal balance of hydrophobic/hydrophilic character, allowing these compounds to more capable of penetrating cell membranes, to reach intracellular targets of action. For example, the ester (R)-LKE1 was synthesized on the theory that reduced hydrophilicity of the ester would render the compound more capable of penetrating cell membranes, to reach intracellular targets of action. The ester derivative (R)-LKE1 proved statistically significantly more potent at suppressing cytokine activation of effector cells, than was the unesterified lanthionine ketimine (see FIG. 1A).

In some embodiments, the LK derivatives have an improved ability to pass through the blood-brain barrier, which is required for the treatment of most CNS disorders. In some of these embodiments, the LK derivatives has functional groups in the $R_1$ and/or $R_2$ positions which interact with BBB-specific transport mechanisms. For example, an ascorbyl derivative of LK are be expected to take advantage of BBB ascorbyl transporters. Also, certain amino acid esters or amide derivatives of LK are expected to be readily transported across the BBB by means of BBB transport enzymes. For example, in certain embodiments, $R_1$ and/or $R_2$ are serinyl group.

In some of these embodiments, an internalized LK ester, for example (R)-LKE1, is anticipated to undergo facile hydrolysis via intrinsic esterase activity, to yield the active lanthionine ketimine product. Alternatively, the LK ester derivatives could undergo chemical reaction with target enzymes (e.g., cyclooxygenases) in order to acylate and inactivate the target molecules. The inventor has demonstrated that the (R)-LKE1, which is an example of an LK ester derivative, proved statistically significantly more potent at suppressing cytokine activation of effector cells, than was the unesterified lanthionine ketimine (see FIG. 1A). Subsequent tests proved efficacy of (R)-LKE1 as an inhibitor of astrocyte activation by an archetypal inflammogen, bacterial lipopolysaccharide (LPS).

D. Methods involving TMDCA and TMDCA Derivatives

Given the structural similarities between TMDCA and LK, as well as the structural similarities between TMDCA derivatives and LK derivatives, the inventor contemplates the use of TMDCA, or a TMDCA derivative, for treating a subject having any of diseases described above or through the application individual comprising, administering TMDCA, TMDCA derivative, and/or additional agents, to the individual in an amount effective to treat and/or prevent the disease. TMDCA and TMDCA derivatives are is a reduced state relative to LK and LK derivates, respectively. Therefore TMDCA or a TMDCA derivative may be useful for treating a subject having a condition caused by elevated levels of oxidative stress in one or more tissues.

For example, the reduced lanthionine ketimine (i.e., TMDCA) was also tested against TNFα-stimulated nitrite production in the EOC-20 screen. 100 microM TMDCA (formed from cyanoborohydride reduction of LK) suppressed microglial activation to 67.5+/−3.8% (SD) of the maximum, or about 32.5% inhibition of the cytokine effect.

E. Inhibition of Inflammation

Inflammatory, oxidative, or immune mechanisms may be involved in the pathogenesis of Alzheimer's disease (AD), Parkinson's disease (PD), amyotrophiclateral sclerosis (ALS), and MS (Bagasra et al., 1995; McGeer and McGeer, 1995; Simonian and Coyle, 1996; Kaltschmidt et al., 1997). Both reactive astrocytes and activated microglia have been implicated in causation of neurodegenerative disease (NDD) and neuroinflammatory disease (NID); there has been a particular emphasis on microglia as cells that synthesize both NO and prostaglandins as products of the respective enzymes, iNOS and COX-2. De novo formation of these enzymes may be driven by inflammatory cytokines such as interferon-γ or interleukin-1. In turn, excessive production of NO may lead to inflammatory cascades and/or oxidative damage in cells and tissues of many organs, including neurons and oligodendrocytes of the nervous system, with consequent manifestations in AD and MS, and possible PD and ALS (Coyle and Puttfarcken, 1993; Beal, 1996; Merrill and Benvenist, 1996; Simonian and Coyle, 1996; Vodovotz et al., 1996). Epidemiologic data indicate that chronic use of NSAID's which block synthesis of prostaglandins from arachidonate, markedly lower the risk for development of AD (McGeer et al., 1996; Stewart et al., 1997). Thus, agents that block formation of NO and prostaglandins, may be used in approaches to prevention and treatment of NDD. The inventors contemplate that the compounds of this invention, which have been shown to block the formation of nitric oxide, as measured via nitrite concentration, (see FIGS. 1B, 2, 3, and 9A&B), are expected be useful in treating the neurological diseases described above and below.

Microglia act as the immune cells of the central nervous system (CNS), acting as phagocytes, cleaning up CNS debris. Microglia are thought to be highly mobile cells that play numerous important roles in protecting the nervous system. They are also responsible for producing an inflammatory reaction to injury and/or or stress. Microglia produce reactive free radicals and also paracrine substances involved in host defense. Excessive activation of the macrophages (microglia) can produce collateral damage to neurons and other ambient cells. There is considerable evidence that chronic microglial activation plays a major role in numerous neurological conditions including Alzheimer's dementia, Parkinson's disease, ALS, stroke, and other inflammatory brain diseases. The release of toxic elements from activated microglia, such as cytokines and excitotoxins, is known to produce neurodegeneration. Peripheral immune stimulation has been shown to activate microglia of the central nervous system, and when excessive, can lead to neurodegeneration and cognitive defects. Macrophage—or microglia-derived toxicity results in large part from excess production of nitric oxide and other free radicals; and from excess production of eicosanoids including the pain-producing and inflammation-exacerbating lipid product, prostaglandin E2 (PGE2). Thus, any safe and bioavailable compound that either (a) suppresses macrophage/microglial activation; (b) suppresses microglial/macrophage production of nitric oxide; or (c) suppresses macrophage/microglial production of PGE2, would be useful in treating chronic inflammatory diseases.

The compounds of this invention were also shown to inhibit the activation of EOC-20 microglia in response to the inflammatory cytokine tumor necrosis factor-alpha (TNFα), which is known to induce nitric oxide synthase (iNOS) and (NO) production.

Peripheral blood (PB) monocytes produce inflammatory cytokines including TNFα in response to bacterial cell wall components. TNFα is a major inflammatory cytokine that has a role in many inflammatory conditions in addition to bacterial infections. Inhibition of TNFα could provide a therapeutic approach to reducing inflammation. As shown below, (R)-LKE1 inhibits TNFα production by human PB monocytes in response to two cell wall components: lipopolysaccharide (UltraPure LPS) from *Staphylococcus aureus* (Invivogen) and peptidoglycan (PG) from *Bacillus anthracis* (List Biological Laboratories).

The invention contemplates that the methods and compounds of this invention will be useful in treating chronic inflammatory diseases by suppresses macrophage/microglial activation and/or suppressing microglial/macrophage production of nitric oxide and/or suppressing macrophage/microglial production of PGE2.

Figures 1A, 1B:
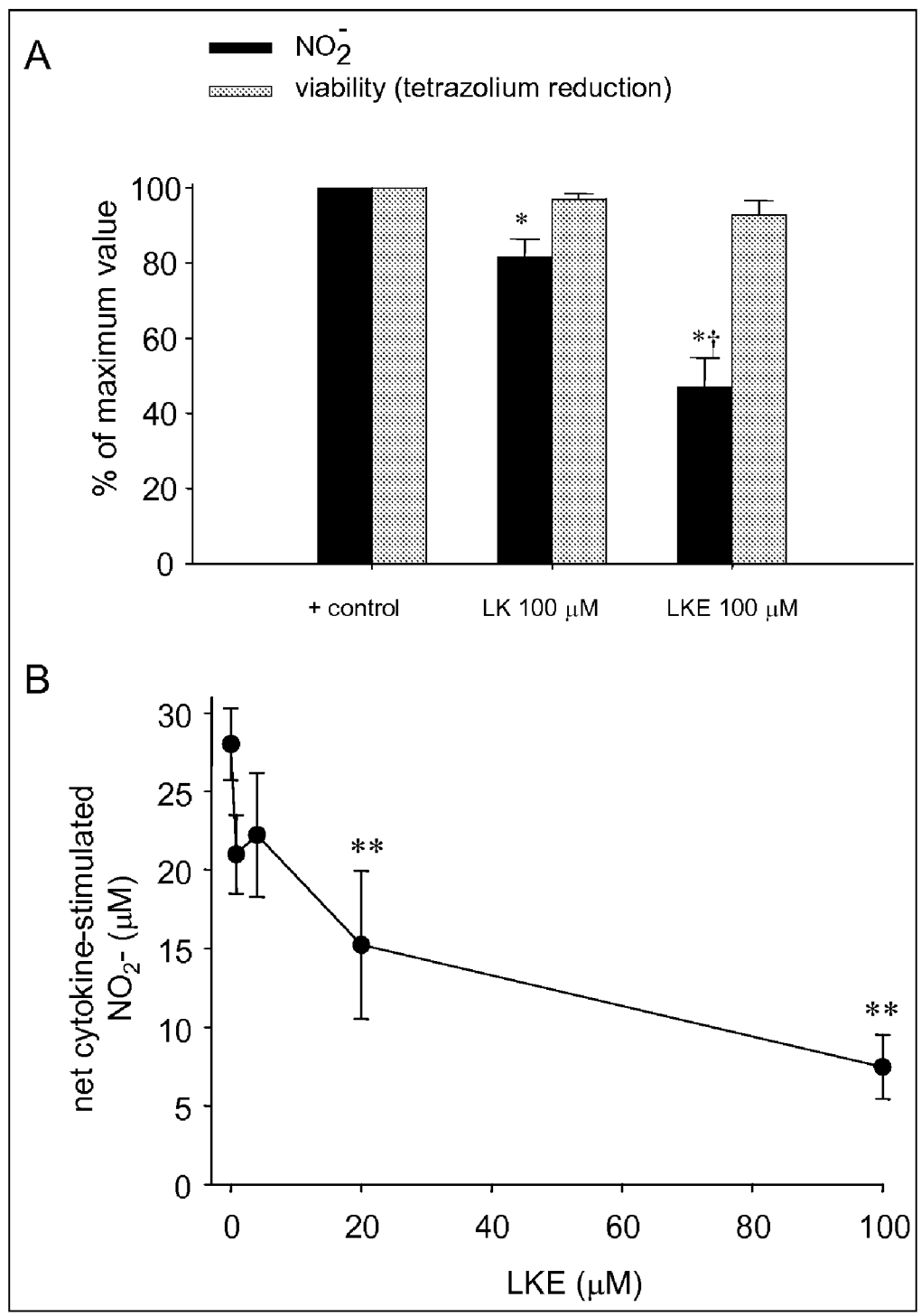
FIGS. 1A & 1B. LK and (R)-LKE1 inhibit TNFα-stimulated microglial activation.
Figure 2:
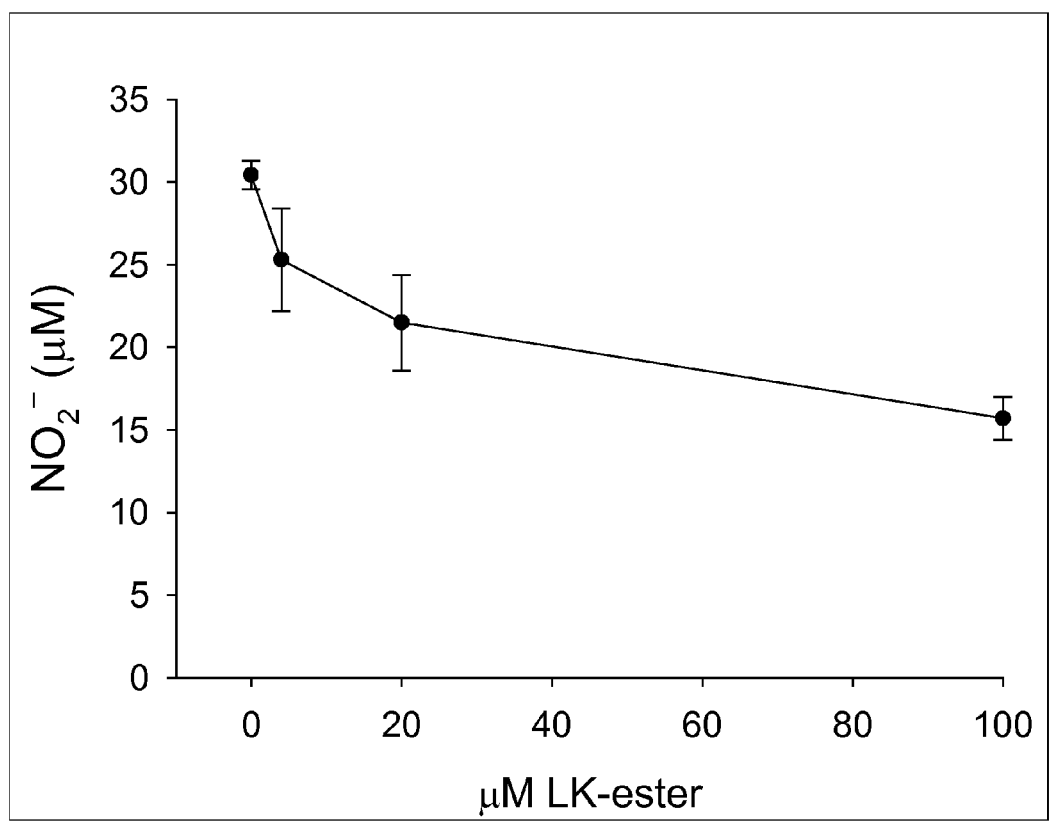
FIG. 2. (R)-LKE1 inhibits TNFα+IFNγ-stimulated microglial activation. The Dose response relationship for (R)-LKE 1 inhibition of TNFα (20ng/mL)+IFNγ (50U/mL)-stimulated nitrite production by activated EOC-20 microglia. "LK-ester" refers to (R)-LKE1.

More generally, the invention demonstrates the ability of the compounds of this invention to suppress cytokine-stimulated microglial activation, as evidenced by attenuated production of inflammatory substances including nitric oxide. For example, as shown in FIGS. 1B & 2, (R)-LK and (R)-LKE1 inhibit activation of nitric oxide production in stimulated microglial cells. (Levels of nitrite ion concentration are used as a proxy levels on NO production.) Both LK and (R)-LKE1 inhibited nitrite production by tumor necrosis factor alpha (TNFα)-stimulated EOC-20 microglia. In some embodiments, the compounds of this invention work selectively to only inhibit the production of nitric oxide. For example, the inventor has demonstrated that (R)-LKE1 does not to suppress prostaglandin E2 ($PGE_2$) production in the EOC-20 microglial cells stimulated by TNFα+IFNγ.

Figure 7:
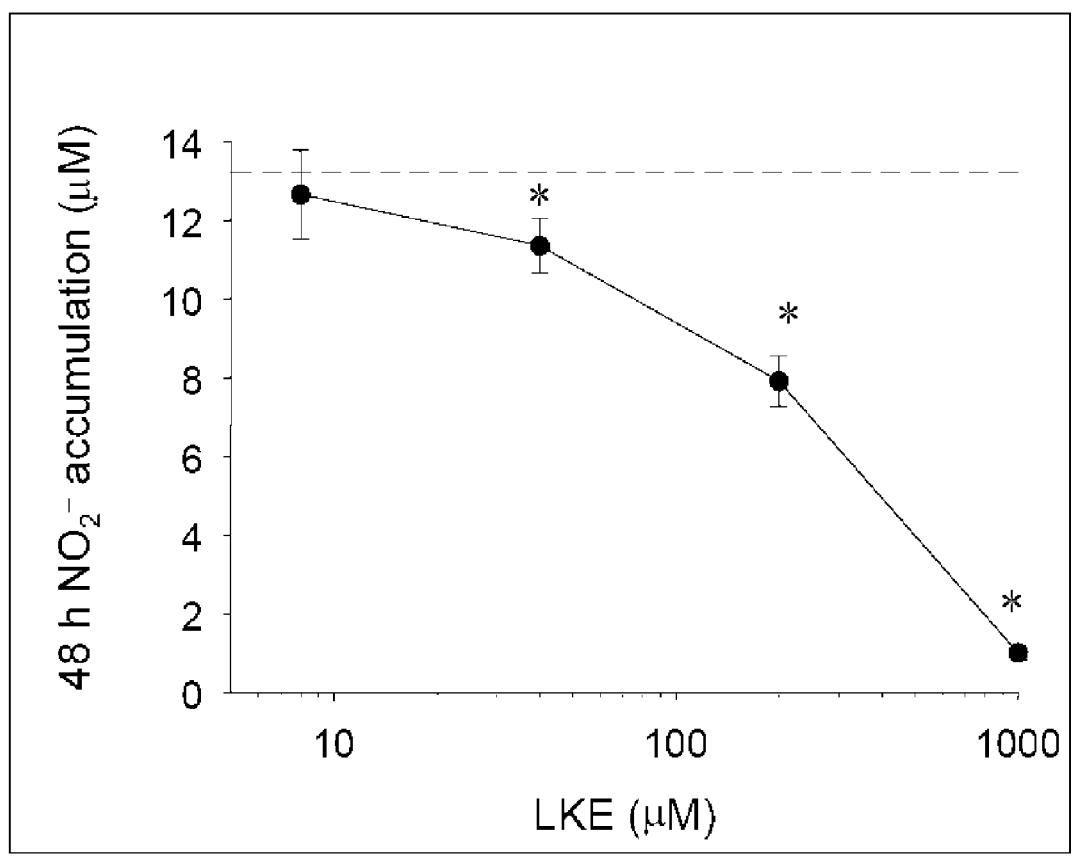
FIG. 7. (R)-LKE1 diminishes LPS sensitivity of Htt+astroglia. (R)-LKE1 was found to reduce the amount of $NO_2^-$ produced by the Htt+astroglia in response to bacterial lipopolysaccharide serotype 0127:B8 (LPS). * means p<0.05, ** means p<0.01. "LKE" refers to (R)-LKE1.
Figure 8:
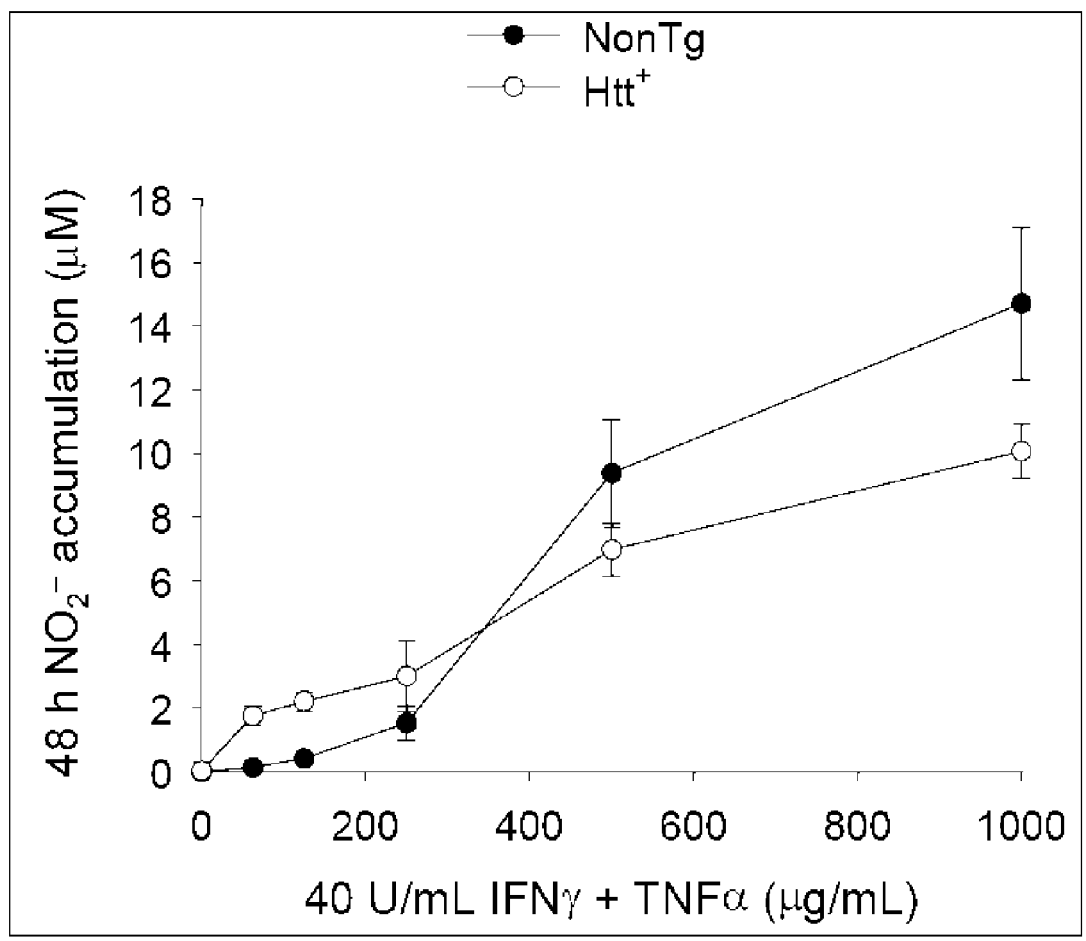
FIG. 8. Similar $NO_2^-$ production of Htt+ and control astroglia as a result of stimulation by 40U/mL IFNγ and TNFα. $NO_2^-$ production was measured after 48 hours of stimulation by a constant concentration of IFNγ+a varied concentration of TNFα.

As shown in FIGS. 7 & 8, the inventor has also demonstrated the efficacy of (R)-LKE1 as an inhibitor of astrocyte activation by an archetypal inflammogen, bacterial lipopolysaccharide (LPS). Astrocytes are a type of glial cell in the brain.

In some embodiments, the compounds of the invention function is a cell-type specific, stimulus-specific, or condition-specific fashion. For example, the inventor found that (R)-LKE1 does not suppress nitrite production in C6 glioma cells stimulated by TNFα+IFNγ. Similarly, (R)-LKE1 was found not to suppress nitrite production in C6 glioma cells stimulated by TNFα+LPS. In contrast, when EOC-20 cells or RAW264.7 macrophages were stimulated with bacterial lipopolysaccharide (LPS; *E. coli* serotype 0127:B8) for 24-48 h and nitrite and cell viability were assessed. LKE inhibited cytokine-induced nitrite accumulation with a similar efficacy in both cell types (see FIGS. 9A & 9B). No cytotoxicity was observed in any of the treatment groups.

Having shown that (R)-LK and (R)-LKE1 inhibits the activation of microglial cells (see e.g. Example 2), the inventor contemplates the use of the compounds of this invention for treating a subject having a condition caused by chronic microglial activation. In certain embodiments, the compounds of this invention may serve as useful compounds for the treatment of numerous CNS conditions, including Alzheimer's dementia, Parkinson's disease, ALS, stroke, and other inflammatory brain diseases. Furthermore, the compounds of this invention may be useful in preventing or treating neurological conditions characterized by either acute or chronic microglial activation.

Treatment of the aforementioned pathologies may comprise administering to a subject a therapeutically effective amount of a compound of this invention, such as those described above or throughout this specification. Treatment may be administered preventively, in advance of a predictable state of excessive microglial activation (e.g., in anticipation of a stroke), or it may be administered therapeutically in settings involving chronic excessive microglial activation and inflammation.

In certain preferred embodiments, lanthionine (optionally in combination with pyruvate), LK or an LK derivative may be administered to a subject (e.g., a human patient) to treat an inflammatory disease and/or suppress inflammation in a subject. In certain embodiments, a second therapeutic compound (e.g., a second anti-inflammatory compound) may be administered to the subject to treat the inflammatory disease and/or suppress inflammation in the subject.

Inflammatory diseases that may be treated with compounds of the present invention include amyotrophic lateral sclerosis (ALS) or similar degenerative motor neuron disease, Alzheimer's disease, Parkinson's disease, Huntington's disease, multiple sclerosis, macular degeneration, a cardiovascular disease, atherosclerosis, rheumatoid arthritis, septic shock or inflammatory bowel disease (IBD).

Compounds of the present invention may be used to alter certain cellular events which are associated with certain inflammatory diseases. For example, in certain embodiments, compounds of the present invention may be used to inhibit or reduce excessive nitric oxide production, which may be associated with certain inflammatory diseases (e.g., Alzheimer's disease, Parkinson's disease, Huntington's disease, ALS, atherosclerosis, rheumatoid arthritis).

In certain embodiments, compounds of the present invention may be used to inhibit or reduce inhibit excessive prostaglandin E2 ($PGE_2$), which may be associated with certain inflammatory diseases (e.g., Alzheimer's disease, Parkinson's disease, Huntington's disease, ALS, atherosclerosis, rheumatoid arthritis, IBD).

In certain embodiments, compounds of the present invention may be used to reduce neurodegeneration associated with excessive glutamate excitotoxicity. Thus diseases associated with excessive glutamate excitotoxicity (e.g., Alzheimer's disease, Parkinson's disease, Huntington's disease, ALS) may be treated with compounds of the present invention.

In certain embodiments, compounds of the present invention may be used to treat diseases that involve activated macrophage cells and/or activated microglia cells. These diseases include many inflammatory diseases, including, for example, Alzheimer's disease, Parkinson's disease, Huntington's disease, ALS, atherosclerosis, rheumatoid arthritis, IBD. In certain embodiments, the disease may involve activated Muller cells (i.e., a type of retinal macrophage cells).

Moreover, in certain embodiments, (R)-LKE1 slows motor neuron disease progression in a murine model of familial amyotrophic lateral sclerosis (ALS), the $SOD1^{G93A}$ mutant mouse, wherein $TNF\alpha$ pathway activation is a salient phenomenon. See, for example, (Hensley et al., 2002; Hensley et al., 2003; West et al., 2004; Hensley et al., 2006), which are all incorporated herein by reference.

F. Protection of Cells from Oxidative Stress and Cytotoxicity

The compounds of the present invention, including the LK derivatives, may be used for treating any disease comprised in part or in whole by a pathological component of oxidative stress. LK and LK derivatives have multiple modes of antioxidant action. For instance the sulfur reacts with peroxides yielding sulfoxides. LK and LK derivatives having carboxylic acids groups, or which are hydrolyzed in vivo to generate carboxylic acid groups, may undergo reactions with peroxides via oxidative decarboxylation reactions, thus magnifying the anti-oxidant potential of the molecule.

In certain embodiments, the invention provides for compounds and methods that may be used to protect cells from oxidative stress and/or cytotoxicity. Oxidative stress and/or cytotoxicity is likely to result from the types of insults likely to the relevant to the pathobiology of neuroinflammatory diseases.

Figure 4:
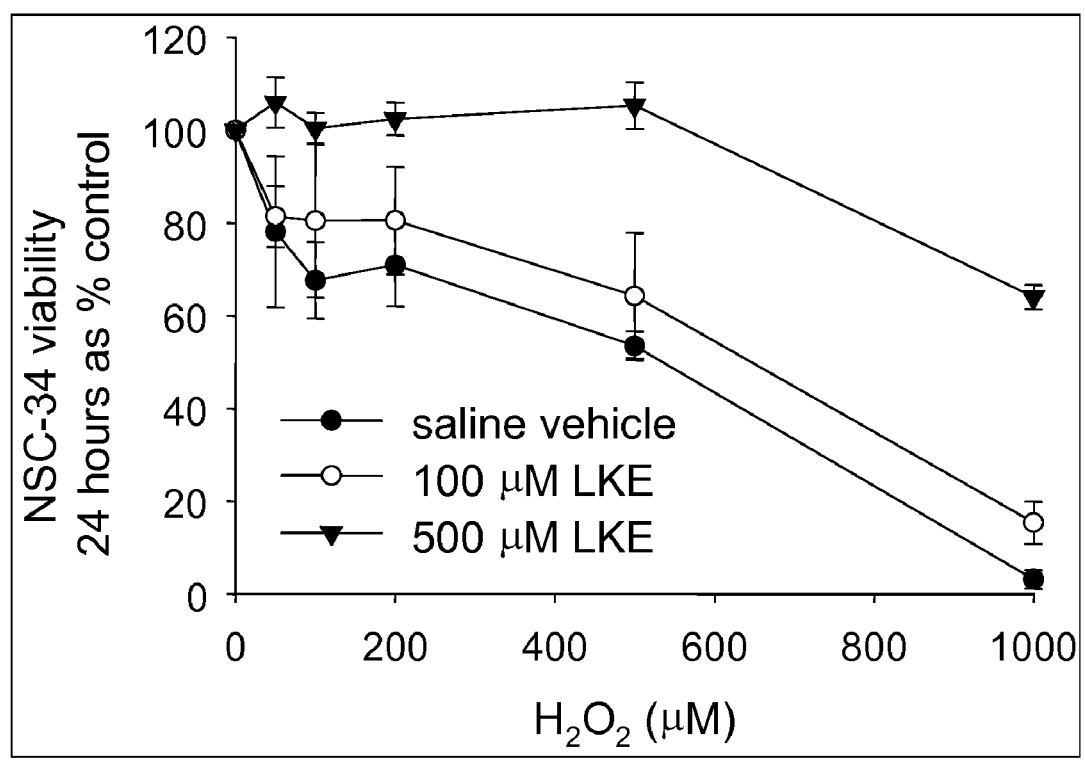
FIG. 4. (R)-LKE1 protects NSC-34 motor neuron-like cells against oxidative challenge. Cells were pretreated 0.5 h with the indicated concentration of (R)-LKE1, then challenged 24 h with $H_2O_2$ at the indicated dose. Viability was assessed by tetrazolium reduction assay. Data indicate mean±SD, N=4 wells/point. "LKE" refers to (R)-LKE1.

For example, in one paradigm studied, the inventor showed that (R)-LKE1 protected NSC-34 motor neuron-like cells from $H_2O_2$-induced cell death and from toxicity associated with exposure to cytokine-stimulated EOC-20 microglia-conditioned medium. Specifically, the inventor demonstrated, that (R)-LK and a synthetic LK ethyl ester derivative, (R)-LKE1, protects NSC-34 motor-neuron like cells from hydrogen peroxide toxicity, a model for oxidative stress. NSC-34 cells were challenged directly with $H_2O_2$ for 24 h and the viability was assessed by tetrazolium reduction assay. In this experiment (R)-LKE1 protected NSC-34 cells from direct oxidative stress-induced cell death in a dose dependent fashion (FIG. 4).

Figure 3:
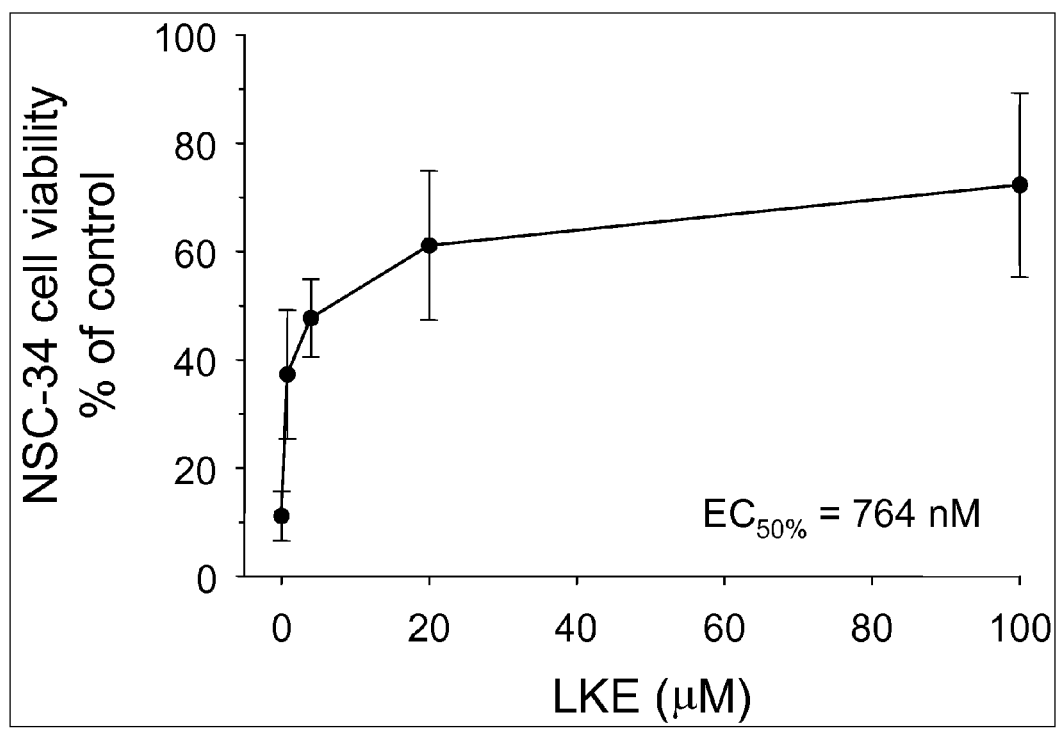
FIG. 3. (R)-LKE1 protects NSC-34 cells against cytotoxicity inherent to cytokine-conditioned EOC-20 microglial cell culture medium. EOC-20 medium was conditioned by stimulating microglia with TNFα+IFNγ for 48 hours. NSC-34 cells were treated 0.5 hours with (R)-LKE1 prior to medium change, then co-treated with (R)-LKE1 (or saline vehicle control) plus conditioned medium for 24 h prior to viability assay by the tetrazolium reduction method. "LKE" refers to (R)-LKE1.

In the second cytotoxicity paradigm, the inventor has also shown that the compounds and methods of this invention diminish the toxicity of microglia-conditioned medium toward NSC-34 cells. NSC-34 cells were treated with conditioned medium taken from EOC-20 cells that had been stimulated for 24 h with 50 U/mL IFNγ plus 40ng/mL $TNF\alpha$. This cytokine-conditioned EOC-20 medium is toxic to NSC-34 cells, whereas the same cytokine mixture added directly to NSC-34 cells is not toxic (data not shown). Medium from unstimulated EOC-20 cells is likewise nontoxic (data not shown). The toxic factor in the cytokine-stimulated EOC-20 cell conditioned medium was not identified. This medium produced significant toxicity to NSC-34 cells that was largely, but not completely mitigated by co-treatment of the motor-neuron like cells with (R)-LKE1 (FIG. 7). The concentration of (R)-LKE1 necessary to achieve half-maximal protective efficacy in this case was less than 1 μM (FIG. 3).

Figure 10:
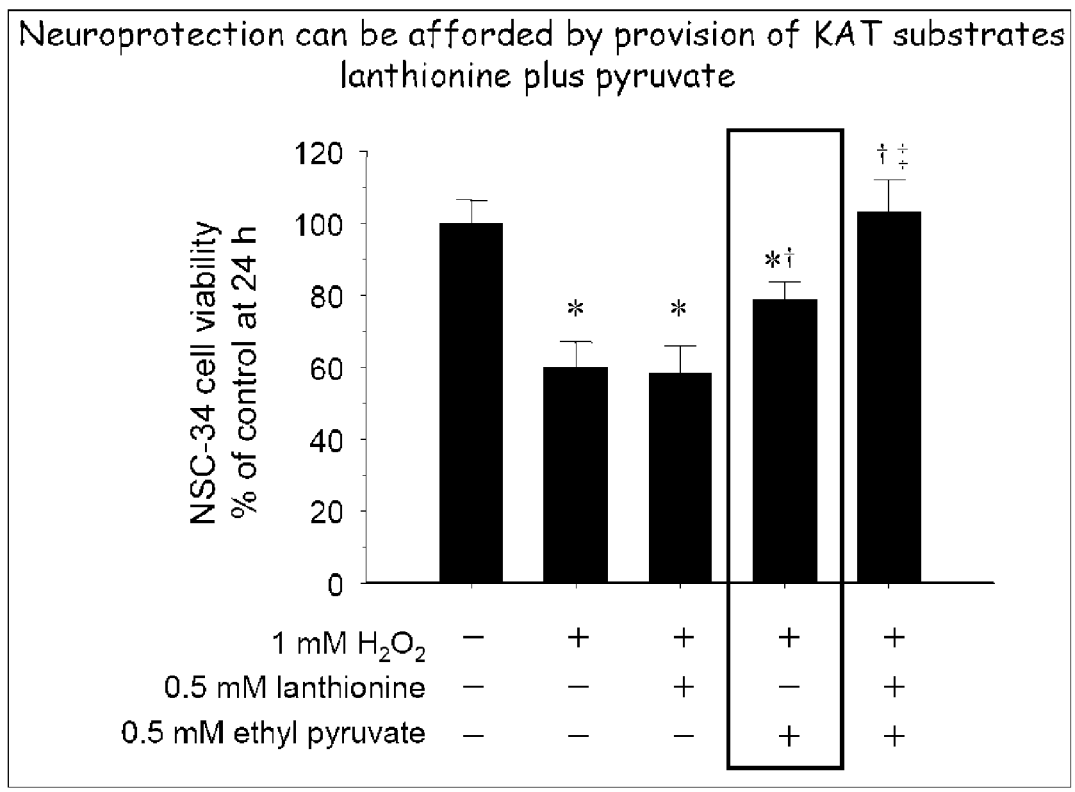
FIG. 10. Ethyl pyruvate and lanthionine synergize to protect NSC-34 motor neuron-like cells against hydrogen peroxide. NSC-34 cells were exposed to 1 mM $H_2O_2$ with or without ethyl pyruvate and/or lanthionine. 0.5 mM lanthionine enhanced the ability of 0.5 mM pyruvate to protect NSC-34 cells from death as a result of exposure to 1 mM $H_2O_2$. Cells were pretreated 6 h with the two compounds prior to challenge with $H_2O_2$. Viability was measured 24 h later. * p<0.05 for the cytotoxic effect, relative to untreated control; †p<0.05 for the cytoprotective effect relative to cells treated with peroxide only; ‡p<0.05 for the combined effect of lanthionine+ethyl pyruvate vs. ethyl pyruvate only.

Furthermore, the invention contemplates that cytoprotection might be achieved by providing metabolic precursors to LK, rather than direct addition of the compound. For example, the inventor has studied the effects of NSC-34 cells treated with ethyl pyruvate in the presence or absence of lanthionine for 6 h prior to challenge with $H_2O_2$ and has assayed the viability of these cells 24 h later (FIG. 10). As reported in previous studies, ethyl pyruvate alone was protective against peroxide-induced cell death (Desagher et al., 1997; Nakamichi et al., 2005) with complete protection at ethyl pyruvate concentrations >1 mM (approximately 2-fold higher than ambient cell culture medium pyruvate concentrations; data not shown). Addition of 0.5 mM ethyl pyruvate afforded significant but partial protection against $H_2O_2$ whereas lanthionine alone had no protective effect (FIG. 8). The combination of ethyl pyruvate plus lanthionine produced synergistic and complete neuroprotection (FIG. 10). This data is consistent with a model wherein lanthionine plus pyruvate are metabolized to form LK (see Scheme 3).

Figure 13:
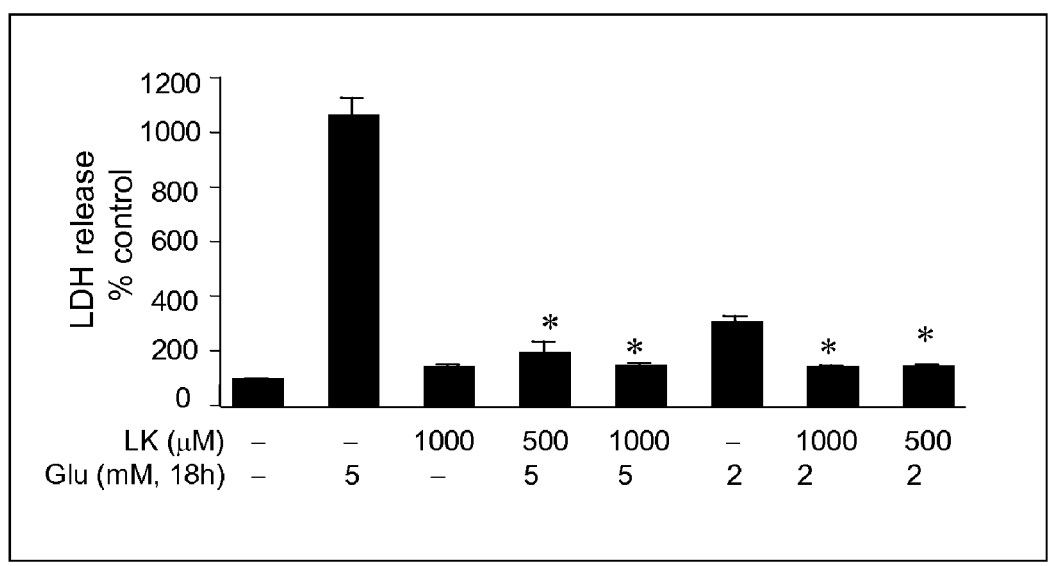
FIG. 13. (R)-LK protects HT4 cells against excitotoxicity. Determination of cell viability: HT4 cells were seeded in 6 well plates ($1 \times 10^7$ cell/well). After 24 h, cell media was changed and (R)-LK (in DMSO) was used for 1 h prior to glutamate challenge. Powdered (R)-LK was dissolved in DMSO just before use. The viability of cells in culture was assessed by measuring the leakage of lactate dehydrogenase (LDH) from cells to media 18-24 h following glutamate treatment using the in vitro toxicology assay kit from Sigma Chemical Co. (St. Louis, Mo., USA). LDH leakage was determined using the following equation: % of total LDH leaked= (LDH activity in the cell culture media/total LDH activity) where total LDH activity=LDH activity in cell monolayer+ LDH activity of detached cells+LDH activity in the cell culture media.
Figure 14:
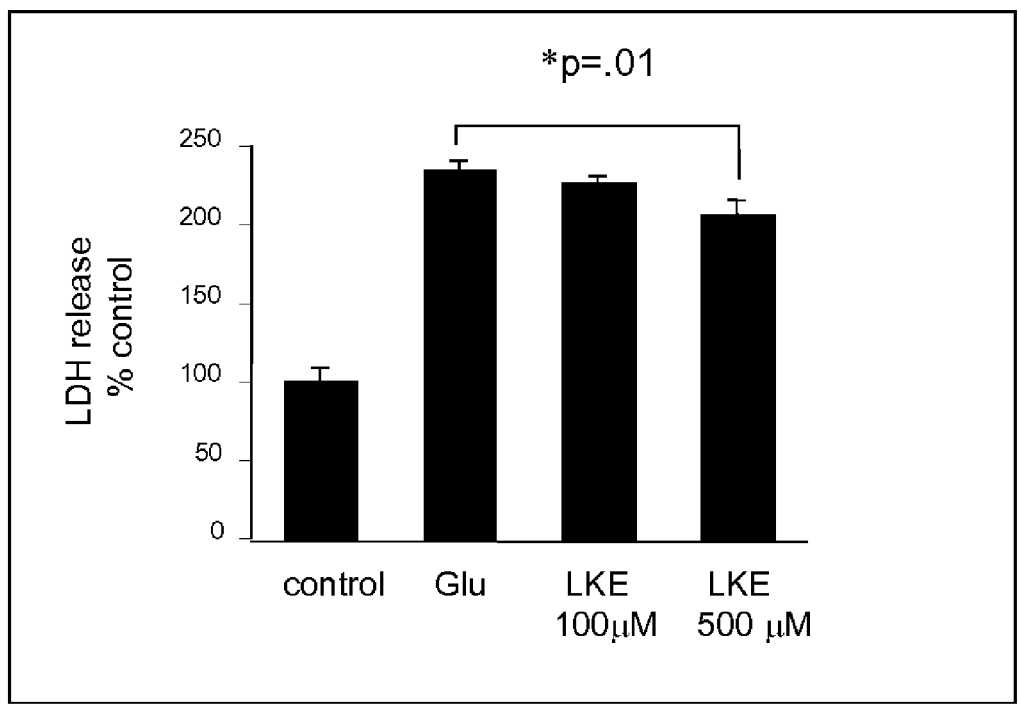
FIG. 14. (R)-LKE1 protects HT4 cells against excitotoxicity. Determination of cell viability. HT4 cells were seeded in 6 well plates ($1 \times 10^7$ cell/well). After 24 h, cell media was changed and (R)-LKE1 (in DMSO) was used for 5 min prior to glutamate challenge. Powdered (R)-LKE1 was dissolved in DMSO just before use. The viability of cells in culture was assessed by measuring the leakage of lactate dehydrogenase (LDH) from cells to media 18-24 h following glutamate treatment using the in vitro toxicology assay kit from Sigma Chemical Co. (St. Louis, USA). LDH leakage was determined using the following equation: % of total LDH leaked= (LDH activity in the cell culture media/total LDH activity) where total LDH activity=LDH activity in cell monolayer+

LK has structural similarity to glutamate in that both compounds contain carboxylate moieties separated by three bond lengths. Since the kynurenine pathway is known to yield kynurenic acid (KYNA), the sole currently-known endogenous anti-exicitotoxin (Moroni, 1999; Foster et al., 1992; Urenjak and Obrenovitch, 2000; Heyes, 1996; Stone and Darlington, 2002), it is plausible to consider that other kynurenine products including LK might act similarly to mitigate glutamate toxicity. In order to test this hypothesis HT4 cells (Sen et al., 2004; Tirosh et al., 2000) were treated with glutamate in the absence or presence of either LK or (R)-LKE1. Toxicity was ascertained by measuring the release of lactate dehydrogenase (LDH) from dead cells into the culture medium. Both LK and (R)-LKE1 significantly diminished glutamate toxicity in this cellular system (FIGS. 13 & 14).

G. Treatment and Prevention of Cancer

In particular, the present invention may be applied to therapy of cancer, such as breast, prostate, lung (SCLC and NSCLC), brain, head & neck, esophagus, trachea, stomach, colon, rectum, uterus, cervix, prostate, liver, pancreas, skin, blood and lymphatic system, testes and ovary. The compounds of this invention may be applied as a single-agent for the treatment of cancer or they may be applied to treat cancer in combination with other agents or methods of treatment. For example, FIG. 16 shows that (R)-LKE1 inhibits tumor cell proliferation in C6 glioma cells.

The invention contemplates that the compounds of the present invention, will function, through one or more of the mechanisms described above, and throughout this application, to induce apoptosis in tumor cells, induce differentiation, inhibit cancer cell proliferation, inhibit inflammatory response, and/or function in a chemopreventative capacity.

H. Other Diseases

Compounds of the present invention (e.g., lanthionine or a composition comprising lanthionine and pyruvate, LK or an LK derivative) may also be used to treat diseases in which KAT/GTK/CCβL activity is deficient. Thus, diseases including hypertension, Huntington's disease, attention deficit disorder, depression (e.g., major depression) or generalized anxiety disorder may be treated with LK or an LK derivative.

In certain embodiments, LK or an LK derivative may be used to treat rhabdomyolysis. Rhabdomyolysis is characterized by the destruction or degeneration of skeletal muscle tissue (as from traumatic injury, excessive exertion, or stroke) that is accompanied by the release of muscle cell contents (as myoglobin and potassium) into the bloodstream resulting in hypovolemia, hyperkalemia, and sometimes acute renal failure. Rhabdomyolysis is the major cause of kidney failure in the U.S., and the disorder is caused by an accumulation of muscle ferroxyl-myoglobin in renal casts. LK or LK derivatives may be particularly useful in the treatment of rhabdomyolysis due to the facile redox chemistry of the sulfur in these ketimines.

The invention contemplates that the compounds of this invention may be useful for the treatment of sepsis or sepsis-related diseases. The inventor has shown (see Example 6) that mice co-treated with (R)-LKE1 had a higher chance of surviving the LPS model conditions. Also, in an "ex vivo" assay (see Example 7), the inventor has shown that (R)-LKE1 inhibits peripheral monocyte TNFα production in human blood, triggered by either lipopolysaccharide or bacterial peptidoglycan.

The invention also contemplates that the compounds of this invention may be useful for the treatment and/or prevention of stroke. One reason why the compounds of this invention, (e.g. LK, (R)-LKE1, etc.) are expected to help prevent stroke is that the compounds of this invention function as anti-oxidants, and many antioxidants have been shown to protect prevent stroke in various stroke models.

Another reason why compounds of this invention, (e.g. LK, (R)-LKE1, etc.) are expected to help prevent stroke, is that the compounds of this invention function as glutamate and/or excitotoxin antagonists, and because many compounds that have been shown to function as glutamate and/or excitotoxin antagonists have been shown to help prevent stroke. For example, LK and (R)-LKE1 were shown by the inventor to protect HT4 neurons against glutamate toxicity (see FIGS. 13 & 14).

VI. Combination Therapy

In addition to being used as a monotherapy, lanthionine, lanthionine ketimine (LK), an LK derivative of the present invention, thiomorpholine dicarboxylic acid (TMDCA), and a TMDCA derivative of the present invention, will also find use in combination therapies. Such combination therapies may include the use of anti-inflammatory agents generally, or inhibitors of COX-2 and/or iNOS. Alternatively, the combination may be include a second anti-cancer therapy, as discussed in detail below.

An "anti-cancer" agent is capable of negatively affecting cancer in a patient, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with lanthionine, LK, a LK derivative of the current invention, TMDCA, and/or a TMDCA derivative of the current invention and the other agent(s) at the same time. This may be achieved by contacting the cell with a single composition or pharmacological formulation that includes both agents, or by contacting the cell with two distinct compositions or formulations, at the same time, wherein one composition includes lanthionine, LK, a LK derivative of the current invention, TMDCA, and/or a TMDCA derivative of the current invention and the other includes the second agent(s).

Alternatively, a therapy using lanthionine, LK, a LK derivative of the current invention, TMDCA, and/or a TMDCA derivative of the current invention, may precede or follow the other agent treatment by intervals ranging from minutes to weeks. In embodiments where the other agent and expression construct are applied separately to the cell, one would generally ensure that a significant period of time did not expire between the time of each delivery, such that the agent and the lanthionine, LK, LK derivative, TMDCA, and/or TMDCA derivative would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several days (2, 3, 4, 5, 6 or 7) to several wk (1, 2, 3, 4, 5, 6, 7 or 8) lapse between the respective administrations.

Various combinations may be employed, lanthionine, LK, LK derivative, TMDCA, and/or TMDCA derivative therapy is "A" and the secondary agent, such as radio- or chemotherapy, is "B":

```
A/B/A  B/A/B  B/B/A  A/A/B  A/B/B  B/A/A  A/B/B/B
B/A/B/B  B/B/B/A  B/B/A/B  A/A/B/B  A/B/A/B
A/B/B/A  B/B/A/A  B/A/B/A  B/A/A/B  A/A/A/B
B/A/A/A  A/B/A/A  A/A/B/A
```

Administration of the lanthionine, LK, LK derivative, TMDCA, and/or TMDCA derivative compounds of the present invention to a patient will follow general protocols for the administration of chemotherapeutics, taking into account the toxicity, if any, of the drug. It is expected that the treatment cycles would be repeated as necessary. It also is contemplated that various standard therapies, as well as surgical intervention, may be applied in combination with the described hyperproliferative cell therapies.

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tk) gene, when delivered to brain tumors by a retroviral vector system, successfully induced susceptibility to the antiviral agent ganciclovir (Culver et al., 1992). In the context of the present invention, it is contemplated that lanthionine, LK, LK derivative, TMDCA, and/or TMDCA derivative therapy could be used similarly in conjunction with chemotherapeutic, radiotherapeutic, or immunotherapeutic intervention, in addition to other pro-apoptotic or cell cycle regulating agents, as discussed below.

A. Krebs Cycle α-keto Acids

As discussed in part above, certain Krebs cycle α-keto acids have been found to have antioxidant properties and may be used in combination with the present invention. Pyruvate and α-ketoglutarate are Krebs cycle α-keto acids which are shown in the Examples section, below, to have antioxidant properties.

Pyruvate is a key intermediate in the glycolytic and pyruvate dehydrogenase pathways, which are involved in biological energy production. Pyruvate is widely found in living organisms. Pyruvate is typically consumed in the diet. The average daily intake of this substance typically ranges between about 100 milligrams and 1 to 2 grams. Certain fruits and vegetables are rich in pyruvate. For example, a red apple typically contains approximately 450 milligrams of pyruvate. Dark beer and red wine are also rich sources of pyruvate.

"Pyruvate" or "pyruvic acid", are used herein, refer to a compound having the structure $CH_3—C(O)—COOH$ and salts thereof. Pyruvate is also known as 2-oxopropanoate, α-ketopropionate, acetylformate and pyroracemate. "Pyruvate," as used herein, includes pyruvic acid and the anion of pyruvic acid.

An "ester derivative of pyruvate" refers to compounds having the structure:

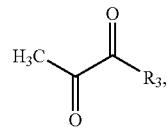

wherein $R_3$ is a heteroatom substituted or unsubstituted version of $C_1$-$C_{10}$-alkoxy, $C_2$-$C_{10}$-alkenylamino, $C_2$-$C_{10}$-alkynylamino, $C_1$-$C_{10}$-aryloxy, or $C_2$-$C_{10}$-aralkoxy, and pharmaceutically acceptable salts, hydrates, and optical isomers thereof.

An "amide derivative of pyruvate" refers to compounds having the structure:

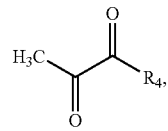

wherein $R_4$ is a heteroatom substituted or unsubstituted version of $C_1$-$C_{10}$-alkylamino, $C_2$-$C_{10}$-alkenylamino, $C_2$-$C_{10}$-alkynylamino, $C_1$-$C_{10}$-arylamino, or $C_2$-$C_{10}$-aralkylamino, and pharmaceutically acceptable salts, hydrates, and optical isomers thereof.

In certain embodiments, lanthionine, LK, LK derivative, TMDCA, TMDCA derivative, and/or additional agents, may be administered to a subject (e.g., a human patient) in combination with a second anti-inflammatory compound (e.g., an antioxidant, pyruvate, α-ketoglutarate). Administering both pyruvate in combination with lanthionine, LK, LK derivative, TMDCA, TMDCA derivative, and/or additional agents, to a subject may facilitate the production of lanthionine ketimine in the subject. The in vivo synthesis of lanthionine ketimine from pyruvate and lanthionine is described above.

Doses of pyruvate that may be administered to a subject may vary; for example, in certain embodiments, from about 0.5 g/day to 200 g/day, more preferably from about 1 g/day to about 100 g/day, more preferably from between about 1 g/day to about 75 g/day may be administered to a subject. In certain embodiments, about 1-10 g/day may be administered to a subject. In certain embodiments, the pyruvate is administered orally as a dietary supplement.

B. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

C. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

D. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with lanthionine, LK, LK derivative, TMDCA, and/or TMDCA derivative therapy. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

E. Gene Therapy

In yet another embodiment, the secondary treatment is a secondary gene therapy in which a therapeutic polynucleotide is administered before, after, or at the same time as lanthionine, LK, LK derivative, TMDCA, and/or TMDCA derivative. Therapeutic genes may include an antisense version of an inducer of cellular proliferation (sometimes called an oncogene), an inhibitor of cellular proliferation (sometimes called a tumor suppressor), or an inducer of programmed cell death (sometimes called a pro-apoptotic gene).

F. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

G. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the compounds of the present invention, may upregulate the expression of cell surface receptors involved in apoptotic signaling (e.g., DR4 and DR5) and may therefore have additive or synergistic effects in combination with ligands for these receptors (e.g., TRAIL; see Hyer et al., 2005, which is incorporated herein by reference). The upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increasing intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

H. Anti-inflammatory Agents

It is contemplated that other anti-inflammatory agents will be used in conjunction with lanthionine, LK, a LK derivative of the current invention, TMDCA, and/or a TMDCA derivative of the current invention. Other COX inhibitors may be used, including arylcarboxylic acids (salicylic acid, acetylsalicylic acid, diflunisal, choline magnesium trisalicylate, salicylate, benorylate, flufenamic acid, mefenamic acid, meclofenamic acid and triflumic acid), arylalkanoic acids (diclofenac, fenclofenac, alclofenac, fentiazac, ibuprofen, flurbiprofen, ketoprofen, naproxen, fenoprofen, fenbufen, suprofen, indoprofen, tiaprofenic acid, benoxaprofen, pirprofen, tolmetin, zomepirac, clopinac, indomethacin and sulindac) and enolic acids (phenylbutazone, oxyphenbutazone, azapropazone, feprazone, piroxicam, and isoxicam. (U.S. Pat. No. 6,025,395)

Histamine H2 receptor blocking agents, including cimetidine, ranitidine, famotidine and nizatidine, may also be used in conjunction with the compounds of the current invention.

I. Anti-cholinesterase Inhibitors

Treatment with acetylcholinesterase inhibitors such as tacrine, donepizil, metrifonate and rivastigmine for the treatment of Alzheimer's and other disease in conjunction with lanthionine, LK, a LK derivative of the current invention, TMDCA, and/or a TMDCA derivative of the current invention is contemplated. Other acetylcholinesterase inhibitors may be developed which may be used once approved include rivastigmine and metrifonate. Acetylcholinesterase inhibitors increase the amount of neurotransmitter acetylcholine at the nerve terminal by decreasing its breakdown by the enzyme cholinesterase.

J. Estrogen Replacement Therapy

Estrogen replacement therapy (ERT) can be used in conjunction with lanthionine, LK, a LK derivative of the current invention, TMDCA, and/or a TMDCA derivative of the current invention for the treatment of Alzheimer's and other diseases. Estrogen is an excellent neuroprotective agent and effects multiple pathways that are involved in the pathogenisis of diseases that also involve excessive production of either nitric oxide (NO) or prostaglandins.

K. MAO-B Inhibitors

MAO-B Inhibitors such as selegilene (Eldepryl or Deprenyl) may be used in conjunction with lanthionine, LK, a LK derivative of the current invention, TMDCA, and/or a TMDCA derivative of the current invention of the current invention. Selegilene is used for Parkinson's disease and irreversibly inhibits monoamine oxidase type B (MAO-B). Monoamine oxidase is an enzyme that inactivates the monoamine neurotransmitters norepinephrine, serotonin and dopamine.

L. Pharmaceutical Agents for MS

Common drugs for multiple sclerosis (MS) that can be used in combination with the triterpenoid derivatives include immunosuppressive drugs such as azathioprine (Imuran), cladribine (Leustatin), and Cyclophosphamide (Cytoxan).

M. Supplements

Dietary and nutritional supplements with reported benefits for treatment or prevention of Parkinson's, Alzheimer's, multiple sclerosis, amyotrophiclateral sclerosis, rheumatoid arthritis, inflammatory bowel disease, and all other diseases whose pathogenesis is believed to involve excessive production of either nitric oxide (NO) or prostaglandins, such as acetyl-L-carnitine, octacosanol, evening primrose oil, vitamin B6, tyrosine, phenylalanine, vitamin C, L-dopa, or a combination of several antioxidants may be used in conjunction with lanthionine, LK, a LK derivative of the current invention, TMDCA, and/or a TMDCA derivative of the current invention.

VII. Examples

The following examples are included to demonstrate specific embodiments of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Synthesis of (R)-LK and (R)-LKE1

(R)-LKE1 was synthesized according to the following Scheme:

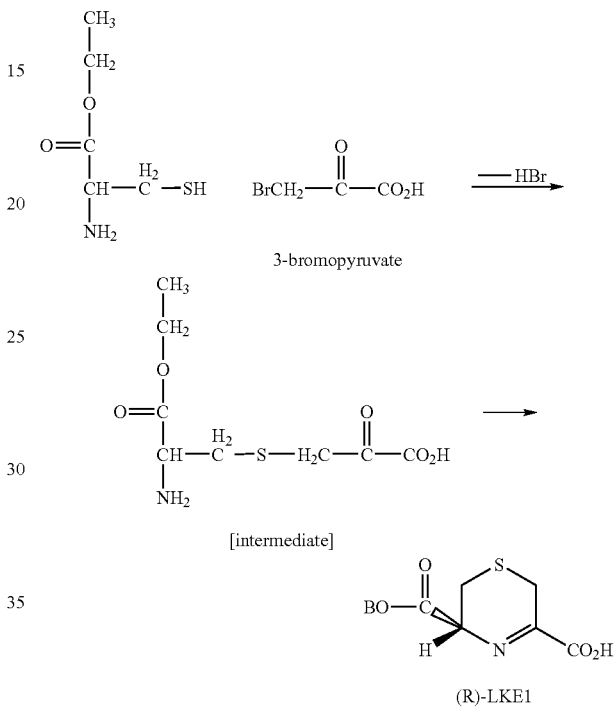

Equal volumes of 5% aqueous L-cysteine hydrochloride with 5% aqueous 3-bromopyruvate were mixed at ambient temperature. The resulting pearly white precipitate was filtered, washed thoroughly in deionized water, and recrystallized in warm 10% methanol. Purity was ascertained by high performance liquid chromatography (HPLC), $^1$H-NMR and mass spectrometry. Product was dried under $N_2(g)$ and dissolved in either DMSO or 0.1 N saline. In the latter case, the solution was made by dropwise addition of 2 N NaOH to pH 7.4. Saline solutions of LK and LKE were sparged with $N_2(g)$ and stored in aliquots at −80° C. until ready for use.

Example 2

Inhibition of Inflammatory Response in Microglial Cells

Mouse EOC-20 microglia (American Tissue Type Collection, Gaithersville Md. USA) (Hensley et al., 2003; Walker et al., 1995) were grown in DMEM containing 20% L929 fibroblast-supplemented medium. Nitrite production by cytokine stimulated microglia was measured in cell culture medium using the Griess diazotization reaction as previously reported (Hensley et al., 2003; West et al., 2004).

The efficacy of (R)-LKE1 and (R)-LK as inhibitors of microglial cell activation in response to pro-inflammatory cytokines is shown in FIGS. 1A & 1B. EOC-20 murine microglial cells were pretreated 30 minutes with test compounds (e.g. (R)-LK or (R)-LKE1) dissolved in DMSO and diluted 1:200 into cell culture medium; or with DMSO vehicle only. Cells were then challenged with cytokine and allowed to incubate undisturbed in the cell culture incubator for 24 h prior to Griess assay. The lanthionine ketimine ester in this case is the structure shown above as (R)-LKE1. After drug treatment cells were then stimulated with 40 ng/mL recombinant murine tumor necrosis factor alpha (TNF α) plus 50U/mL interferon gamma (IFNγ). Nitrite ($NO_2^-$) was measured in the cell culture medium 24 hours later, as an index of nitric oxide production. Cell viability was then assayed in the same cultures using a commercially available tetrazolium reduction assay (Promega OneStep™; Promega, Gaithersburg Md.). Cell culture methods were those published by the inventor (Hensley et al., 2003; West et al., 2004).

The Dose response relationship for (R)-LKE1 inhibition of TNFα (20ng/mL)+IFNγ (50 U/mL)-stimulated nitrite production by activated EOC-20 microglia is shown in FIG. 2. Cells were pretreated 30 minutes with the indicated concentration of (R)-LKE1 prior to cytokine challenge. Nitrite was measured in the cell culture medium 24 hrs later.

Dose response for (R)-LKE1 inhibition of TNFα (20ng/mL)+IFNγ (50 U/mL)-stimulated nitrite production by activated EOC-20 microglia is shown in FIG. 1B. Cells were pretreated 20 hours with the indicated concentration of (R)-LKE1 prior to cytokine challenge. Nitrite was measured in the cell culture medium 24 hours later. *P<0.05; **P<0.01 by Student's t-test. These results demonstrate a promising level of potency and efficacy for the inhibition of inflammatory responses by LK derivatives.

(R)-LKE1 protects NSC-34 motoneuron hybridoma cells from microglial-derived neurotoxic products (FIG. 3). EOC-20 microglia were stimulated with 50 U/mL IFNγ plus 20ng/mL TNFα for 24 hours, and cytokine-conditioned medium (CM) was collected. NSC-34 cells (2 days post-passage) were treated with the indicated concentration of (R)-LKE1 for 2.5 hours after which 50% of the medium was replaced with CM. Control cells received "naïve," unconditioned EOC-20 medium (NM). Enough (R)-LKE1 was added to replace that removed during partial medium replacement. After 48 hours, viability of NSC-34 cultures was assessed by tetrazolium reduction assay using a commercially available kit (Promega Aqueous OneStep®). Data indicate mean±SD, N=4 wells of cells in a representative experiment.

(R)-LKE1 protects NSC-34 motoneuron x neuroblastoma hybrid cells from hydrogen peroxide toxicity (FIG. 4). Cells were treated with the indicated concentration of (R)-LKE1. Thirty minutes later cells were challenged with the indicated concentration of hydrogen peroxide. Cell viability was assayed 24 hours later by tetrazolium reduction using a commercially available kit (Promega).

Figure 5:
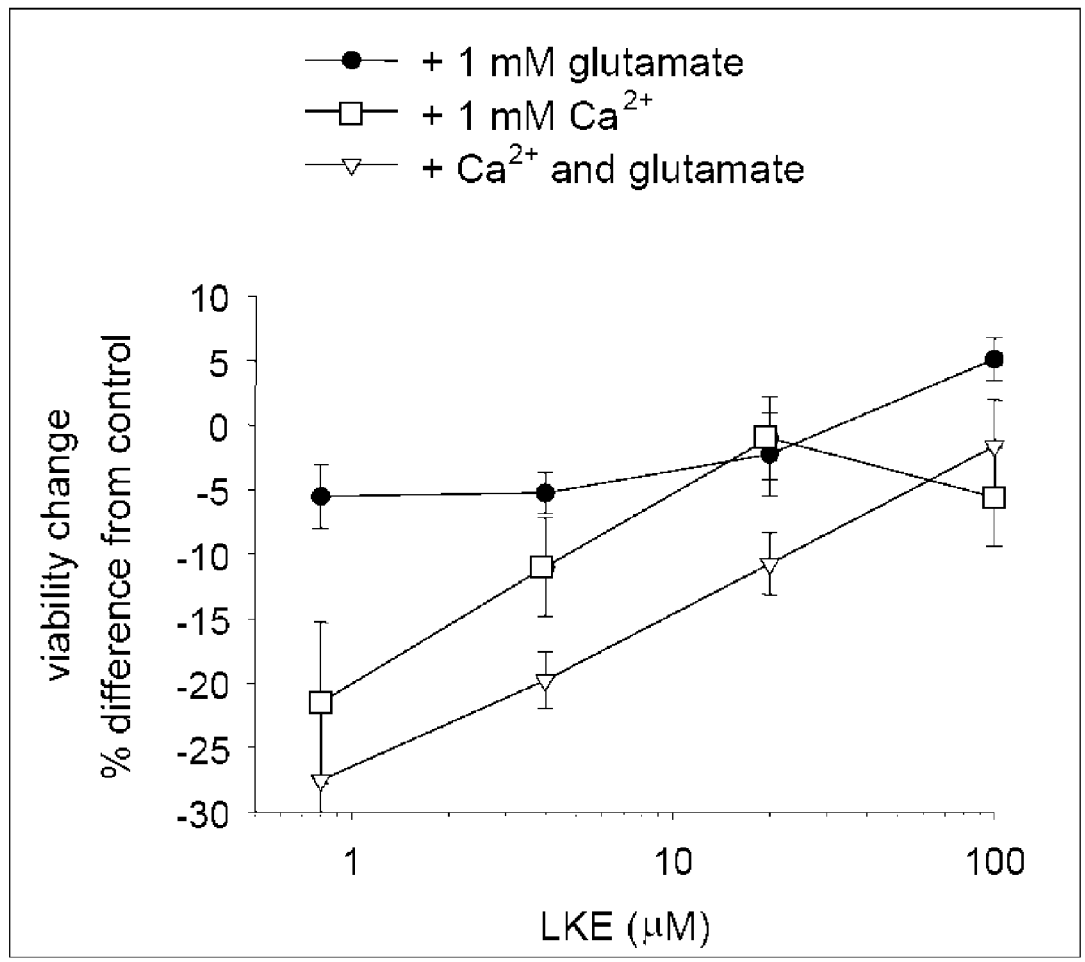
FIG. 5. (R)-LKE1 protects NSC-34 cells against excitotoxicity. Dose response for (R)-LKE1 measured as a function of change in viability of cells exposed to glutamate and/or $Ca^{2+}$. "LKE" refers to (R)-LKE1

(R)-LKE1 increases the viability of NSC-34 motoneuron x neuroblastoma hybrid cells exposed to glutamate and/or $Ca^{2+}$ (FIG. 5). NSC-34 motor neuron x neuroblastoma cells were treated with 1 mM L-glutamate, 1 mM $CaCl_2$, or both for four days. (R)-LKE1 was added at t=0 and at t=48 hours, at the indicated concentrations. At the end of four days (t=96 hours) cell viability was assayed by measuring tetrazolium reduction rates using a commercially available kit (Promega).

In a EOC-20 microglial assay the cells were stimulated with TNFα in the presence or absence of 100 microM (R)- or (S)-LK, and nitrite was measured 24 h later, the net suppression of nitrite was 13% by (S)-LK and 15% by (R)-LK. These results are similar to results observed previously with (R)-LK and demonstrate that both isomers have efficacy.

The reduced lanthionine ketimine (i.e., TMDCA) was also tested against TNFα-stimulated nitrite production in the EOC-20 screen. 100 microM TMDCA (formed from cyanoborohydride reduction of LK) suppressed microglial activation to 67.5+/−3.8% (SD) of the maximum, or about 32.5% inhibition of the cytokine effect.

Example 3

(R)-LKE1 Inhibits Inflammatory Responses in Astroglial Cells and Macrophages

Primary astrocytes were cultured from neonatal R6/2 transgenic mouse pups ("Htt+") which are the standard murine model for Huntington's disease (animals commercially obtained from Jackson Labs) or nontransgenic littermates. For RAW cell studies, RAW264.7 macrophages were obtained commercially from American Type Culture Collection. RAW 264.7 macrophages were grown in DMEM plus 10% FBS and 1% Pen/Strep. Cells were maintained in culture according to published methods. Cells were treated with +/−1 µg/mL bacterial lipopolysaccharide serotype 0127:B8 (Sigma Chemical)+/−various concentrations of (R)-LKE1 for 24-48 h. (R)-LKE1 was added 30 minutes prior to LPS challenge. Nitrite was measured in the cell culture medium using the Griess diazotization assay. Cells were lysed and Western blots performed for protein expression or in other experiments for ribonuclease protection assays.

Figure 6:
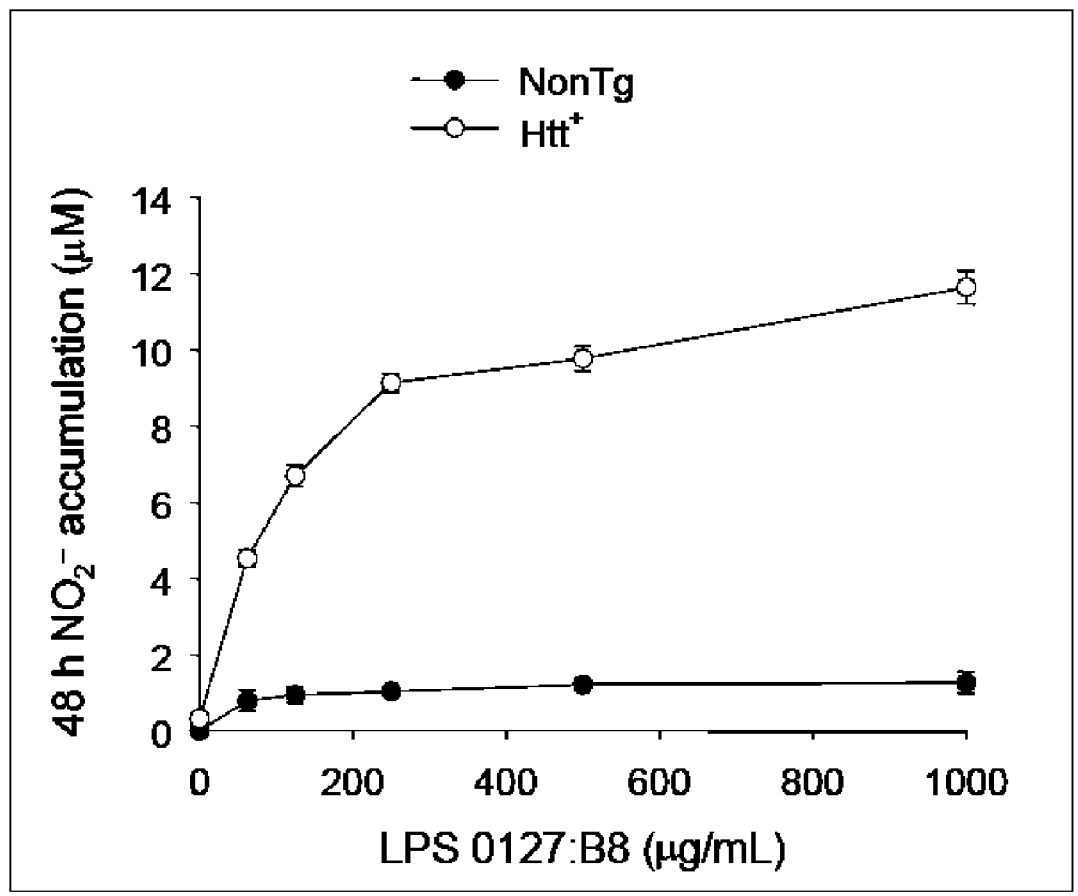
FIG. 6. Htt+astroglia super-induce iNOS in response to LPS. It was found that Htt+astroglia super-induce iNOS in response to bacterial lipopolysaccharide serotype 0127:B8 (LPS), as measured by $NO_2^-$ accumulation at 48 hours after exposure to LPS.

The Htt+ astroglia were found to super-induce iNOS in response to bacterial lipopolysaccharide serotype 0127:B8 (LPS), as confirmed using Western blot and as measured by $NO_2^-$ accumulation (FIG. 6). (R)-LKE1 was found to reduce the amount of $NO_2^-$ produced by the Htt+astroglia in response to LPS (FIG. 7). In contrast, the $NO_2^-$-production of Htt+ and control astroglia were similar as a result of stimulation by 40 U/mL IFNγ+TNFα (0-1000 µg/mL); $NO_2^-$ production was measured at 48 hours after stimulation by IFNγ+TNFα (FIG. 8). As a result of stimulation by IFNγ and TNFα, similar increases in iNOS were observed in Htt+ and control astrocytes as measured by Western blot. These results demonstrate that (R)-LKE1 can inhibit LPS-induced $NO_2^-$ production in Htt+ astroglia.

Figures 9A, 9B:
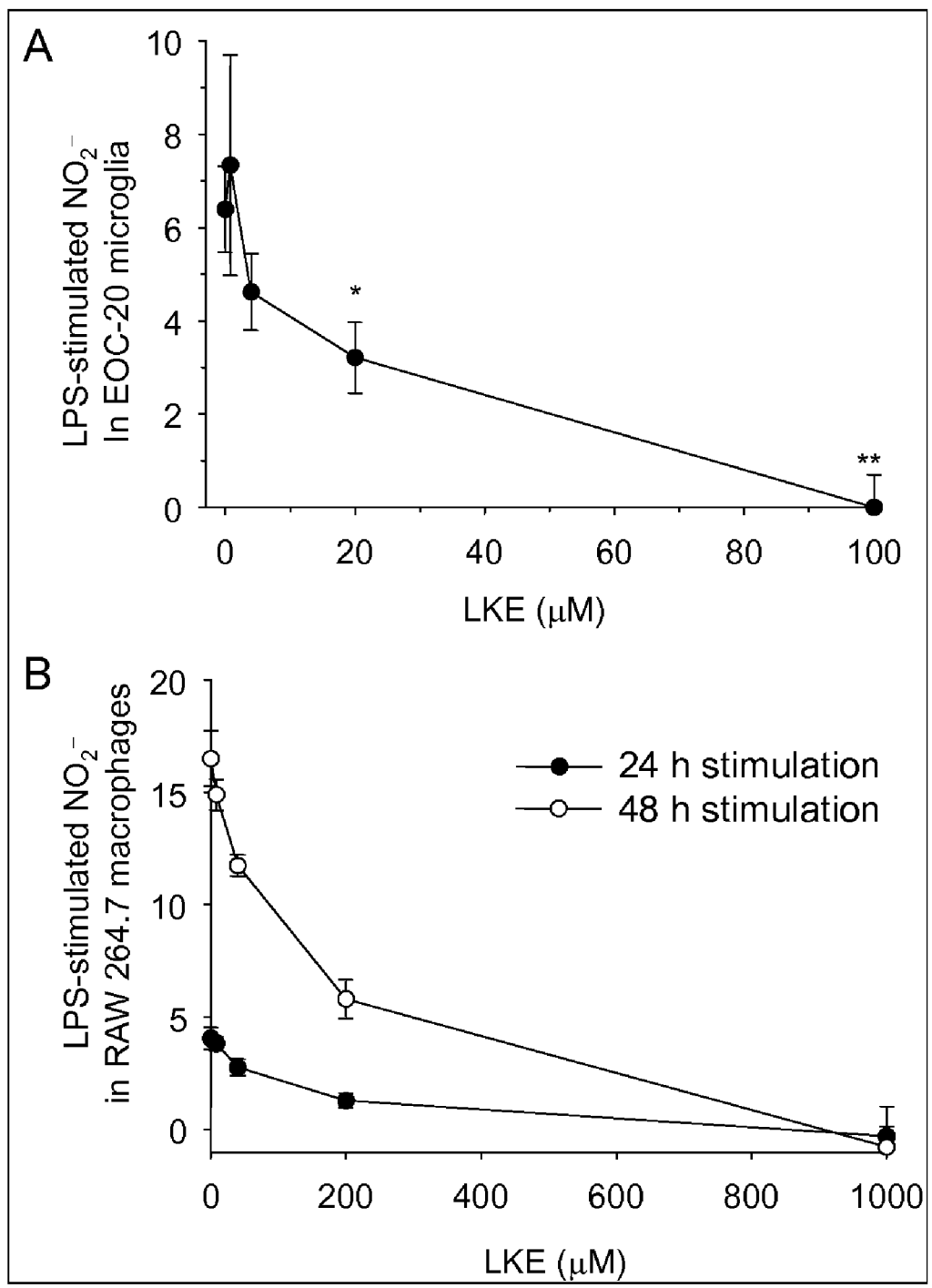
FIGS. 9A & 9B. (R)-LKE1 suppresses LPS-stimulated nitrite production. Error bars indicate mean±SD, N=4 wells from a typical experiment. *p<0.05; **p<0.01 by two-tailed t-test. "LKE" refers to (R)-LKE1.

Experiments were then performed on RAW 264.7 macrophages (R)-LKE1 would inhibit LPS-stimulated nitric oxide production. As shown in FIGS. 9A and 9B, (R)-LKE1 inhibited LPS stimulated nitric oxide production in RAW 264.7 macrophages and EOC-20 microglial cells across a variety of concentrations. In contrast, (R)-LKE1 was not observed to suppress nitric oxide production in C6 glioma cells (as stimulated using LPS or IFN-γ), and (R)-LKE1 was also not observed to suppress PGE2 in (TNF-α+INFγ) stimulated EOC-20 cells. These and the above experiments demonstrate that (R)-LKE1 acts selectively and in a cell-type specific fashion.

Example 4

NSC-34 Cells are Protected from Free Radical Damage by Lanthionine and Ethyl Pyruvate NSC-34 motor neuron-like cells, derived through the fusion of a neuroblastoma cell line with embryonic mouse motor neurons (Cashman et al., 1992), were grown in Dulbecco's modified essential medium (DMEM) plus 5% fetal bovine serum (FBS) and 1% penicillin plus 1% streptomycin (Pen/Strep). Recombinant TNFα and interferon gamma (IFNγ) were purchased from BD Biosciences (Pasadena Calif. USA). Lanthionine was purchased from *Sequoia* Research Products Ltd. (Pangbourne, UK). All other reagents were of the highest available commercial purity.

NSC-34 cells were exposed to 1 mM $H_2O_2$ with or without ethyl-pyruvate and/or lantionine (LK). As shown in FIG. 10, 0.5 mM lanthionine enhanced the ability of 0.5 mM of ethyl pyruvate to protect NSC-34 cells from death as a result of exposure to 1 mM $H_2O_2$. These results indicate the utility of inhibiting free radical damage to a neuron by contacting the cell with LK and pyruvate.

Example 5

(R)-LKE1 Alleviates ALS Symptoms in an ALS Mouse Model

Transgenic mice. Mice expressing high copy numbers of human mutant G93A-SOD1 ($SOD1^{G93A}$ mice) were obtained from Jackson Laboratories [Bar Harbor Me. USA; strain designation B6SJL-TgN-(SOD1 G93A)-1-Gur] (Hensley et al., 2002; Hensley et al., 2003; West et al., 2004; Hensley et al., 2006). Transgenic mice were maintained in the hemizygous state by mating $SOD1^{G93A}$ males with B6SJL-TGN females. Animals were housed in the Oklahoma Medical Research Foundation Laboratory Animal Resource Center.

Mice were trained to a rotarod task at 80 d of age. In this task mice were placed on a horizontal rod that rotates with acceleration at 10 rpm from rest (Hensley et al., 2002; Hensley et al., 2003; West et al., 2004). The time was recorded at which each mouse fell from the rotarod and the test was repeated four times on each trial date. The closest three performance times were averaged for each mouse on each day. For experimental drug treatments mice were injected with LKE at 100 mg/kg/day i.p. Monday-Friday beginning at 90 d. Control animals received saline vehicle. Rotarod performance and weights were recorded at 10 day intervals until death. Animals were euthanized when unable to right themselves within 10 seconds of being placed on their side, or when unable to perform the rotarod task.

R6/2 or nontransgenic pups were allowed to mature and were assessed for neurochemical integrity by image-guided magnetic resonance spectrometry (IG-MRS) at 70-80 days of age, in collaboration with Dr. Rheal Towner and Dr. Yasvir Tesiram at the OMRF. In ongoing experiments, R6/2 mice are being administered (R)-LKE1 100 mg/kg 5 days/week in saline starting at 35 days of age. IG-MRS will be used to monitor neurochemical integrity at 70 days of age and later.

Figure 11:
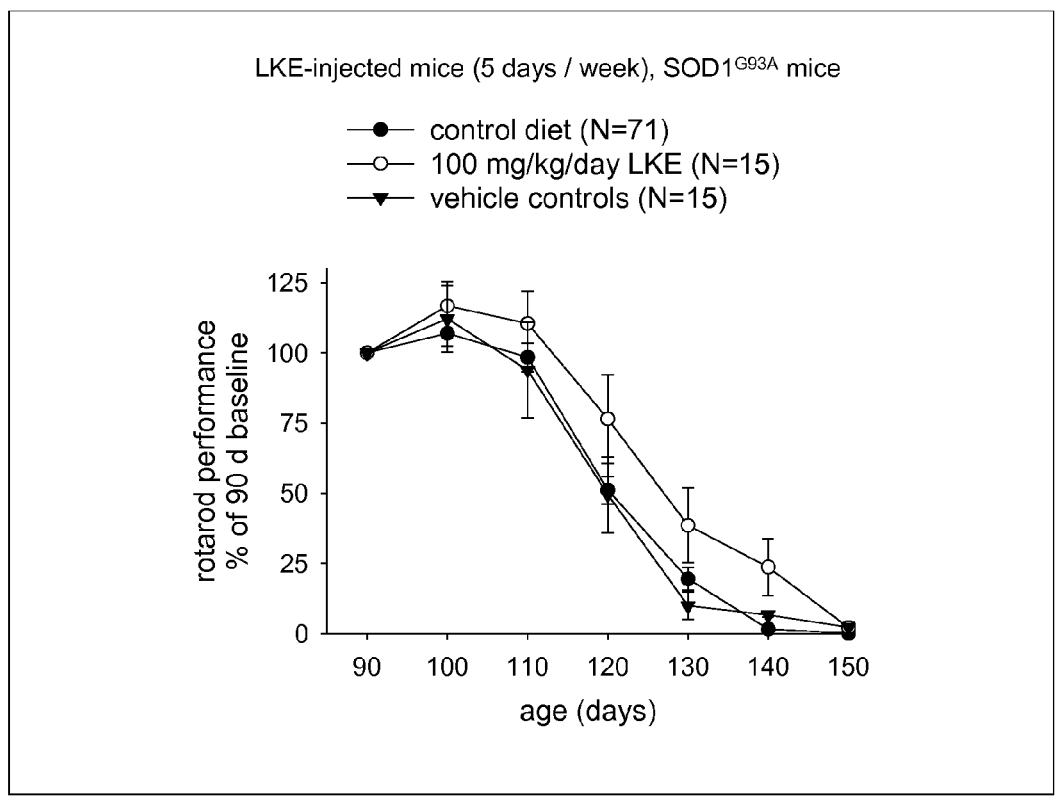
FIG. 11. (R)-LKE1 slows progression of motor neuron disease in G93A-SOD1 mice. Mice were administered LKE in saline at 100 mg/kg i.p. 5 days/week beginning at 90 d, or saline vehicle only. The graphs shows motor performance decline patterns as measured by a rotarod performance assay. There are 2 control curves here; a vehicle-injected set of G93A-SOD1 (ALS) mice and a group of the same mice fed the basal diet but not injected or treated. Both curves overlap perfectly with a very large "N" for the diet-fed animals. The LKE-injected animals clearly display a right-shifted rotarod curve. P<0.05 by repeated measures ANOVA; *P<0.05 by post-hoc t-tests at the indicated age points. Rotarod performance in improved as a result of (R)-LKE1 administration. "LKE" refers to (R)-LKE1.
Figure 12:
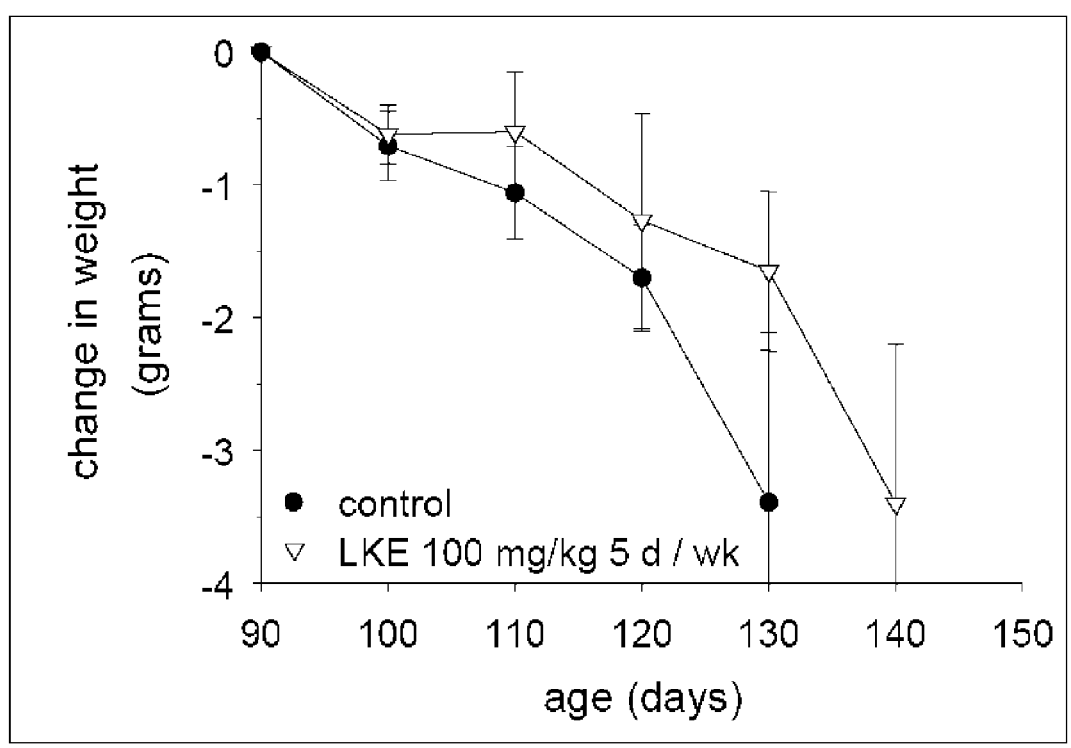
FIG. 12. (R)-LKE1 inhibited weight loss in G93A-SOD1 mice. The mice were administered 100 mg/kg of (R)-LKE1 for 5 days/week. (The control group was given saline injection.) "LKE" refers to (R)-LKE1.

As shown in FIG. 11, rotarod performance in G93A-SOD mice improved as a result of (R)-LKE1 administration. Additionally, as shown in FIG. 12, (R)-LKE1 inhibited weight loss in G93A-SOD mice. (R)-LKE1 was administered i.p. in saline beginning at day 90. These results demonstrate that beneficial in vivo effects may be observed as a result of (R)-LKE1 administration.

Example 6

Treatment of Sepsis in Mouse Model

Six mice were treated with 40 mg/kg *E. coli* LPS 0127:B8 and co-treated with 100 mg/kg (R)-LKE1 i.p., daily. Viability was compared to a control group, receiving only LPS. The results are shown in Table 1 below:

TABLE 1

| Time (h) | Dead/alive vehicle group | Dead/alive LKE group |
| --- | --- | --- |
| 0 | 0/6 | 0/6 |
| 18 h | 1/5 | 2/4 |
| 36 h | 4/2 | 3/3 |
| 48 h | 6/0 | 4/2 |
| 72 h | 6/0 | 4/2 |

Example 7

TNFα Production by Human Monocytes in Response to Bacterial Cell Wall Components is Inhibited by (R)-LKE1

(R)-LKE1 inhibits TNFα production by human PB monocytes in response to two cell wall components: lipopolysaccharide (UltraPure LPS) from *Staphylococcus aureus* (Invivogen) and peptidoglycan (PG) from *Bacillus anthracis* (List Biological Laboratories).

Identification of TNFα positive monocytes in peripheral blood by flow cytometry: PB monocytes expressing TNF in response to LPS or PG can be identified and counted using flow cytometry with fluorescent antibodies to stain TNFα. To identify the percentage of monocytes expressing TNFα, PB was stimulated with LPS or PG, stained for surface markers to distinguish monocytes from other leukocytes, and stained for intracellular TNFα to identify monocytes expressing TNFα. The percentage of monocytes positive for TNFα was compared among samples stimulated with LPS, PG, with and without pretreatment with (R)-LKE1, and non-stimulated samples.

The fluorescent antibodies used to identify monocytes surface markers were anti-human CD14-phycoerythrin (PE) and antiCD16b-fluorescein isothyocyanate (FITC), based on staining intensity for each marker. Monocytes are positive for CD14 and negative for CD16b. This method of separating monocytes from neutrophils was confirmed by sorting cells based on CD14/CD16b intensity, preparing slides, staining with May-Grunwald Giemsa and confirming by morphology.

For analysis of CD14 positive, CD16b negative cells we used dot plots. We first excluded lymphocytes from the analysis by their forward scatter (FSC) and side scatter (SSC) properties, drawing a monocyte/neutrophil gate to exclude lymphocytes (not shown). We then identified CD14+, (y-axis) CD16b– (x-axis) cells by comparison with an unstained sample.

A third dye, PE-Cye7 was used for intracellular cytokine staining of TNFα. The TNFα positive monocytes were identified on a second dot plot of SSC vs. TNFα PE-Cye7 for monocytes only. Cells were counted as positive for TNFα expression if the intensity of PE-Cye7 was greater than in the non-stimulated control. The percent of TNFα positive monocytes was calculated using number positive/total number of monocytes.

PB, heparinized, was diluted 1:3 with DMEM. Diluted blood was placed in 1.0 ml aliquots into wells of a non tissue culture plate. PB was pre-incubated at 37° C. for one hour with LKE (1 mM) or the diluent DMSO (10 μl). PG (10 ug/ml) or Ultra Pure LPS (1 μg/ml) was added to wells either preincubated with (R)-LKE1 or not. Brefeldin A 1000X (BFA), 1 μl, was added to the solution in wells and mixed.

The plate was incubated at 37° C. for two hours. The blood was removed to microfuge tubes. Wells were washed with 300 µl 1×PBS/BFA, 0.02% EDTA to removed cells on the bottom and the solution and cells were added to microfuge tubes.

The samples were centrifuged at 500 RCF, 5 minutes, washed in 100 µl SWB (1×PBS, 2% FBS, 0.1% NaN$_3$)/BFA and resuspended in 100 µl SWB/BFA. Human IgG (0.1 mg/ml) was added. The samples were vortexed and placed on ice foir 10 minutes. Anti-human CD16b-FITC (20 µl) (Accurate chemical) and anti-human CD14-PE (20 µl) (eBioscience) were added. Samples were vortexed and placed on ice 20 minutes.

Samples were centrifuged and supernatant was removed. Red cells were lysed for 5 minutes with 1 ml ACK lysis buffer and washed twice with 500 µl 1×PBS/BFA. Cells were resuspended in 100 µl 1×PBS/BFA and fixed for 20 minutes at room temperature with 100 µl 1×PBS, 2% formaldehyde.

Samples were placed on ice O/N in the dark at 4° C., washed with 1×PBS, resuspended in 100 µl permeabilization buffer (SWB, 0.5% saponin) and incubated at RT for 10 minutes. 100 µl permeabilization buffer was added and 1 µl anti-human TNFα-PE Cye7 (eBioscience). Samples were vortexed and placed on ice 50 minutes. 1 ml of SWB was added, cells were centrifuged and resuspended in 500 µl SWB for analysis by flow cytometry. Data was collected on 10,000 leukocytes per sample.

Monocytes were identified as cells staining positively for CD14 and negatively for CD16b. The percent monocytes staining positively for TNFα and total number of monocytes per sample of 10,000 cells is as follows (FIG. 17): Non-stimulated, 0.13% (777); PG, 11.5% (601); LKE pre-incubation with PG, 0.76% (527); Ultra Pure LPS, 63.8% (738); (R)-LKE1 pre-incubation with Ultra Pure LPS, 25.9% (471); DMSO pre-incubation+PG, 11.62% (456); DMSO pre-incubation+Ultra Pure LPS, 75.71% (280); LKE, 0.96% (727); DMSO, 1.0% (580).

Example 8

Use of LK and LK-derivatives for the Prevention and Treatment of Stroke. (A Prophetic Example)

The potential of the compounds of this invention to prevent and/or treat stroke would be demonstrated using mammal models. For example, one could set up the following experiment using the gerbil carotid artery occlusion model. Adult Mongolian gerbils would be anesthetized and the carotid arteries exposed.

Surgical sutures are placed around the carotids and extruded through a double-lumen catheter that is made to exit posterior to the ears; the suture is not tightened around the artery but rather is made into a loop that can be tightened later, by means of external tension. The surgical field is closed and the animal allowed to recover from anesthesia for 2 days. At that point, or prior to that point LK, an LK-derivative, and/or a compound of this invention is administered to animals in a treatment group while vehicle (e.g. saline) is administered to a control group of animal. For example in the case of LK or (R)-LKE1, the dose may be 50 mg/kg to 1 g/kg given intraperitoneally, in drinking water or in food.

At this point, one external surgical suture is subjected to tension thereby occluding blood flow through the carotid artery for a period of 5-15 minutes. Tension is released and reperfusion is allowed to occur for 0 min to 72 h. Ischemia/reperfusion damage can be measured by means of magnetic resonance imaging (MRI) volumetric assessments or by histological examinations of the brain. Behavioral tests can be performed upon the animals also (e.g. rotarod tests as were performed on G93A-SOD1 animals). Biochemical studies can be performed on cortical tissues. One would assess quantitative damage to the hemisphere of the brain subjected to carotid artery-ischemia/reperfusion, and compare these changes to the contralateral (control hemisphere). Data would be further compared between groups of animals receiving LK/LKE and those receiving saline vehicle.

A person skilled in the art would recognize that other mammalian models of stroke (cerebral ischemia/reperfusion) may also be used.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,683,195
U.S. Pat. No. 5,399,363
U.S. Pat. No. 5,466,468
U.S. Pat. No. 5,543,158
U.S. Pat. No. 5,580,579
U.S. Pat. No. 5,629,001
U.S. Pat. No. 5,641,515
U.S. Pat. No. 5,725,871
U.S. Pat. No. 5,756,353
U.S. Pat. No. 5,780,045
U.S. Pat. No. 5,804,212
U.S. Pat. No. 6,613,308
U.S. Pat. No. 6,753,514
U.S. Pat. No. 5,792,451
U.S. Pat. No. 6,025,395
U.S. Pat. No. 5,804,212
U.S. Publn. 2003/0185754
Ausubel et al., In: *Current Protocols in Molecular Biology*, John, Wiley & Sons, Inc, NY, 1994.
Bagasra et al., *Proc. Natl. Acad. Sci. USA*, 92:12041-12045, 1995.
Beal et al., *Nature*, 321:168-171, 1986.
Beal, *Curr. Opin. Neurobiol.*, 6:661-666, 1996.
Bensimon et al., *J. Neurol.*, 249:609-615, 2002.
Blight et al., *J. Neurotraum.*, 14:89-98; 1997.
Brown et al., *Journal of Biological Chemistry* 140:767-771, 1941.
Cashman et al., *Dev. Dyn.*, 194:209-221, 1992.
Cavallini et al., *Eur. J. Biochem.*, 202:217-223; 1991.
Cavallini et al., *FEBS Lett.*, 3122:247-250; 1985.

Cavallini et al., In: *Sulfur Amino Acids: Biochemical and Clinical Aspects*, Alan R. Liss Inc., 355-364, 1983.
Chiarugi et al., *Neurosci.*, 102:687-695; 2001.
Cooper, *Neurochem. Int.*, 44:557-577; 2004.
Coyle and Puttfarcken, *Science,* 262:689-695, 1993.
Culver et al., *Science,* 256(5063):1550-1552, 1992.
Desagher et al., *J. Neurosci.*, 17:9060-9067, 1997.
Fontana et al., *Biochem. Biophys. Res. Commun.*, 171:480-486; 1990.
Fontana et al., *Neurochem. Res.*, 22:821-844; 1997.
Foster et al., *Mol. Pharmacol.*, 41:910-922, 1992.
Gait, In: *Oligonucleotide Synthesis: A Practical Approach*, IRL Press Oxford, United Kingdom, 1984.
Giulidori et al., *J. Biol. Chem.*, 259:4205-4211, 1984.
Glover, In: *DNA Cloning*, Volumes I and II, 1985.
Guidetti et al., *Neurobiol. Dis.*, 17:455-461; 2004.
Guillemin et al., *Adv. Exp. Med. Biol.*, 527:167-176; 2003.
Guillemin et al., *Neurodegener. Dis.*, 2:166-176, 2005.
Guillemin et al., *Neuropathol. Appl. Neurobiol.*, 31:395-404; 2005.
Gurney et al., *Ann. Neurol.*, 39:147-157, 1996.
Hames and Higgins, In: *Nucleic acid hybridisation: a practical approach*, IRL, Oxford, UK, 1985.
Harpp et al., *Journal of Organic Chemistry* 36:73-80, 1971.
Hensley et al., *J. Neurochem.*, 82:365-374, 2002.
Hensley et al., *J. Neuroinflammation*, 3:2; 2006.
Hensley et al., *Neurobio. Dis.* 14: 74-80; 2003
Hermann, *Chemische Berichte*, 94:442-445, 1961.
Heyes, *Adv. Exp. Med. Biol.*, 398:125-129, 1996.
Horn et al., *Journal of Biological Chemistry* 138:141-149, 1941.
Huang et al., *Proc Natl Acad Sci USA*. 98(20):11720-4, 2001.
Hwang et al., *Crit. Rev. Ther. Drug Carrier Syst.*, 15(3):243-284, 1998.
Jauch et al., *J. Neurol. Sci.*, 130:39-47, 1995.
Kaltschmidt et al. *Proc. Natl. Acad. Sci. USA*, 94:2642-2647, 1997.
Magnuson et al., *Can. J. Physiol. Pharm.*, 65:2483-2487, 1987.
Manfredini et al., *Bioorg Med. Chem.* 8(12):2791-801, 2000.
Mathiowitz et al., *Nature,* 386(6623):410-414, 1997.
Mayer and Walker, In: *Immunochemical Methods in Cell and Molecular Biology*, Academic Press, 1988.
McGeer and McGeer, *Brain Res. Brain Res. Rev.*, 21:195-218, 1995.
McGeer et al., *Neurology,* 19:331-338, 1996.
Merrill and Benvenist, *Trends Neurosci.*, 19:331-338, 1996.
Moroni, *Eur. J. Pharmacol.*, 375:87-100, 1999.
Nakamichi et al., *J. Neurochem.*, 93:84-93, 2005.
Paul et al., *Mini-Reviews in Organic Chemistry* 2:23-37, 2005.
Pharmaceutical Salts: Properties, Selection and Use—A Handbook, by C. G. Wermuth and P. H. Stahl, Verlag Helvetica Chimica Acta, 2002.
Probert et al., *Tetrahedron Letters* 37:1101-1104, 1996.
Remington's Pharmaceutical Sciences, 15$^{th}$ ed., pages 1035-1038 and 1570-1580, Mack Publishing Company, Easton, Pa., 1980.
Remington's Pharmaceutical Sciences, 19th Ed. Mack Printing Company, 1995.
Remington's Pharmaceutical Sciences, 20th Ed. Lippincott Williams & Wilkins, 2003.
Sambrook et al., In: *Molecular cloning: a laboratory manual*, 2$^{nd}$ Ed., Cold Spring Harbor Laboratory Press, Cold Spring Harbor, N.Y., 1989.
Schiefer et al., *Mov. Disord.*, 17:748-757, 2002.
Sen et al., *Ann. NY Acad. Sci.*, 1031:127-142, 2004.
Shao et al., *Journal of Organic Chemistry* 60:2956-2957, 1995.
Simonian and Coyle, *Annu. Rev. Pharmacol. Toxicol.*, 36:83-106, 1996
Stewart et al., *Neurology,* 48:626-632, 1997.
Stone and Darlington, *Nat. Drug Disc.*, 1:609-620, 2002.
Stoy et al., *J. Neurochem.*, 93:611-623; 1995.
Stryer, In: *Biochemistry*, 4$^{th}$ Ed.; W.H. Freeman, 1995.
Takenaga et al., *J. Control Release,* 52(1-2):81-87, 1998.
Tirosh et al., *Neurosci.*, 97:531-541, 2000.
Urenjak, *NeuroReport,* 11: 1341-1344, 2000.
Vodovotz et al., In; *Handbook of Experimental Immunology*, Volumes I-IV, 1996.
Walker et al., *J. Neuroimmunol.*, 63:163-174, 1995.
Weir and Blackwell, In: *Handbook Of Experimental Immunology*, Volumes I-IV, 1986.
West et al., *J. Neurochem.*, 91:133-143, 2004.
Widner et al., *J, Neural, Transm.*, 107:343-353; 2000.

What is claimed is:

1. A compound having the structure:

wherein $R_1$ is —OH, —NH$_2$, —OCH$_3$, —OCH$_2$CH$_2$CH$_3$, —OCH(CH$_3$)$_2$, —OCH(CH$_2$)$_2$, or heteroatom substituted or unsubstituted versions of C$_2$-C$_{10}$-alkenyloxy, C$_2$-C$_{10}$-alkynyloxy, C$_1$-C$_{10}$-aryloxy, C$_2$-C$_{10}$-aralkoxy, C$_1$-C$_{10}$-acyloxy, C$_1$-C$_{10}$-alkylamino, C$_2$-C$_{10}$-alkenylamino, C$_2$-C$_{10}$-alkynylamino, C$_1$-C$_{10}$-arylamino, C$_2$-C$_{10}$-aralkylamino, or C$_1$-C$_{10}$-amido;

wherein $R_2$ is —OH, —NH$_2$, or heteroatom substituted or unsubstituted versions of C$_2$-C$_{10}$-alkoxy, C$_2$-C$_{10}$-alkenyloxy, C$_2$-C$_{10}$-alkynyloxy, C$_1$-C$_{10}$-aryloxy, C$_2$-C$_{10}$-aralkoxy, C$_1$-C$_{10}$-acyloxy, C$_1$-C$_{10}$-alkylamino, C$_2$-C$_{10}$-alkenylamino, C$_2$-C$_{10}$-alkynylamino, C$_1$-C$_{10}$-arylamino, C$_2$-C$_{10}$-aralkylamino, or C$_1$-C$_{10}$-amido;

provided that $R_1$ and $R_2$ are not both —OH;

is —OCH$_3$ and $R_1$ is —OH, then the compound is predominantly one enantiomer, and pharmaceutically acceptable salts and optical isomers thereof.

2. The compound of claim 1, wherein $R_1$ is —OCH$_3$, —OCH$_2$CH$_2$CH$_3$, —OCH(CH$_3$)$_2$ or —OCH(CH$_2$)$_2$.

3. The compound of claim 1, wherein $R_2$ is a heteroatom substituted or unsubstituted C$_2$-C$_{10}$-alkoxy.

4. The compound of claim 1, wherein $R_1$ is a heteroatom substituted or unsubstituted C$_2$-C$_{10}$-alkenyloxy.

5. The compound of claim 1, wherein $R_2$ is a heteroatom substituted or unsubstituted C$_2$-C$_{10}$-alkenyloxy.

6. The compound of claim 1, wherein $R_1$ is a heteroatom substituted or unsubstituted C$_1$-C$_{10}$-aryloxy.

7. The compound of claim 1, wherein $R_2$ is a heteroatom substituted or unsubstituted C$_1$-C$_{10}$-aryloxy.

8. The compound of claim 1, wherein $R_1$ or $R_2$ is —NH$_2$.

9. The compound of claim 1, wherein $R_1$ is a heteroatom substituted or unsubstituted C$_1$-C$_{10}$-alkylamino.

10. The compound of claim 1, wherein $R_2$ is a heteroatom substituted or unsubstituted C$_1$-C$_{10}$-alkylamino.

11. The compound of claim 1, wherein $R_1$ is selected from the group consisting of ascorbyl, dehydroascorbate, glycinyl, and serinyl.

12. The compound of claim 1, wherein $R_2$ is selected from the group consisting of ascorbyl, dehydroascorbate, glycinyl, and serinyl.

13. The compound of claim 1, further defined as:

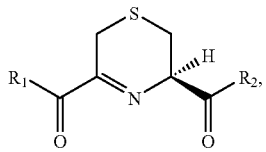

substantially free from other optical isomers, and pharmaceutically acceptable salts thereof.

14. The compound of claim 1, further defined as:

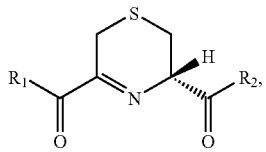

substantially free from other optical isomers, and pharmaceutically acceptable salts thereof.

15. The compound of claim 13, further defined as

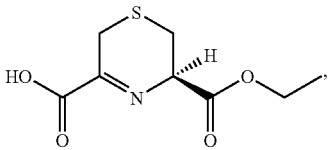

substantially free from other optical isomers, and pharmaceutically acceptable salts thereof.

16. The compound of claim 14, further defined as

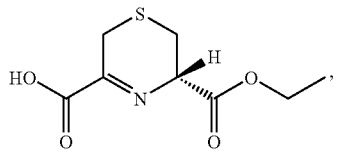

substantially free from other optical isomers, and pharmaceutically acceptable salts thereof.

17. The compound of claim 12, further defined as:

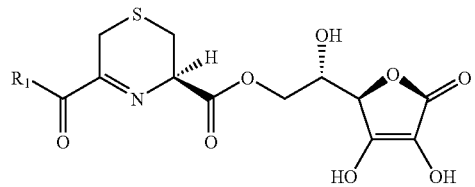

substantially free from other optical isomers, and pharmaceutically acceptable salts thereof.

18. The compound of claim 12, further defined as:

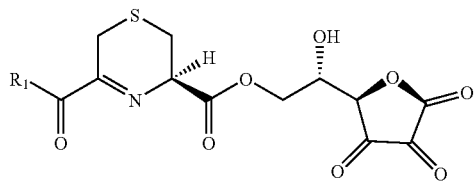

substantially free from other optical isomers, and pharmaceutically acceptable salts thereof.

19. A compound having the structure:

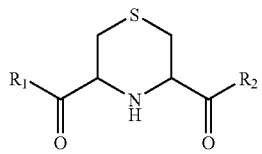

wherein:
$R_1$ is —OH, —NH$_2$, or heteroatom substituted or unsubstituted versions of $C_1$-$C_{10}$-alkoxy, $C_2$-$C_{10}$-alkenyloxy, $C_2$-$C_{10}$-alkynyloxy, $C_1$-$C_{10}$-aryloxy, $C_2$-$C_{10}$-aralkoxy, $C_1$-$C_{10}$-acyloxy, $C_1$-$C_{10}$-alkylamino, $C_2$-$C_{10}$-alkenylamino, $C_2$-$C_{10}$-alkynylamino, $C_1$-$C_{10}$-arylamino, $C_2$-$C_{10}$-aralkylamino, or $C_1$-$C_{10}$-amido;

$R_2$ is —OH, or heteroatom substituted or unsubstituted versions of $C_2$-$C_{10}$-alkenyloxy, $C_1$-$C_{10}$-alkynyloxy, $C_1$-$C_{10}$-aryloxy, $C_2$-$C_{10}$-aralkoxy, $C_1$-$C_{10}$-acyloxy, $C_1$-$C_{10}$-alkylamino, $C_2$-$C_{10}$-alkenylamino, $C_2$-$C_{10}$-alkynylamino, $C_1$-$C_{10}$-arylamino, $C_2$-$C_{10}$-aralkylamino, or $C_1$-$C_{10}$-amido; provided that $R_1$ and $R_2$ are not both —OH;

or pharmaceutically acceptable salts, and optical isomers thereof.

20. The compound of claim 19, wherein $R_1$ is a heteroatom substituted or unsubstituted $C_2$-$C_{10}$-alkoxy.

21. The compound of claim 19, wherein $R_1$ is a heteroatom substituted or unsubstituted $C_2$-$C_{10}$-alkenyloxy.

22. The compound of claim 19, wherein $R_1$ is a heteroatom substituted or unsubstituted $C_1$-$C_{10}$-aryloxy.

23. The compound of claim 19, wherein $R_2$ is a heteroatom substituted or unsubstituted $C_1$-$C_{10}$-aryloxy.

24. The compound of claim 19, wherein $R_1$ is —NH$_2$.

25. The compound of claim 19, wherein $R_1$ or $R_2$ is a heteroatom substituted or unsubstituted $C_1$-$C_{10}$-alkylamino.

26. The compound of claim 19, wherein $R_1$ is selected from the group consisting of ascorbyl, dehydroascorbate, glycinyl, and serinyl.

27. The compound of claim 19, wherein $R_2$ is selected from the group consisting of ascorbyl, dehydroascorbate, glycinyl, and serinyl.

28. The compound of claim 19, further defined as:

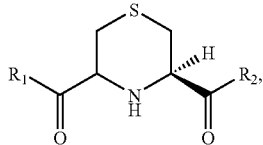

substantially free from other optical isomers, and pharmaceutically acceptable salts thereof.

29. The compound of claim 19, further defined as:

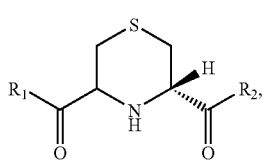

substantially free from other optical isomers, and pharmaceutically acceptable salts thereof.

30. The compound of claim 28, further defined as

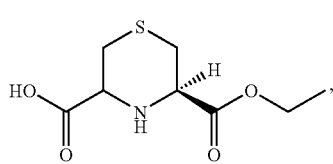

substantially free from other optical isomers, and pharmaceutically acceptable salts thereof.

31. The compound of claim 29, further defined as

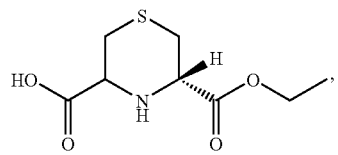

substantially free from other optical isomers, and pharmaceutically acceptable salts thereof.

32. A method of treating a disease in a subject, wherein the disease is sepsis, Parkinson's disease, Huntington's disease, multiple sclerosis, macular degeneration, atherosclerosis, rheumatoid arthritis, inflammatory bowel disease (IBD), hypertension, attention deficit disorder, major depression, anxiety disorder, stroke, brain cancer, lung cancer, liver cancer, spleen cancer, kidney cancer, lymph node cancer, small intestinal cancer, pancreatic cancer, colon cancer, stomach cancer, prostate cancer, testicular cancer, ovarian cancer, or esophageal cancer, comprising administering to a subject a pharmacologically effective amount of a compound of claim 1.

33. The method of claim 32, wherein the subject is a mammal.

34. The method of claim 32, wherein the subject is a human.

35. The method of claim 32, wherein the disease is sepsis.

36. The method of claim 32, wherein the disease is Parkinson's disease, Huntington's disease, multiple sclerosis, macular degeneration, atherosclerosis, rheumatoid arthritis or inflammatory bowel disease (IBD).

37. The method of claim 32, wherein said subject had a stroke.

38. The method of claim 32, wherein the disease is brain cancer, lung cancer, liver cancer, spleen cancer, kidney cancer, lymph node cancer, small intestinal cancer, pancreatic cancer, colon cancer, stomach cancer, prostate cancer, testicular cancer, ovarian cancer, or esophageal cancer.

* * * * *

UNITED STATES PATENT AND TRADEMARK OFFICE
CERTIFICATE OF CORRECTION

PATENT NO. : 7,683,055 B2  Page 1 of 1
APPLICATION NO. : 11/621469
DATED : March 23, 2010
INVENTOR(S) : Kenneth Hensley et al.

It is certified that error appears in the above-identified patent and that said Letters Patent is hereby corrected as shown below:

In claim 1, column 58, lines 46-47, delete "is —$OCH_3$ and $R_1$ is —OH, then the compound is predominantly one enantiomer,".

In claim 19, column 60, line 40, delete "$C_1$-$C_{10}$-alkynyloxy" and insert -- $C_2$-$C_{10}$-alkynyloxy -- therefor.

Signed and Sealed this

Third Day of August, 2010

David J. Kappos
*Director of the United States Patent and Trademark Office*

UNITED STATES PATENT AND TRADEMARK OFFICE
CERTIFICATE OF CORRECTION

Page 1 of 1

PATENT NO.       : 7,683,055 B2
APPLICATION NO.  : 11/621469
DATED            : March 23, 2010
INVENTOR(S)      : Kenneth Hensley It is certified that error appears in the above-identified patent and that said Letters Patent is hereby corrected as shown below:

In The Specification

In column 1, lines 10-15, delete
"This invention was made with government support under grant numbers AG20783 and NS044154 awarded by the National Institutes of Health and grant number HR02-149RS awarded by the Oklahoma Center for the Advancement of Science and Technology. The government has certain rights in the invention."
and insert
--This invention was made with government support under grant numbers AG20783 and NS044154 awarded by the National Institutes of Health. The government has certain rights in the invention.--
therefor.

Signed and Sealed this
Eighteenth Day of November, 2014

Michelle K. Lee
*Deputy Director of the United States Patent and Trademark Office*